(12) United States Patent
McDowell et al.

(10) Patent No.: US 8,143,896 B2
(45) Date of Patent: Mar. 27, 2012

(54) MICROCOIL MAGNETIC RESONANCE DETECTORS

(75) Inventors: Andrew F McDowell, Albuquerque, NM (US); Eiichi Fukushima, Albuquerque, NM (US); Victor Esch, Albuquerque, NM (US); Meghan Norvell, Albuquerque, NM (US); Laurel Sillerud, Albuquerque, NM (US)

(73) Assignees: ABQMR, Inc., Albuquerque, NM (US); NanoMR, Inc., Albuquerque, NM (US)

( * ) Notice: Subject to any disclaimer, the term of this patent is extended or adjusted under 35 U.S.C. 154(b) by 530 days.

(21) Appl. No.: 12/257,238

(22) Filed: Oct. 23, 2008

(65) Prior Publication Data

US 2009/0146658 A1    Jun. 11, 2009

Related U.S. Application Data

(60) Provisional application No. 60/981,948, filed on Oct. 23, 2007, provisional application No. 61/099,975, filed on Sep. 25, 2008.

(51) Int. Cl.
*G01V 3/00* (2006.01)
(52) U.S. Cl. .......................... 324/322; 324/318
(58) Field of Classification Search .................. 324/322, 324/318, 300, 306
See application file for complete search history.

(56) References Cited

U.S. PATENT DOCUMENTS

| | | | |
|---|---|---|---|
| 4,901,018 A | 2/1990 | Lew | |
| 5,136,095 A | 8/1992 | Tarnowski et al. | |
| 5,164,297 A | 11/1992 | Josephson et al. | |
| 5,254,460 A | 10/1993 | Josephson et al. | |
| 5,338,687 A | 8/1994 | Lee et al. | |
| 5,654,636 A | 8/1997 | Sweedler et al. | |
| 5,677,133 A | 10/1997 | Oberhardt | |
| 5,684,401 A | 11/1997 | Peck et al. | |
| 5,773,307 A | 6/1998 | Colin et al. | |
| 5,925,573 A | 7/1999 | Colin et al. | |
| 6,097,188 A | 8/2000 | Sweedler et al. | |
| 6,194,900 B1 | 2/2001 | Freeman et al. | |
| 6,242,915 B1 | 6/2001 | Hurd | |
| 6,307,372 B1 | 10/2001 | Sugerman et al. | |
| 6,361,944 B1 | 3/2002 | Mirkin et al. | |
| 6,404,193 B1 * | 6/2002 | Dourdeville | 324/306 |
| 6,456,072 B1 | 9/2002 | Webb et al. | |
| 6,512,941 B1 | 1/2003 | Weiss et al. | |

(Continued)

FOREIGN PATENT DOCUMENTS

CA    2342047 A1    9/2001

(Continued)

OTHER PUBLICATIONS

Abragam, "Principles of Nuclear Magnetism," *Clarendon Press*, Oxford, 1961, pp. 71-83.

(Continued)

*Primary Examiner* — Louis Arana
(74) *Attorney, Agent, or Firm* — Brown Rudnick LLP; Thomas Meyers; Adam Schoen

(57) ABSTRACT

The present invention provides microcoil magnetic resonance based modules, detection devices, and methods for their use. In certain embodiments, the invention provides a module including a microcoil possessing an inner diameter of between 25 microns and 550 microns, a conduit disposed proximate to the microcoil, in which the conduit is in fluid communication with a sample reservoir, an affinity column in fluid communication with the conduit and the sample reservoir, and a connector for connecting the module to a magnetic resonance detector.

20 Claims, 15 Drawing Sheets

U.S. PATENT DOCUMENTS

| | | | |
|---|---|---|---|
| 6,696,838 | B2 | 2/2004 | Raftery et al. |
| 6,700,379 | B2 * | 3/2004 | Peck et al. .................... 324/321 |
| 6,788,061 | B1 | 9/2004 | Sweedler et al. |
| 6,822,454 | B2 | 11/2004 | Peck et al. |
| 6,958,609 | B2 | 10/2005 | Raftery et al. |
| 7,141,978 | B2 | 11/2006 | Peck et al. |
| 7,202,667 | B2 | 4/2007 | Barbic |
| 7,271,592 | B1 | 9/2007 | Gerald, II et al. |
| 7,274,191 | B2 | 9/2007 | Park et al. |
| 7,345,479 | B2 | 3/2008 | Park et al. |
| 7,403,008 | B2 | 7/2008 | Blank et al. |
| 7,405,567 | B2 | 7/2008 | McDowell |
| 7,564,245 | B2 | 7/2009 | Lee |
| 2002/0130661 | A1 | 9/2002 | Raftery et al. |
| 2003/0092029 | A1 | 5/2003 | Josephson et al. |
| 2003/0222648 | A1 | 12/2003 | Fan |
| 2004/0018611 | A1 | 1/2004 | Ward et al. |
| 2007/0090836 | A1 | 4/2007 | Xiang et al. |
| 2007/0116602 | A1 | 5/2007 | Lee |
| 2007/0152669 | A1 | 7/2007 | Park et al. |
| 2007/0152670 | A1 | 7/2007 | Park et al. |
| 2008/0204022 | A1 | 8/2008 | Sillerud et al. |
| 2008/0272788 | A1 | 11/2008 | McDowell |
| 2008/0315875 | A1 | 12/2008 | Sillerud |
| 2009/0256572 | A1 | 10/2009 | McDowell |

FOREIGN PATENT DOCUMENTS

| | | |
|---|---|---|
| EP | 1304581 A2 | 10/2002 |
| WO | WO 01/73460 A1 | 10/2001 |
| WO | WO 02/098364 | 12/2002 |
| WO | WO 2005/026762 | 3/2005 |
| WO | WO 2008/119054 | 12/2008 |

OTHER PUBLICATIONS

Armenean et al., "NMR Radiofrequency Microcoil Design: Electromagnetic Simulation Usefulness," *Compes Rendus—Biologies*, Elsevier, Paris, vol. 325, No. 4, Apr. 1, 2002, pp. 457-463.

Armenean et al., "Solenoidal and Planar Microcoils for NMR Spectroscopy," *Proceedings of the 25th Annual International Conference of the IEEE Engineering in Medicine and Biology Society*, Cancun, Mexico, Sep. 17, 2003, pp. 3045-3048.

Fukushima, et al., "Experimental Pulse NMR; A Nutes and Bolts Approach," *Addison-Wesley Publ. Co.*, MA, 1981, pp. 311, 342, 374.

Goloshevsky, A.G., et al. "Development of Low Field Nuclear Magnetic Resonance Microcoils," *Rev. Sci. Inst.*, vol. 76, 2005, pp. 024101-1 through 024101-6.

Hoult et al., "The Signal-to-Noise Ratio of the Nuclear Magnetic Resonance Experiment," *J. Magn. Reson.*, vol. 24,1976, pp. 71-85.

Kaittanis et al., One-Step, Nanoparticle-Mediated Bacterial Detection with Magnetic Relaxation,: Nano Letters, vol. 7, No. 2, 2007, pp. 381-383.

Lee et al., "Chip-NRM Biosensor for Detection and Molecular Analysis of Cells," Nature Medicine, vol. 14, No. 8, Aug. 2008, pp. 869-874.

Listing of Claims for International Application No. PCT/US/2008/062473, filed May 2, 2008, 4 pages.

Listing of Claims for International Application No. PCT/US2008/058518 filed Mar. 27, 2008, 8 pages.

Listing of Claims for International Application No. PCT/US2009/067577 filed Dec. 10, 2009, 14 pages.

Magin et al., "Miniature Magnetic Resonance Machines," *IEEE Spectrum*, IEEE Inc. New York, vol. 34, No. 10, Oct. 1, 1997, pp. 51-61.

Massin et al., "Planar Microcoil-Based Magnetic Resonance Imaging of Cells," *Transducers '03, The 12th International Conference on Solid State Sensors, Actuators and Microsystems*, Boston, Jun. 8-12, 2003, pp. 967-970.

McDowell et al., "Low-Field Micro-Coil Probe Development for Portable NMR," 8th ICMRM, The Heidelberg Conference, Mibu, Japan, Aug. 22-26, 2005, 14 pages. (pp. 2-14 are a magnification of p. 1).

McDowell et al., "Low-Field Micro-Coil Probe Development for Portable NMR," 8th ICMRM, The Heidelberg Conference, Mibu, Japan, Conference Program Abstract, Aug. 22-26, 2005, 1 page.

McDowell et al., "Operating Nanoliter Scale NMR Microcoils in a Itesla Field," Journal of Magnetic Resonance, Academic Press, Orlando, Florida, vol. 188, No. 1, Sep. 1, 2007, pp. 74-82.

Minard et al., "Solenoidal Microcoil Design, Part 1: Optimizing rf Homogeneity," *Concepts in Magn. Reson.*, vol. 13, 2001, pp. 128-142.

Moresi, G., et al., Miniature Permanent Magnet for Table-Top NMR, *Concept. Magn. Reson.*, V. 19B, 2003, pp. 35-43.

Notification of Transmittal of the International Search Report and the Written Opinion of the International Searching Authority, or the Declaraiton for ABQMR, Inc., International Application No. PCT/US2008/058518, mailed Jul. 7, 2008, 21 pages.

Notification of Transmittal of the International Search Report and the Written Opinion of the International Search Authority, or the Declaration, International Application No. PCT/US/2008/062473, mailed Oct. 29, 2008, 23 pages.

Notification of Transmittal of the International Search Report and the Written Opinion of the International Searching Authority, or the Declaration for International Application No. PCT/US2009/067577 mailed Feb. 5, 2010, 13 pages.

Peck et al., "Design and Analysis of Microcoils for NMR Microscopy," *J. Magn. Reson.*, vol. 108, 1995, pp. 114-124.

Peck et al., "RF Microcoils Patterned Using Microlithographic Techniques for Use as Microsensors in NMR," *Engineering in Medicine and Biology Society*, Proceedings of the 15th Annual international Conference of the IEEE Oct. 28-31, 1993, pp. 174-175.

Seeber et al., "Design and Testing of High Sensitivity Microreceiver Coil Apparatus for Nuclear Magnetic Resonance and Imagin," *Rev. Sci. Inst.*, vol. 72, 2001, p. 2171-2179.

Seeber et al., "Triaxial Magnetic Field Gradient System for Microcoil Magnetic Resonance Imaging," *Review of Scientific Instruments*, vol. 71, No. 11, Nov. 2000, pp. 4263-4272.

Siilerud et al., "1 H NMR Detection or Superparamagnetic Nanoparticles at 1T Using a Microcoil and Novel Tuning Circuit," *Journal of Magnetic Resonance*, Academic Press, Orland, Florida, Aug. 1, 2006, pp. 181-190.

Sorli et al., "Micro-Spectrometer for NMR: Analysis of Small Quantities in Vitro," *Mes. Sci. Technol.*, vol. 15, 2004, pp. 877-880.

Subramanian et al., "RF Microcoil Design for Practical NMR of Mass-Limited Samples," *Journal of Magnetic Resonance*, Academic Press, Orlando, Florida, vol. 133, No. 1, Jul. 1, 1998, pp. 227-231.

Taktak et al., Multiparameter Magnetic Relaxation Switch Assays, Analytical Chemistry, vol. 79, No. 23, Dec. 1, 2007, pp. 8863-8869.

U.S. Appl. No. 12/720,541 entitled "Tuning Low-Inductance Coils at Low Frequencies," filed Mar. 9, 2010, 39 pages.

U.S. Appl. No. 12/635,583 entitled "Nuclear Magnetic Resonance Apparatus, Methods and Associated Technology," filed Dec. 10, 2009, 66 pages.

U.S. Appl. No. 12/720,499 entitled "Biological Detector and Method," filed Mar. 9, 2010, 43 pages.

U.S. Appl. No. 60/927,456, filed May 3, 2007, 25 pages.
U.S. Appl. No. 61/121,416, filed Dec. 10, 2008, 5 pages.
U.S. Appl. No. 60/839,006, filed Aug. 21, 2006, 15 pages.
U.S. Appl. No. 60/920,165, filed Mar. 27, 2007, 16 pages.

Van Bentum et al., "Towards Nuclear Magnetic Resonance µ-Spectroscopy and µ -Imaging," *Analyst, Royal Society of Chemistry*, London, vol. 129, No. 9, Jan. 1, 2004, pp. 793-803.

Pappas et al., "Cellular Separations: A Review of New Challenges in Analytical Chemistry," *Analytica Chemica Acta*, 601, 2007, pp. 26-36.

U.S. Appl. No. 60/981,948, filed Oct. 23, 2007, 35 pages.
U.S. Appl. No. 61/099,975, filed Sep. 25, 2008, 87 pages.

Notification of Transmittal of the International Search Report and the Written Opinion of the International Search Authority, or the Declaration, International Application No. PCT/US2008/080983, mailed Mar. 3, 2009, 20 pages.

Listing of Claims for International Application No. PCT/US2008/080983, filed Oct. 23, 2008, 8 pages.

* cited by examiner

MICROCOIL MAGNETIC RESONANCE DETECTORS

CROSS REFERENCE

This application claims priority to U.S. Provisional Patent Application Ser. Nos. 60/981,948 filed Oct. 23, 2007 and 61/099,975 filed Sep. 25, 2008, both hereby incorporated by reference in their entirety.

FIELD OF INVENTION

The present invention relates to magnetic resonance and detection of labeled targets.

BACKGROUND OF THE INVENTION

A variety of experiments in Nuclear Magnetic Resonance (NMR) could benefit from miniaturization of the detector coil. When samples are mass-limited, reducing the detection volume to match the sample size offers enhanced Signal-to-Noise-Ratio (SNR) performance. While some progress has been made in developing portable microcoil-based NMR systems, devices that provide improved SNR, throughput, capabilities, and other benefits would be of great value to the art.

SUMMARY OF THE INVENTION

In a first aspect, the present invention provides modules, comprising:
(a) a microcoil possessing an inner diameter of between 25 microns and 550 microns;
(b) a conduit disposed proximate to the microcoil, wherein the conduit is in fluid communication with a sample reservoir;
(c) an affinity column in fluid communication with the conduit and the sample reservoir; and;
(d) a connector for connecting the module to a magnetic resonance detector.

In a second aspect, the present invention provides modules comprising:
(a) a plurality of microcoils each possessing an inner diameter of between 25 microns and 550 microns;
(b) a conduit disposed proximate to each microcoil, wherein the conduit is in fluid communication with a sample reservoir; and
(c) a connector for connecting the module to a magnetic resonance detector.

In a third aspect, the present invention provides microcoils comprising an inner diameter of between 25 microns and 550 microns, wherein the microcoil is an effective magnetic resonance transmitter or receiver coil; and wherein the microcoil is within or surrounds an affinity column.

In a fourth aspect, the present invention provides detection devices comprising
(a) a permanent magnet possessing a field strength of less than or equal to 4 Tesla;
(b) a microcoil disposed proximate to a magnetic field generated by the permanent magnet, wherein the microcoil possesses an inner diameter of between 25 microns and 550 microns;
(c) a conduit disposed proximate to the microcoil, wherein the conduit is in fluid communication with a sample reservoir;
(d) an affinity column in fluid communication with the conduit and the sample reservoir.

In a fifth aspect, the present invention provides detection devices comprising (a) a permanent magnet possessing a field strength of less than or equal to 4 Tesla;
(b) a plurality of microcoils each possessing an inner diameter of between 25 microns and 550 microns, wherein each microcoils is an effective magnetic resonance transmitter or receiver coil; and
(c) a conduit disposed proximate to each microcoil, wherein the conduit is in fluid communication with a sample reservoir.

In a sixth aspect, the present invention provides magnetic resonance detectors, comprising
(a) a housing comprising a conduit guide;
(b) a permanent magnet possessing a field strength of less than or equal to 4 Tesla within the housing; and
(b) the module of any embodiment of any of aspect of the invention, wherein the connector connects the module to the housing via the conduit guide.

In a seventh aspect, the present invention provides methods for detecting a target is a sample fluid, comprising:
(a) flowing a fluid containing one or more magnetically labeled targets through the conduit of the detection device of any embodiment of any aspect of the invention;
(b) energizing the microcoil at a frequency that permits detection of a magnetic resonance within the sample fluid; and
(c) processing a signal received from the microcoil to detect the magnetically labeled targets in the sample fluid.

In an eighth aspect, the present invention provides methods for detecting a target in a sample fluid, comprising:
(a) introducing a sample fluid into a sample reservoir, wherein the sample reservoir is in fluid communication with a conduit;
(b) flowing the sample fluid into an affinity column in the conduit, wherein the affinity column comprises one or more capture agents that bind to one or more targets of interest;
(c) flowing a fluid comprising magnetic particles into the affinity column, wherein the magnetic particles are capable of binding selectively to the one or more targets of interest bound to the affinity column via the one or more capture agents, and wherein binding of the magnetic particles to the targets produces magnetic particle-target complexes;
(d) washing the affinity column to reduce the number unbound magnetic particles;
(e) eluting bound magnetic particle-target complexes from the affinity column;
(f) flowing the fluid comprising the magnetic particle-target complexes through a conduit disposed proximate to a microcoil, wherein the microcoil possesses an inner diameter of between 25 microns and 550 microns, wherein the microcoil is an effective magnetic resonance transmitter or receiver coil; and
(g) energizing the microcoil at a frequency that permits detection of a magnetic resonance within the sample fluid; and
(h) processing a signal received from the microcoil to detect magnetic particle-target complexes in the sample fluid.

In a ninth aspect, the present invention provides methods for detecting a target in a sample fluid, comprising:
(a) introducing a sample fluid into a sample reservoir, wherein the sample reservoir is in fluid communication with a conduit, wherein the conduit is disposed proximate to a microcoil, wherein the microcoil possesses an inner diameter of between 25 microns and 550 microns, wherein the microcoil is an effective magnetic resonance transmitter or receiver coil;
(b) flowing the sample fluid into an affinity column in the conduit, wherein the affinity column comprises two or more layers, wherein each layer comprises one or more capture agents that bind to one or more targets of interest in the sample fluid, wherein each layer in the affinity column is capable of binding to molecules distinct from other layers; and wherein the affinity column is located at least partially within the microcoil;

(c) flowing a fluid comprising magnetic particles into the affinity column, wherein the magnetic particles are capable of binding selectively to the one or more targets of interest, and wherein binding of the magnetic particles to the targets produces magnetic particle-target complexes;

(d) energizing the microcoil at a frequency that permits detection of a magnetic resonance within the affinity column; and (e) processing a signal received from the microcoil to detect magnetic particle-target complexes in one or more layers of the affinity column.

In a tenth aspect, the present invention comprises methods for detecting a sample in a target fluid, comprising:

(a) mixing a sample fluid with magnetic particles capable of binding to the one or more targets of interest in the sample fluid, wherein binding of magnetic particles to targets produces magnetic particle-target complexes (b) introducing the sample fluid into a sample reservoir, wherein the sample reservoir is in fluid communication with a conduit, wherein the conduit is disposed proximate to a microcoil, wherein the microcoil possesses an inner diameter of between 25 microns and 550 microns;

(c) flowing the sample fluid into an affinity column in the conduit, wherein the affinity column comprises two or more layers, wherein each layer comprises one or more capture agents that bind to one or more targets of interest, wherein each layer in the affinity column is capable of binding to molecules distinct from other layers; and wherein the affinity column is located at least partially within the microcoil;

(d) energizing the microcoil at a frequency that permits detection of a magnetic resonance within the affinity column; and (e) processing a signal received from the microcoil to detect magnetic particle-target complexes in one or more layers of the affinity column.

In an eleventh aspect, the present invention provides methods for detecting a target in a sample fluid, comprising:

(a) introducing a sample fluid into a sample reservoir, wherein the sample reservoir is in fluid communication with a conduit, wherein the sample fluid comprises magnetic particles capable of binding selectively to one or more targets of interest in the sample fluid, and wherein binding of magnetic particles to targets produces magnetic particle-target complexes;

(b) flowing the sample fluid through the conduit disposed proximate to a microcoil, wherein the microcoil possesses an inner diameter of between 25 microns and 550 microns;

(c) energizing the microcoil at a frequency that permits detection of a magnetic resonance within the sample fluid;

(d) processing a signal received from the microcoil to detect magnetic particle-target complexes in the sample fluid;

(e) flowing a portion of the flowing fluid in which the labeled entity was detected through a conduit disposed proximate to a secondary microcoil;

(f) energizing the secondary microcoil at a frequency that permits detection of a magnetic resonance within the sample fluid; and (g) processing a signal received from the secondary microcoil to determine a further property of the magnetic particle-target complexes.

In a twelfth aspect, the present invention provides methods for detecting a target in a sample fluid, comprising:

(a) introducing a sample fluid into a sample reservoir, wherein the sample reservoir is in fluid communication with a conduit, wherein the sample fluid comprises magnetic particles capable of binding selectively to one or more targets of interest in the sample fluid, and wherein binding of magnetic particles to targets produces magnetic particle-target complexes;

(b) flowing the sample fluid through the conduit disposed proximate to a microcoil, wherein the microcoil possesses an inner diameter of between 25 microns and 550 microns;

(c) energizing the microcoil at a frequency that permits detection of a magnetic resonance within the sample fluid;

(d) processing a signal received from the microcoil to detect magnetic particle-target complexes in the sample fluid;

(e) diverting a portion of the flowing fluid in which the magnetic particle-target complexes were detected into a sequestration chamber to produce a concentrated target solution.

In a thirteenth aspect, the present invention provides methods for detecting a target in a sample fluid, comprising:

(a) introducing a sample fluid into a sample reservoir, wherein the sample reservoir is in fluid communication with a conduit, wherein the sample fluid comprises two or more targets of interest, and wherein the sample fluid comprises magnetic particles differentially bound to the two or more targets of interest to create at least a first magnetic particle-target complex and a second magnetic particle-target complex;

(b) flowing the sample fluid through the conduit disposed proximate to a microcoil, wherein the microcoil possesses an inner diameter of between 25 microns and 550 microns;

(c) energizing the microcoil at a frequency that permits detection of a magnetic resonance within the sample fluid; and (d) processing a signal received from the microcoil to differentially detect the at least first magnetic particle-target complex and the second magnetic particle-target complex in the flowing fluid.

All aspects and embodiments of the methods of the present invention can be carried out using the modules, microcoils, and detection devices of any embodiment of any aspect of the invention, of the invention.

DETAILED DESCRIPTION OF THE INVENTION

Figure 1:
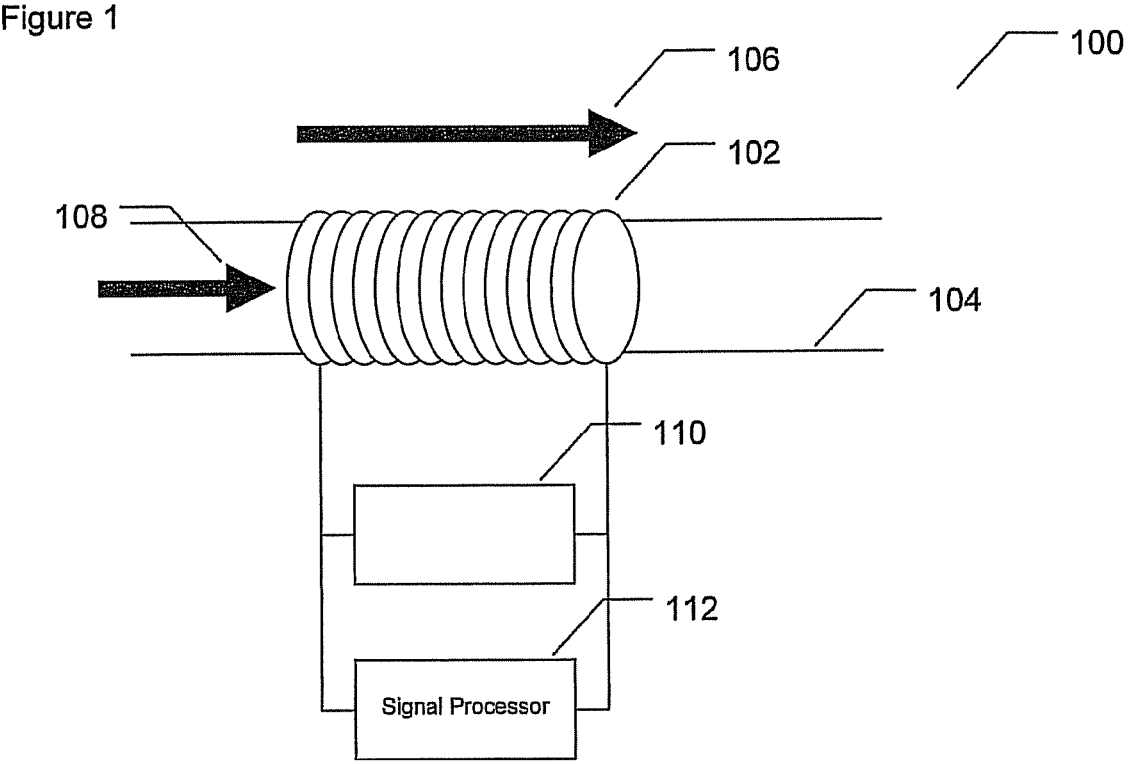
FIG. 1 depicts a portion of a detector in accordance with an embodiment of the present invention.

In a first aspect, the present invention provides modules, comprising:

(a) a microcoil possessing an inner diameter of between 25 microns and 550 microns;

(b) a conduit disposed proximate to the microcoil, wherein the conduit is in fluid communication with a sample reservoir;

(c) an affinity column in fluid communication with the conduit and the sample reservoir; and;

(d) a connector for connecting the module to a magnetic resonance detector.

In a second aspect, the present invention provides modules comprising:

(a) a plurality of microcoils each possessing an inner diameter of between 25 microns and 550 microns;

(b) a conduit disposed proximate to each microcoil, wherein the conduit is in fluid communication with a sample reservoir; and (c) a connector for connecting the module to a magnetic resonance detector.

In a third aspect, the present invention provides microcoils comprising an inner diameter of between 25 microns and 550 microns, wherein the microcoil is an effective magnetic resonance transmitter or receiver coil; and wherein the microcoil is within or surrounds an affinity column.

In a fourth aspect, the present invention provides detection devices comprising (a) a permanent magnet possessing a field strength of less than or equal to 4 Tesla;

(b) a microcoil disposed proximate to a magnetic field generated by the permanent magnet, wherein the microcoil possesses an inner diameter of between 25 microns and 550 microns;

(c) a conduit disposed proximate to the microcoil, wherein the conduit is in fluid communication with a sample reservoir;

(d) an affinity column in fluid communication with the conduit and the sample reservoir.

In a fifth aspect, the present invention provides detection devices comprising (a) a permanent magnet possessing a field strength of less than or equal to 4 Tesla;

(b) a plurality of microcoils each possessing an inner diameter of between 25 microns and 550 microns, wherein each microcoils is an effective magnetic resonance transmitter or receiver coil; and (c) a conduit disposed proximate to each microcoil, wherein the conduit is in fluid communication with a sample reservoir.

In a sixth aspect, the present invention provides magnetic resonance detectors, comprising (a) a housing comprising a conduit guide;

(b) a permanent magnet possessing a field strength of less than or equal to 4 Tesla within the housing; and (b) the module of any embodiment of any of aspect of the invention, wherein the connector connects the module to the housing via the conduit guide.

The modules, microcoils, detection devices and magnetic resonance detectors of the various aspects and embodiments of the present invention provide, for example, increased functionality and detection modes, improved sensitivity and specificity, time and cost savings, and a variety of other benefits including those described below.

All of the various embodiments for different components of the modules, microcoils, and detection devices of the first through sixth aspects of the invention are capable of use together; thus, any embodiment disclosed for one aspect can be combined with any embodiment for another aspect, as will be understood by those of skill in the art.

The modules of the invention can be used, for example, to couple disposable components of any embodiment detectors of the invention to permanent detector components by connecting the module to the detector via, for example, the conduit guide as discussed herein. In one example, all fluidic components of the detector are located on the module, thus reducing the probability that portions of a fluid sample will leak into the permanent detector components. Multiple modules may be used with a single detector, for example, to reduce the probability of contamination between detection experiments. In one embodiment, different sample fluids can be assigned their own modules which thus do not come in contact with other test samples. Removable modules also permit the conduit and microcoil characteristics to be adjusted based on the sample fluid used, or other aspects of a detection experiment. For example, a longer microcoil may be used in one experiment. In another example, a larger-diameter conduit may be used.

To provide structural support or make the module easier to handle, the module may be disposed on a surface, such as a card or board for example, or the removable module may be disposed in a housing. However, no support or housing means are necessary. For example, the module may comprise a section of a conduit with a solenoidal microcoil wrapped around a portion of the conduit. An exemplary module is provided in FIG. 8.

In an example detector, the module can slide into the detector on conduit guides that place the conduit and the microcoil in a uniform region the field generated by the permanent magnet. The microcoil can be mounted directly on the conduit, and electrical leads extending from the microcoil can extend to electrical contact pads or connector on an edge of the module. Any other fluidic channels that are used in the course of the detection experiment can also be contained on the module. The conduit guides also place the module in a selected alignment with the magnetic gradient coil and a vacuum fluidic drive.

One embodiment of the detector includes a test box and a disposable module. The box may comprise the magnet, detection circuitry and interface, fluidic driver and controls, user interface, result printer, interface to the clinical data base, module ID reader, conduit guide, master processor system and software, and other associated power supplies and supporting electronics.

As used herein, an "affinity column" comprises any means to trap a target entity capable of separating biochemical mixtures based on specific interactions with a target, including but not limited to antigen-antibody interactions; enzyme-substrate interactions; and receptor-ligands interactions. The affinity column for use in the devices and methods of the invention may comprise the "stationary phase" (the specific substance, or resin, used to separate analytes) within the conduit, may comprise a separate affinity column placed in the conduit (the stationary phase and column hardware), or any other suitable variations thereof.

An affinity column may be used with the modules of the invention to trap a target entity and permit the target entity to be labeled with a labeling bead, such as a magnetic label. Any affinity column capable of separating biochemical mixtures based on specific interactions with a target can be used. For example, one or more affinity columns may comprise a capture agent to immobilize a target entity in a sample fluid as a way to concentrate the fluid prior to flowing the fluid through a detection zone of the conduit. A "capture agent" is any molecule capable of selectively binding, or being derivatized to selectively bind, a target of interest in the sample fluid. Suitable capture agents include, but are not limited to, proteins, nucleic acids, antibodies, lectins, enzymes, mono-, or poly-saccharides. The capture agent can be attached to the column packing material using a linker which binds to the column through a reversible binding reaction. For example, a hexa-histidine linker will bind to Ni or Co ions attached to a Ni-, or Co-nitriloacetate-agarose column matrix. The binding of the linker to the column can be reversed through competition with a release agent, such as histidine or imidazole, in the case of a hexa-his linker. This linker is covalently attached to the recognition molecule via standard chemical methods.

This use of affinity columns provides a "pre-filter" for the detection device, and can be used to both concentrate the targets and remove excess unbound labeling beads. For larger samples, or samples suspected of having low concentrations of targeted entities, the use of a concentrating mechanism such as an affinity column may facilitate a reduction in the sample volume. For example, an environmental sample of 50 milliliters may be suspected of containing low concentrations of a target entity. To speed up the detection process, an affinity column with a labeled capture agent capable of selectively binding to the target entity may be used to isolate and hold the target entity while the remainder of the sample is washed away. After the extraneous portion of the sample is removed, and carrier fluid can be passed through the affinity column to carry the previously trapped target entities into the sensitive volume of the detector.

Alternatively, unlabeled target entities may be trapped by a capture agent on a solid phase, such as in an affinity column or other column known from chromatography. Once attached to the affinity column and immobilized, a solution of labeled beads with attached antibodies selective for the target entities may be introduced so that all of the attached targets are labeled with beads. The excess beads that do not label any target may then be washed out of the column. The targets, with their labels attached, may then be eluted from the column and this eluant can then be processed by the NMR detector.

In another embodiment, the affinity column comprises two or more layers (2, 3, 4, 5, 6, 7, 8, 9, 10, or more layers), and wherein each layer comprises a different capture agent, which can be used to trap different targets in different regions of space in the column, which can be detected differentially using multiple NMR detectors or MRI techniques, as described in more detail below. In one embodiment, overall magnetic resonance signal changes are first detected, and then MRI techniques are used to identify which of the affinity column layers is the source of the change.

In another embodiment, the microcoil is integrated into the affinity column (ie: within or surrounds the affinity column). Affinity columns can be made very small and typically contain substances that can produce NMR signals. Thus, a microcoil can be built into (or around) a column so that it can directly detect targets trapped inside; for example, the microcoil can be wound around the affinity column, or embedded in its walls. A stationary magnetic target can be detected many times, confirming the positive detection. Different protocols can be applied to a target of known location, improving detection accuracy and precision, allowing more definitive detection, differential detection, etc. The integrated detector coil eliminates the need for a separate elution step, which reduces time, target damage, stripping of magnetic labels from the targets, dilution of targets into a larger elution volume, spreading of targets through diffusive processes into a larger region of sample volume, etc.

The column material itself can be chosen so as to contribute to the NMR signal, including that part of the signal affected by the presence of a magnetic target. For example, the material can be a gel, or any other material that is stationary but also provide a liquid-like NMR signal. In one embodiment, the material can contain hydrogen or fluorine atoms sufficient to produce a detectible NMR signal. The material may also be a solid material containing aluminum or any other atom that produces a sufficiently liquid-like NMR signal, for example from the central transition of its quadrupole-perturbed NMR spectrum. The column material can be modified ("liquefied") so that it contributes to the detected NMR signal. For example, the column material may be initially a solid that produces no usable NMR signal, but can be transformed so that it produces a usable liquid-like signal through the action of chemicals or the changing of the temperature. In the extreme case, the column material may be dissolved through the use of an appropriate solvent. The column material can be chosen so that it does not alter the magnetic field being applied to the sample space (i.e., the column's stationary phase can be chosen so that it has the same magnetic susceptibility as the fluid). For example, the column material can be a glass, ceramic, or gel that contains an appropriate admixture of impurities, such as paramagnetic ions (Cu, Mn, Gd), so that the materials overall magnetic properties match those of the sample fluid being processed. The impurities to be mixed and their concentration can be chosen so that the presence of the column material does not degrade the homogeneity of the magnetic field in the column.

In another embodiment, the solid phase of the affinity column can chosen so that it can be dissolved and the column contents passed through the detector, eliminating the need for elution and allowing more of the column itself to contribute to the NMR signal. For example, the dissolving can be achieved through the use of a solvent chosen to dissolve the solid phase, or by changing the temperature of the column in a way that renders the solid phase a liquid (such as raising the temperature to melt the solid phase). The dissolution need not be complete and the solid phase may simple break apart in to pieces that are small enough to pass through the NMR detection coil.

In another embodiment, a plurality of different affinity columns can be used, in parallel, or more preferably in series, in order to attach a particular pathogen type in each separate column.

The detectors of the invention comprise a microcoil disposed proximate to the magnetic field generated by the permanent magnet, wherein the microcoil possesses an inner diameter between 25 microns and 550 microns. The microcoil is an effective magnetic resonance transmitter or receiver coil. In various embodiments, the inner diameter of the microcoil can be between 25-500, 25-450, 25-400, 25-350, 25-300, 25-250, 25-200; 50-550, 50-500, 50-450, 50-400, 50-350, 50-300, 50-250, 50-200, 100-550, 100-500, 100-450, 100-400, 100-350, 100-300, 100-250, 148-648, 170-555, and 100-200 microns. In an example detector, the microcoil is solenoidal in shape and can be wound around a section of a conduit that holds the volume of fluid during a detection experiment. However, other coil shapes may be used, including but not limited to planar coils, rectangular coils, saddle coils, and meanderline coils. For example, the cylindrical axis a flat or a solenoidal microcoil may be capable of being oriented perpendicularly to the axis of a conduit, and the coil may be filled with a material, for example but not limited to, ferrites, to enhance the sensitivity of the coil. Further, the microcoil may be formed through other construction techniques, including but not limited to depositing the coil material on a surface or etching the coil. The length of the microcoil can be selected such that the length of the microcoil is coextensive with the uniform region of the magnetic field generated by the permanent magnet of the detection devices of the invention. Other lengths may also be selected. In various embodiments, the length of the microcoil is between 25 μm-5 cm, 50 μm-5 cm, 75 μm-5 cm, 100 μm-5 cm, 100 μm-4 cm, 100 μm-3 cm, 100 μm-2 cm, 100 μm-1.5 cm, 100 μm-1 cm, 1.5 mm-1.5 cm, 2.0 mm-1.5 cm, 3 mm-1.5 cm, 4 mm-1.5 cm, 5 mm-1.5, 6 mm-1.5 cm, 7 mm-2 cm, 8 mm-1.5 cm, and 9 mm-1 cm. Generally, the strength of the signal produced by a microcoil increases with the length of the coil. Some detectors may include a multiplicity of differently-sized microcoils. In an example detector, a first microcoil with a larger inner diameter is used to conduct an initial analysis of a sample. If the presence of an entity in a fluid is detected by the first microcoil, the fluid may be diverted to be analyzed at a higher sensitivity by a second microcoil with a smaller inner diameter.

As used herein, the microcoil being "disposed proximate to the magnetic field" means that at least a portion of the microcoil is located within the magnetic field produced by the permanent magnet. In an example detector, the entire coiled section of a solenoidal microcoil is placed within a magnetic field and oriented such that the magnetic field observed at all points on the coiled section of the solenoidal microcoil is uniform. However, any orientation of the microcoil within the magnetic field may be used, for example an orientation that aligns the microcoil with a non-zero component of the magnetic field in order to employ MRI techniques. For example, the microcoil may be angled with respect to the direction of the magnetic field, and portions of the microcoil, such as the ends or the electrical leads from the microcoil, may extend beyond the magnetic field.

In one embodiment, the microcoil is a closely wound microcoil, with a total length according to any embodiment of the invention, including ranges between 100 μm and 1500 μm, 100 μm and 1100 μm, or any range in between. In another embodiment, the microcoil or closely wound microcoil is wound around a capillary with an outer diameter of and/or an inner diameter as discussed below. In another embodiment, the microcoil comprises wire with a diameter less than or equal to 2.5 times a skin-depth of the wire material.

The microcoil is capable of being energized at a frequency that permits detection of a magnetic resonance within a volume of fluid within the conduit based on the strength of the magnetic field generated by the permanent magnet. The frequency that permits detection of a magnetic resonance within a volume of fluid varies with the strength of the magnetic field such that $f=\gamma'B$, where f is the frequency, B is the magnetic field strength, and $\gamma'$ is a proportionality constant based on the nuclei examined within the fluid. For example, $\gamma'$ for the nuclei of hydrogen atoms is approximately 42.6 MHz/Tesla. In various examples, the frequency that permits detection of a magnetic resonance with in a volume of fluid in the conduit is between 1-100, 10-100, 20-100, 30-100, 40-100, 50-100, 60-100, 70-100, 80-100, 90-100, 20-85, 30-85, 40-85, 50-85, 60-85, 70-85, 80-85, 20-65, 30-65, 40-65, 60-65, and 35-45 MHz.

It is possible to provide for additional throughput by using two, or more, microcoil sections in parallel in the modules and/or detectors of the invention, in order to enhance throughput of sample fluids. This may be optimized by the use of MRI techniques, such that the signal from a particular coil may be discerned by the characteristics of the signal, for example frequency content of frequency characteristic. For example, magnetic field gradients (discussed below), applied at the appropriate angle oblique to the microcoils, separate the signals from each coil into its own unique frequency range, allowing simultaneous signal acquisition from all coils. Alternatively, or additionally, each coil may be electrically connected individually, and the signal processed in a separate electronic channel.

In any embodiment of any aspect of the present invention, the microcoil may be part of a resonant circuit, comprising:
 (a) the microcoil;
 (b) an auxiliary inductor coil electrically connected in series to the microcoil; and
 (c) a tuning capacitor electrically connected to the microcoil and the auxiliary inductor coil to form a resonant circuit.

In various preferred embodiments, the microcoil is a closely wound microcoil and/or comprises wire with a diameter less than or equal to 2.5 times a skin-depth of the wire material.

Resonant circuits of all aspects and embodiments of the present invention allow for the design and production of improved microcoil NMR devices that provide, for example, improved SNR and line width performance as well as increased functionality as described in detail herein, and thus greatly improve detection capabilities, and also allow further reductions in sample volume and further miniaturization of microcoil NMR devices than was possible in prior methods and devices. In various embodiment of the resonant circuits, the microcoil or closely wound microcoil has a total length as disclosed in any of the embodiments herein. In another embodiment of the resonant circuits, the microcoil or closely wound microcoil is wound around a capillary with an outer diameter and/or an inner diameter as disclosed in any of the embodiments herein. In a further embodiment of the detector aspects of the invention, the auxiliary or tuning inductor comprises wire of a larger diameter than a diameter of the microcoil or closely wound microcoil wire. In a still further embodiment of the resonant circuits of the invention, the auxiliary or tuning inductor coil has a radius of 0.3 cm to 0.6 cm. In another embodiment, the resonant circuits are mounted on a mechanical support; when mounted on a mechanical support, the resonant circuit may be installed in one or more shielded probe bodies.

In one embodiment, the one or more shielded probe bodies comprise two shielded probe bodies, wherein a first shielded probe body shields the closely wound microcoil, wherein a second shielded body shields the shielded probe body and/or shields the auxiliary inductor and the capacitor. Each of these embodiments can be used in combination with other embodiments of all the aspects of the invention, as well as further aspects of the invention that involve use of the resonant circuits.

Any conduit capable of receiving a fluid sample may be used, including but not limited to a capillary tube. In one embodiment, the conduit is hollow and cylindrical in shape, with the inner and outer diameters sized to accommodate picoliter-microliter volumes within the sensitive volume of the detector. The inner diameter of the conduit may be selected based on the properties of the fluid used in a detection experiment, as well as other parameters of a detection experiment such as the strength of the signal produced by a fluid, the flow rate of the fluid, and the desired resolution of the experiment, for example. The conduit has an inner diameter between 25 and 550 microns. In various embodiments, the conduit inner diameter can be between 25-500, 25-450, 25-400, 25-350, 25-300, 25-250, 25-200; 50-550, 50-500, 50-450, 50-400, 50-350, 50-300, 50-250, 50-200, 100-550, 100-500, 100-450, 100-400, 100-350, 100-300, 100-250, 170-550, and 100-200 microns. The outer diameters can be any that may suitably be used with conduits of the inner diameters disclosed herein. Further, in embodiments where the microcoil is used to retain the fluid (microcoil forms the conduit), the wall thickness of the conduit may be reduced to zero. The efficiency of the detector may be improved by reducing the difference between the inner and outer diameters of the conduit. An example conduit is a capillary tube with an inner diameter of 100 microns and an outer diameter of 170 microns. Conduits conforming to different shapes may also be used, including but not limited to elliptical conduits. Further, the conduit may comprise multiple sections, and may include removable sections. Removable sections, for example, may facilitate a reduction in the probability of a contamination of a sample or may permit the device to be more readily cleaned or repaired. The conduit itself may be disposed on the conduit guide, either directly placed thereon or indirectly with another component serving to guide the conduit into the conduit guide. In one embodiment, the conduit is disposed on a module, discussed in more detail herein, that the conduit guide is capable of receiving.

The conduit can receive fluid from any suitable component, including but not limited to a reservoir for providing fluid to the conduit. Such a reservoir can be on board the device or on the module discussed herein. The reservoir can simply be a component of the conduit in which a valve is placed to control flow from the reservoir to the portion of the conduit used for analysis.

As used herein, the conduit being "disposed proximate to the microcoil" means any position from which a signal transmitted from the microcoil can reach the conduit and the corresponding energy released from the fluid in the sensitive volume of the conduit can induce an electrical current in the microcoil. In an example embodiment, a solenoidal microcoil is wrapped around the conduit, such that the axis of the microcoil is parallel with the axis of the conduit. In another example, a planar coil is located immediately adjacent to the conduit and oriented such that the center axis of the planar coil is perpendicular with the center axis of the conduit.

Further, the conduit may comprise a plurality (ie: 2, 3, 4, 5, 6, 7, 8, 9, 10, 50, 100, or more) of branches capable of receiving a volume of fluid. The plurality of branches may be disposed proximate to a plurality of microcoils. In one embodiment, each branch is disposed proximate to a separate microcoil, where each branch and each microcoil may be the same or have different sizes as deemed appropriate for the specific use. For example, the plurality of branches may permit the division of a fluid sample into multiple subsamples, or may permit assaying of more than one fluid sample at a time. In a further embodiment, one or more branches of the conduit are used in other fluidic processes. For example, one or more branches may be fluidically coupled to one or more affinity columns. In experiments that use labeling beads to aide in the identification of entities in a fluid, different labels may be added to each of the subsamples. The plurality of branches may also be coupled to valves, sequestration chambers, and/or other fluidic structures as suitable for a given purpose. Such fluidic components can be "on board" the detector, or may be provided via a removable module, such as one that can be connected to the conduit guide.

The detectors of any embodiment of any aspect of the present invention may comprise a conduit guide capable of receiving a conduit for receiving fluid, wherein the conduit guide is capable of disposing the conduit proximate to the microcoil and proximate to the magnetic field generated by the permanent magnet (and proximate to the magnetic gradient when the detector is in use). The conduit guide may comprise any means for orienting the conduit, including but not limited to mounting brackets, mechanical guides, and couplings. The conduit guide can be made from any material or materials that are capable of establishing and maintaining the position of the conduit guide. For example, metals, plastics, composite materials, ceramics, and multi-layer materials can be used individually or in combination to form the conduit guide. In an example detector, the conduit guide also aligns the axis of the portion of the conduit that holds the sample fluid (sensitive volume) during an experiment with the direction of the magnetic gradient produced by the magnetic gradient generator. In another example detector, the conduit guide is adjustable to permit an operator to select a position of the conduit relative to the magnetic gradient that minimizes a frequency shift in a signal emitted by the sensitive volume when the magnetic gradient is energized. In embodiments that utilize a coil as a magnetic gradient generator, the conduit guide may align the long axis of a cylindrical conduit with the center of the gradient coil. However, the conduit guide may dispose the conduit in other positions and orientations as deemed appropriate by an operator.

The module comprises a connector for connecting the module to a detector, such as those disclosed herein. Any connector capable of coupling the module to a detector may be used. For example, any of the conduit guides described as part of the detector or method aspects of the present invention may be used. Further, any mechanical coupling capable of securing the module in place may be used. For example, a connector where threaded screws or bolts on the module were coupled to corresponding threaded holes on the detector may be used. Other example connectors include mechanical clips, snap fittings, mortise-and-tenon connections, pins, socket fittings, and compression fittings.

The module may further comprise electrical contacts capable of establishing an electrical connection between the microcoil or the module and the detector of any embodiment of the invention. The electrical connection between the removable module and the detector may permit the microcoil to interface with a tuning circuit, signal processor, or any other circuitry on a detector, such as those disclosed herein. In removable modules that contain electronics such as signal generators, signal processors, tuning circuits and other electronics on the removable module, the electrical connection between the removable module and the detector may permit any of the electronic components on the removable module to interface with electrical components within the detector. For example, the electrical connection can be used to supply power to the removable module or allow the removable module to connect to a user interface. Any means of establishing an electrical connection may be used. For example, wire leads coupled to the microcoil may extend from the module. In embodiments where the microcoil is electrically connected to the module, conductive traces may establish a connection between the microcoil and an electrical coupling on the module, which may be inserted into a receptacle on a detector.

The module may further comprise a fluidic drive fluidically coupled to the conduit. Any suitable fluidic drive may be used with the module. The modules and detectors of any embodiment of any aspect of the invention may further comprise a fluidic drive, capable of being fluidically coupled to the conduit. The fluidic drive may permit the purposeful diving of a fluid in the conduit. Typically, the fluidic drive operates by applying a change in the pressure on one end of the conduit. For example, a vacuum may be attached to one end of the conduit to draw the fluid through a portion of the conduit. A positive displacement pump, such as a syringe pump may also be used to establish fluid flow. The fluid drive may also use air pressure or gravity to drive the fluid. Any device that is capable of imparting a flow to a fluid in the conduit may be used. The fluidic drive can be "on board" the detector, or may be provided via a removable module, such as one that can be connected to the conduit guide (described in more detail herein).

Other fluidic components that may be fluidically coupled to the conduit, such as valves, sequestration chambers, and affinity columns may also be included on the removable module and/or the detector. Any valve that is capable of being fluidically coupled to a portion of the conduit may be used with the modules of the invention. A valve may allow the flow of a fluid in the conduit to be controlled. For example, in modules with conduits that contain a plurality of branches, one or more valves may be used to sequence the flow of a fluid through the plurality of branches. A sequestration chamber (which may be, for example, a well on a microplate, a separate conduit branch, a reservoir, etc.) may be used to hold a portion of a fluid used in a detection experiment. For example, a valve may be used to divert a portion of the fluid into a sequestration chamber if an entity is detected in the fluid. Any volume sequestration chamber may be used. For example, a small volume of a few nanoliters may be enough to allow for a subsequent microscopic evaluation of the fluid in which target is detected. In another example, several microliters, or even the entire volume of a sample fluid may be held in the sequestration chamber.

The detectors of the invention comprise a permanent magnet. The permanent magnet possesses a field strength, wherein the field strength is less than or equal to 4 Tesla. In various embodiments, the field strength may be between 0.1-4, 0.1-3.8, 0.1-3.6, 0.1-3.4, 0.1-3.2, 0.1-3.0, 0.1-2.8, 0.1-2.6, 0.1-2.4, 0.1-2.2, 0.1-2, 0.1-1.9, 0.1-1.8, 0.1-1.7, 0.1-1.6, 0.1-1.5, 0.1-1.4, 0.1-1.3, 0.1-1.2, 0.1-1.1, 0.1-1.0, 0.25-4.0, 0.25-3.5, 0.25-3.0, 0.25-2.5, 0.25-2, 0.25-1.9, 0.25-1.8, 0.25-1.7, 0.25-1.6, 0.25-1.5, 0.25-1.4, 0.25-1.3, 0.25-1.2, 0.25-1.1, 0.25-1.0, 0.5-2, 0.5-1.9, 0.5-1.8, 0.5-1.7, 0.5-1.6, 0.5-1.5, 0.5-1.4, 0.5-1.3, 0.5-1.2, 0.5-1.1, and 0.5-1.0 Tesla. The permanent magnet may be constructed out of a single magnet, or a plurality of permanent magnets may be combined. Further, any materials used in the construction of permanent magnets may be used to form the permanent magnet for the detector. For example, iron, other ferrous and non-ferrous alloys, ceramic magnetic materials, rare earth magnets including SmCo and NdFeB, and other magnetic materials may be used. The permanent magnet may also be formed into any shape. For example, magnets (or combinations of magnets) with curved, rectangular, cylindrical, or other profiles may be used. In an example detector, a dipole magnet with steel pole pieces is used as the permanent magnet. However, other magnets, such as Halbach magnets may also be used. In an example detector, the magnetic field produced by the permanent magnet is uniform. However, permanent magnets that form magnetic fields possessing gradients, such as the static gradients sometimes encountered when constructing magnets, may also be used in the detector. The slope of the gradient that may be present from the permanent magnet may range between 0 G/cm and 1.0 G/cm. In embodiments where the permanent magnet possesses a gradient, the gradient generated by the magnetic gradient generator differs in strength of type (for example, pulsed vs. static). The detector may also comprise a multiplicity of permanent magnets with a multiplicity of magnetic fields. In an example detector, two permanent magnets may be used, the first with a magnetic field strength of 2.0 Tesla, and the second with a magnetic field strength of 1.0 Tesla. The use of different magnetic field strengths during the course of a detection experiment may facilitate the detection of a variety of different entities with a fluid sample. Further, since the resonant frequency of the nuclei in a fluid varies with the field strength, the use of detectors with a multiplicity of field strengths may further reduce the likelihood of false positive or false negative detections by analyzing a fluid at more than one field strength and frequency.

In one further embodiment of any other embodiment of the invention, the module/detection device further comprises an NMR imaging system. Such imaging systems are known to those of skill in the art. In another embodiment, the module/detection device further comprises a matching capacitor in electrical connection to the resonant circuit, which connects the resonant circuit to the detection electronics of the device (ie: the NMR detection system).

In an embodiment of all aspects of embodiments of the invention, the detection devices disclosed herein may also comprise magnetic gradient generators and other components, such as a signal processor, to form a microcoil NMR-MRI system. In this embodiment, the microcoil(s) is/are disposed proximate to the magnetic gradient. The detectors of this embodiment comprise a magnetic gradient generator. The gradient is used to differentiate between a plurality of signal detection volumes within a microcoil. The gradient may also be used to compensate for a gradient in the magnetic field generated by the permanent magnet. Any magnetic gradient generator capable of applying a magnetic gradient to the magnetic field generated by the permanent magnet may be used, including but not limited to permanent magnets, superconducting electromagnets, or gradient coils. In an example detector, the magnetic gradient is linear, though any gradient may be used, including, but not limited to non-linear gradients. The gradient generator may generate gradients with slopes between 0.01 G/cm and 1.0 G/cm. In various embodiments, the slope of a localized area of the gradient generated by the magnetic gradient generator is between 0.01-1.0, 0.015-1.0, 0.02-1.0, 0.02-0.9, 0.02-0.8 0.02-0.7, 0.02-0.65, and 0.02-0.6 G/cm. As discussed herein, in embodiments where the permanent magnet possesses a gradient, the gradient generated by the magnetic gradient generator differs in strength of type (for example, pulsed vs. static). A static gradient is used in an example detector because static gradients are particularly compatible with miniaturized NMR and MRI platforms, and are relatively simple compared to other gradients. However, other gradient types may be used, including but not limited to pulsed gradients and combinations of pulsed and static gradients. The strength of the gradient used in a detector determines the spatial resolution of the detector. Increasing the strength of the magnetic gradient permits the detector to identify magnetic resonances in smaller sections of the microcoil. In an example detector, a magnetic gradient of 0.07 G/mm is used in conjunction with a microcoil that is 1.1 mm in length. Using the weakest gradient that still provides the desired spatial resolution may facilitate more narrow detection bandwidths and improved signal-to-noise characteristics of the detector. In an example detector, a magnetic gradient is selected based on the $T_2^*$ of the sample fluid, without changing the center frequency of the energy emitted by the sample fluid during a detection experiment is used. In an example detector, a first magnetic gradient of approximately 0.14 G/mm may be applied during a first analysis of a sample. If the results of the analysis are inconclusive, or if improved signal-to-noise characteristics are desired, a second gradient of 0.07 G/mm may be applied during a second analysis of the same sample. The detectors of this embodiment may further comprise a signal processor electrically coupled to the microcoil and capable of identifying a plurality of frequency components and a plurality of magnitude components within the signal received from the microcoil, and capable of correlating the plurality of magnitude components and plurality of frequency components to a presence or absence of an entity in a volume of fluid at a plurality of locations along an axial length of the conduit. The signal processor may use any method for identifying frequency components and magnitude components within a signal. In an example detector, the signal processor is capable of performing a fast Fourier transformation on the signal received from the microcoil to identify a plurality of frequency components and a plurality of magnitude components within the signal from the microcoil.

As used herein, the microcoil being "disposed proximate to the magnetic gradient" means that at least a portion of the microcoil is placed within the magnetic gradient generated by the magnetic gradient generator. In an example detector, the microcoil is located within the magnetic gradient and oriented such that the axis of the microcoil is aligned to be parallel to the direction of a linear magnetic gradient. However, any orientation of the microcoil with respect to the gradient that aligns the microcoil with a non-zero component of the magnetic gradient may be used. As will be understood by those of skill in the art based on the teachings herein, disposition of the microcoil proximate to the gradient and proximate to the magnetic field are separate variables in design of the detectors of the invention.

The modules and detectors of any embodiment of any aspect of the invention may further comprise a tuning circuit electrically coupled to the microcoil. The tuning circuit comprises a tuning coil capable of having an inductance at least two times larger than the inductance of the microcoil, and a capacitor coupled to the tuning coil to form a resonant circuit. In various embodiments, the tuning coil may have an inductance that is 3, 4, 5, 6, 7, 8, 9, 10, 20, 25, 50, 100, 250, 500, or 1000 times larger than the inductance of the microcoil. The tuning circuit comprises a tuning coil that possesses an inductance of at least 2 nH, and the tuning coil is coupled to a capacitor to form a resonant circuit. In various embodiments, the inductor may have an inductance between 2 nH-1 µH, 10 nH-1 µH, 50 nH-1 µH, 100 nH-1 µH, 200 nH-1 µH and 500 nH-1 µH. The tuning coil may be coupled to the microcoil to form a series or a parallel connection with the microcoil. Such tuning coils can be "on board" the detector, may be provided via a removable module, such as one that can be connected to the conduit guide, or a combination thereof. Any method of coupling the microcoil to the tuning coil may be used, including but not limited to a transmission line between the microcoil and the tuning coil. An example tuning circuit is disclosed in U.S. Pat. No. 7,405,567, incorporated herein by reference. Such tuning coils can be "on board" the detector, may be provided via a removable module, such as one that can be connected to the conduit guide, or a combination thereof.

The tuning coil, which may also be referred to as an auxiliary inductor or a tuning inductor may be designed in accordance with a method comprising:

(a) preparing a microcoil with wire of a first diameter;
(b) determining an RF resistance of the microcoil;
(c) winding an auxiliary inductor coil with wire of a second diameter, where the second diameter is greater than the first diameter, and wherein a radius of the auxiliary inductor coil is determined using the formula:

$$r_{coil} = \sqrt{\frac{25 l_{wire} k d_{wire}}{46\pi}}$$

where $l_{wire}$ is the wire length, $d_{wire}$ is the wire diameter, and $kd_{wire}$ is the turn-to-turn wire spacing.

The detectors of any embodiment of any aspect of the present invention may further comprise a signal processor electrically coupled to the microcoil and capable of identifying a plurality of frequency components and a plurality of magnitude components within the signal received from the microcoil, and capable of correlating the plurality of magnitude components and plurality of frequency components to a presence or absence of an entity in a volume of fluid at a plurality of locations along an axial length of the conduit. The signal processor may use any method for identifying frequency components and magnitude components within a signal. In an example detector, the signal processor is capable of performing a fast Fourier transformation on the signal received from the microcoil to identify a plurality of frequency components and a plurality of magnitude components within the signal from the microcoil. The signal processor may comprise the computer programs disclosed herein.

In a further embodiment, the modules/detector may comprise physical computer readable storage media, for automatically carrying out the methods of the invention on a detector, such as those disclosed herein. As used herein the term "computer readable medium" includes magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or be distributed among multiple interconnected processing systems that may be local or remote to the processing system.

In a seventh aspect, the present invention provides methods for detecting a target is a sample fluid, comprising:

(a) flowing a fluid containing one or more magnetically labeled targets through the conduit of the detection device of any embodiment of any aspect of the invention;

(b) energizing the microcoil at a frequency that permits detection of a magnetic resonance within the sample fluid; and (c) processing a signal received from the microcoil to detect the magnetically labeled targets in the sample fluid.

The methods of the present invention allow direct detection of single cells, molecules, etc. in a given sample volume. The methods comprise moving a sample fluid through a detector and determining if an object of interest goes through, which are counted. Prior art detectors are sensitive to minimum concentrations of objects. It is especially unusual to use NMR to detect single objects, as traditional NMR detection techniques are low-sensitivity and require target numbers many times larger than a single cell or molecule.

The methods of the invention comprise energizing the microcoil at a frequency that permits detection of a magnetic resonance within the fluid. The microcoil is used to transmit a pulsed electromagnetic signal at a selected resonant frequency towards the fluid in the conduit. The frequency of the transmitted signal is selected based on the properties of the particular nuclei that are being examined in the detection experiment and the strength of the magnetic field. The microcoil is also used to detect the energy that is absorbed or released by the nuclei in the magnetic field in response to the transmission of the resonant frequency signal. This energy induces an electrical current in the microcoil that corresponds with the energy absorbed or released by the nuclei in the flowing fluid. The presence of an entity within the fluid causes a change in energy that can be detected by the microcoil.

Such forms of contrast can arise also from any other interactions of the labeled entity and the surrounding fluid. The general form of this interaction is due to the mismatch in magnetic property called susceptibility, between the entity and the carrier solution. Thus, in principle, the device being disclosed can also be sensitive to almost any distinct object including even bubbles. However, this effect scales with the strength of the magnetic field so it is not a large effect in our relatively low field permanent magnets especially compared to the magnetic particles that are chosen because of their strong magnetic strength, referred to as magnetic moments.

When the distortion in the uniform magnetic field in the vicinity of the object is a result of ferromagnetism or "superparamagnetism" of the object itself, the object is responding non-linearly to the uniform magnetic field, and hence it is not described as having a magnetic susceptibility. Instead, the object is described as having a magnetic moment, which may or may not be due to a saturation magnetization of the object. This magnetic particle disrupts the field homogeneity in its neighborhood, and this disruption may be detected by NMR methods.

The object disturbing the magnetic field in its vicinity may be much too small to be detected directly by NMR. The field disturbance may be effective over a volume very much larger than the object itself. If the volume of material affected by the object is large enough, then the presence of the object can be detected by NMR. In this sense, the magnetic field disturbance serves to amplify the NMR signal indicating the presence of the object.

The most basic form of NMR contrast is to detect whether something is present in the sample region or not. Using the methods of the present invention when a dilute solution containing labeled entities, for example, bacteria, is passed through the NMR detector, the labeled entities can be detected individually. The magnetic beads that label specific targets affect the NMR signal from the surrounding fluid adversely. Therefore, if the "sphere of influence" of the magnetic particles is comparable to the volume being examined, i.e., the "sphere" should span a significant fraction of the tube through which the solution is flowing, the NMR signal that arises from the total cross-section of the sample tube are attenuated. Protocols for excitation and detection may also be devised to highlight other properties of the sample fluids. Fluids may differ in how long they produce signals in response to an excitation, for example. These differences in "relaxation time" may be exploited to make a differential detection of the two (or more) fluids in a mixture. There are several different relaxation times, each appropriate to a particular method for exciting and detecting the atomic nuclei, and each related to different chemical or physical properties (or combination of properties). The most commonly discussed relation times are denoted $T_1$, $T_2$, and $T_2^*$. Many other parameters, including the diffusion tensor, flow velocity, elastic modulus, chemical environment, and temperature, can be encoded into the detected signal in an NMR experiment. It is also possible to combine the detection of more than one physical parameter into the same NMR experiment. It is common, for example, to combine both T2 detection and spatial location detection into a "T2-weighted image." In this case, the detected signal is affected by both the amount of material located at every position in space and the T2 of the material located there.

In an eighth aspect, the present invention provides methods for detecting a target in a sample fluid, comprising:

(a) introducing a sample fluid into a sample reservoir, wherein the sample reservoir is in fluid communication with a conduit;

(b) flowing the sample fluid into an affinity column in the conduit, wherein the affinity column comprises one or more capture agents that bind to one or more targets of interest;

(c) flowing a fluid comprising magnetic particles into the affinity column, wherein the magnetic particles are capable of binding selectively to the one or more targets of interest bound to the affinity column via the one or more capture agents, and wherein binding of the magnetic particles to the targets produces magnetic particle-target complexes;

(d) washing the affinity column to reduce the number unbound magnetic particles;

(e) eluting bound magnetic particle-target complexes from the affinity column;

(f) flowing the fluid comprising the magnetic particle-target complexes through a conduit disposed proximate to a microcoil, wherein the microcoil possesses an inner diameter of between 25 microns and 550 microns, wherein the microcoil is an effective magnetic resonance transmitter or receiver coil; and (g) energizing the microcoil at a frequency that permits detection of a magnetic resonance within the sample fluid; and (h) processing a signal received from the microcoil to detect magnetic particle-target complexes in the sample fluid.

The use of affinity columns as a filtering step before NMR detection can be used to concentrate the targets and/or remove the excess unbound labels. The sample fluid is pumped through a column in which a stationary phase of an affinity column is placed. The stationary phase is functionalized with one or more capture agents to preferentially trap the targets of interest. The sample fluid may be circulated through the column numerous times if useful in trapping all the targets. Once the column is loaded with one or more target types, a fluid containing the magnetic labels is flowed into the column. These labels are chosen to selectively bind only to the target (s). The labeling fluid may be recirculated. Once the targets are labeled, the column is flushed to remove all magnetic labels that are not attached to targets. Then the column is eluted in a manner that released the bond between the targets and the stationary phase, without disturbing the bond between the targets and the magnetic labels. The elutant thus will contain labeled targets, a reduced number of excess magnetic labels, and the total volume is substantially less than the original sample (ie: the targets will have been concentrated.) The elutant will then be passed though the NMR detector, which will count the magnetically labeled targets. Even if all the excess beads are not removed, a reduction in their numbers is very useful. In another embodiment, the stationary phase of the column can be liquefied and could pass through the NMR detector. For example, a solvent appropriate for the column's solid phase material would dissolve the solid phase. The stationary phase can be released (via the removal or induced failure of the frit on the output side of the column) and pass through the NMR detector. For example, if the solid phase is made up very fine particles that can pass through the detector, they can be held in place in the column by a grate-like structure, called a frit, which constrains them mechanically to stay within the column. Once the column is loaded, the frit is released, and the now unconstrained particles flow through the detector, along with any targets bound thereto.

Concentration of target entities on the affinity column allows processing of larger amounts of biological, or other fluids of interest, such as environmental water, industrial wastes, process water, or water used to wash foodstuffs, such as vegetables. The column can accommodate much higher flow rates than are used in the detection step. It may not be otherwise practical to process large sample fluid volumes directly through the microcoil because it is understood that the high sensitivity of the method partly derives from the use of very small volume microcoils. The coil volume may be measured in, for example, nanoliters ($10^{-9}$ Liter). However, with the use of an affinity column with a volume of, for example, microliters ($10^{-6}$ Liter) one thousand times as much fluid can be processed in order to concentrate and trap targets in the same amount of time required to process the microcoil volume. This may serve to shorten the analysis cycle markedly; for example in this case by 1000-fold. It also may reduce the amount of non-specific material introduced into the NMR detector so that the rate of false-positive results may be reduced. The use of an affinity column may increase the sensitivity of the detection method. For example, if one is wishing to detect a single bacterial cell in $10^{-2}$ Liter of whole human blood, if the flow rate is limited, for example to $10^{-6}$ Liter per minute, it would require 10,000 seconds, or almost 3 hours to process a single blood sample. However, with a $10^{-5}$ Liter affinity column in place, the flow may be increased to $10^{-3}$ Liter per minute with the result that the blood sample may be loaded onto the column in only 10 seconds. Then, the column can be eluted, and only the fraction known to contain the void-volume peak (containing the target of interest) need be sent into the NMR coil. The column also serves to provide a surface onto which the specific biochemistry needed to assemble the unique target complex can take place. Material specifically eluted from the column by the release agent (imidazole, glucose, pH, ionic strength, etc.) then enters the detection zone and provides a specific signal characteristic of the target sought.

In a ninth aspect, the present invention provides methods for detecting a target is a sample fluid, comprising:

(a) introducing a sample fluid into a sample reservoir, wherein the sample reservoir is in fluid communication with a conduit, wherein the conduit is disposed proximate to a microcoil, wherein the microcoil possesses an inner diameter of between 25 microns and 550 microns, wherein the microcoil is an effective magnetic resonance transmitter or receiver coil;

(b) flowing the sample fluid into an affinity column in the conduit, wherein the affinity column comprises two or more layers, wherein each layer comprises one or more capture agents that bind to one or more targets of interest in the sample fluid, wherein each layer in the affinity column is capable of binding to molecules distinct from other layers; and wherein the affinity column is located at least partially within the microcoil;

(c) flowing a fluid comprising magnetic particles into the affinity column, wherein the magnetic particles are capable of binding selectively to the one or more targets of interest, and wherein binding of the magnetic particles to the targets produces magnetic particle-target complexes;

(d) energizing the microcoil at a frequency that permits detection of a magnetic resonance within the affinity column; and (e) processing a signal received from the microcoil to detect magnetic particle-target complexes in one or more layers of the affinity column.

In a tenth aspect, the present invention comprises methods for detecting a sample in a target fluid, comprising:

(a) mixing a sample fluid with magnetic particles capable of binding to the one or more targets of interest in the sample fluid, wherein binding of magnetic particles to targets produces magnetic particle-target complexes (b) introducing the sample fluid into a sample reservoir, wherein the sample reservoir is in fluid communication with a conduit, wherein the conduit is disposed proximate to a microcoil, wherein the microcoil possesses an inner diameter of between 25 microns and 550 microns;

(c) flowing the sample fluid into an affinity column in the conduit, wherein the affinity column comprises two or more layers, wherein each layer comprises one or more capture agents that bind to one or more targets of interest, wherein each layer in the affinity column is capable of binding to molecules distinct from other layers; and wherein the affinity column is located at least partially within the microcoil;

(d) energizing the microcoil at a frequency that permits detection of a magnetic resonance within the affinity column; and (e) processing a signal received from the microcoil to detect magnetic particle-target complexes in one or more layers of the affinity column.

In these aspects, the methods identify target entities by location within a multi-layer affinity column. By trapping different targets in different regions of space, they can be differentially detected using multiple NMR detectors or MRI techniques. For example, a change in overall signal can first be detected, followed by the use of MRI methods to identify which of the layers is the source of the signal change. In one embodiment, the microcoil is integrated with the affinity column. Affinity columns can be made very small and typically contain substances that can produce NMR signals. Hence, a microcoil can be built into (or around) a column and used to directly detect targets trapped inside. The coil can be wound around the column, or embedded in its walls.

In one embodiment, a fluid containing magnetically labeled targets can be made to flow through such a column, with the column functionalized with capture agents to preferentially trap the targets. This trapping can be chemical and/or physical in nature. The magnetism of the target will affect the detected NMR signal; many different effects are possible as described herein, and the NMR signal detection protocol is optimized for each one accordingly. In one embodiment, NMR detections might proceed while the fluid is flowing through the affinity column, or the fluid flow might be stopped once the sample has been loaded onto the affinity column. The NMR protocol (or data analysis procedure) can be designed to distinguish between stationary magnetic targets and moving magnetic particles. For example, the distinction can be based on two detections of position of the target, where if the position changed, the target is be identified as moving. In another example, a flow-compensated NMR pulse sequence (such as those used in MRI angiography) is used to distinguish between signals detected from moving and non-moving samples. Techniques for optimizing the detection of NMR signals from moving sample fluids may be employed, for example, by using flow compensating magnetic field gradient wave forms, or by rapidly repeated data acquisitions together with small flip angles optimized to give optimal SNR. The column material itself can be chosen so as to contribute to the NMR signal, including that part of the signal affected by the presence of a magnetic target. The column material can be modified ("liquefied") so that it contributes to the detected NMR signal. The column material can be chosen so that it does not alter the magnetic field being applied to the sample space (i.e., the column's stationary phase can be chosen so that it has the same magnetic susceptibility as the fluid). In another embodiment, the affinity column's solid phase can be dissolved so that the column's contents pass through the detection zone, eliminating the need for elution and allows more of the column itself to contribute to the NMR signal (for column-integrated detectors).

The use of these methods provides many advantages, in that stationary magnetic target can be detected many times, confirming the positive detection. Different protocols can be applied to a target of known location, improving detection accuracy and precision, allowing more definitive detection, differential detection, etc. The integrated detector coil eliminates the need for a separate elution step, which may take too much time, damage the targets, strip the magnetic labels from the targets, cause the targets to be diluted into a larger elution volume, cause the targets to spread through diffusive processes into a larger region of sample volume, etc.

In an eleventh aspect, the present invention provides methods for detecting a target in a sample fluid, comprising:

(a) introducing a sample fluid into a sample reservoir, wherein the sample reservoir is in fluid communication with a conduit, wherein the sample fluid comprises magnetic particles capable of binding selectively to one or more targets of interest in the sample fluid, and wherein binding of magnetic particles to targets produces magnetic particle-target complexes;

(b) flowing the sample fluid through the conduit disposed proximate to a microcoil, wherein the microcoil possesses an inner diameter of between 25 microns and 550 microns;

(c) energizing the microcoil at a frequency that permits detection of a magnetic resonance within the sample fluid;

(d) processing a signal received from the microcoil to detect magnetic particle-target complexes in the sample fluid;

(e) flowing a portion of the flowing fluid in which the labeled entity was detected through a conduit disposed proximate to a secondary microcoil;

(f) energizing the secondary microcoil at a frequency that permits detection of a magnetic resonance within the sample fluid; and (g) processing a signal received from the secondary microcoil to determine a further property of the magnetic particle-target complexes.

In order to enhance signal to noise (S/N), it is possible to have a two step process, whereby a fast detection process with poorer S/N is used to determine the presence of any pathogen, and then a slower detection process, with better S/N is used to determine a signal level with good discrete discrimination between magnetic bead levels used. The methods of this aspect of the invention use an initial detection step to trigger a secondary measurement in the same device. This can be done with or without sequestration. The "secondary microcoil" can be a different microcoil or the same microcoil where the sample fluid has been recirculated to it for measurement of a secondary property of the magnetic particle-target complex (ie: something other than detection). In one embodiment, the device is operated in a high through-put mode initially, with a relatively large volume of sample being processed. The initial detection process is optimized for sample throughput, making it difficult to learn much more than the simple presence of a target. Once a detection event has occurred, however, we can shift the focus of the device from merely detecting things to learning more about them, such as their identity. This is possible without changing the label on the targets, but by acquiring data in ways that give more resolution, have more precision, etc. These other data collection techniques are slower than the high-through put mode. The second measurements can be done, for example, in a separate microcoil. This separate coil may have characteristics that optimize signal to noise in addition to the reduced fluid flow velocity in the coil. The separate coil and detection process may employ different NMR excitation and detection techniques capable of making measurements or achieving measurement accuracy distinct from those possible in the initial detector coil.

In one embodiment, the separate microcoil is placed along the conduit flow path downstream from the initial microcoil. The fluid flow rate might be stopped or slowed, or the geometry of the flow can be changed (larger conduit diameter, e.g.) in a manner appropriate for enhanced, reduced-speed detections. The second step can also be done in the first microcoil, with the target brought back into that coil by flowing the sample in the opposition direction. The second step could occur in a "by line," a parallel flow path in which the fluid moves more slowly, or is temporarily stopped. The second step may comprise an NMR experiment protocol that is distinct from the initial protocol so that it highlights a different aspect of the target's signal.

Alternatively, the second "high S/R" detection process may be applied after the entire sample fluid has been processed in the initial step.

These second steps may comprise any useful measurement, including but not limited to precise measurements of relaxation times, and spectroscopic identification of objects or molecules including the identification of properties or features of the labels that were not discernable during the rare entity detection phase of the device's operation.

In a twelfth aspect, the present invention provides methods for detecting a target in a sample fluid, comprising:

(a) introducing a sample fluid into a sample reservoir, wherein the sample reservoir is in fluid communication with a conduit, wherein the sample fluid comprises magnetic particles capable of binding selectively to one or more targets of interest in the sample fluid, and wherein binding of magnetic particles to targets produces magnetic particle-target complexes;

(b) flowing the sample fluid through the conduit disposed proximate to a microcoil, wherein the microcoil possesses an inner diameter of between 25 microns and 550 microns;

(c) energizing the microcoil at a frequency that permits detection of a magnetic resonance within the sample fluid;

(d) processing a signal received from the microcoil to detect magnetic particle-target complexes in the sample fluid;

(e) diverting a portion of the flowing fluid in which the magnetic particle-target complexes were detected into a sequestration chamber to produce a concentrated target solution.

Since the methods of the present invention determine where in space a target is, an identified target can then be sequestered for further analysis. The detection volume can be very small (a few nanoliters, typically), and this volume can be confined in a very narrow conduit, and the sample fluid being measured can be made to flow through this conduit. We can, for example, use a detection event to trigger microfluidic valves that will collect very small, isolated sections of the flowing sample in a sequestration chamber, so that the collected sections contain the objects that were seen by the NMR detector. Nearly all of the background fluid flows through the conduit without being sequestered. The end result is the sequestration of the objects of interest into a very small total volume. That is, a dramatic enhancement of concentration of the targets, making further processing (either in the NMR device or in some subsequent device or procedure) much faster, easier, and more effective. Further in-device processing might be used to differentially identify targets, suppress false positives (especially those due to locally high background bead concentrations, eg.), etc. In one embodiment, sequestration can be allowed to complete during an initial detection run, with a subsequent processing of the sequestered sample, or the processing the sequestered material might commence immediately. In a further embodiment, sequestration can be used to reduce false positives from high background concentrations, by running the sequestered sample through the detection zone again (same or different microcoil).

In a thirteenth aspect, the present invention provides methods for detecting a target in a sample fluid, comprising:

(a) introducing a sample fluid into a sample reservoir, wherein the sample reservoir is in fluid communication with a conduit, wherein the sample fluid comprises two or more targets of interest, and wherein the sample fluid comprises magnetic particles differentially bound to the two or more targets of interest to create at least a first magnetic particle-target complex and a second magnetic particle-target complex;

(b) flowing the sample fluid through the conduit disposed proximate to a microcoil, wherein the microcoil possesses an inner diameter of between 25 microns and 550 microns;

(c) energizing the microcoil at a frequency that permits detection of a magnetic resonance within the sample fluid; and (d) processing a signal received from the microcoil to differentially detect the at least first magnetic particle-target complex and the second magnetic particle-target complex in the flowing fluid.

In this aspect, the methods permit detection and classification/identification in a single data acquisition step. We can differentially detect two or more unique targets if we can attach different amounts of magnetic material to each. All such labeled targets are detected in detection devices of the invention because they will all cause a decrease in the detected NMR signal. The more magnetic targets will cause a larger decrease in signal. We can determine the degree of signal decrease (or other modification of the signal) and use this information to determine which kind of target was detected.

This method requires different levels of magnetic labeling on the targets to be differentiated. These levels of labeling can be achieved in various ways, including but not limited to:

(a) Attaching the same number of beads (on average) of the same size to the unique targets, where the beads for target A have more magnetic strength than the beads for target B. Different strength beads may be made from different magnetic materials, or contain different amounts of the same material (e.g. 60% $Fe_3O_4$ vs. 90% $Fe_3O_4$);

(b) Attaching different sized beads to the different unique targets. This results in differential labeling because different numbers of beads are attached per unit target surface area, and the magnetic moment per bead is different for the different sized beads (e.g., beads containing the same fractional amount of the same magnetic material will differ in magnetic strength due to the total magnetic content);

(c) Attaching a maximal number of the same beads to all of the unique targets, where the targets themselves differ in total surface area. The unique targets differ in total magnetic moment because the total number of beads that can be accommodated;

(d) Use the same beads for all targets where the particular capture agent chosen, such antibodies, have different affinities for the different unique targets, resulting in a different (average) number of beads attached to each type of target.

In one embodiment, the level of labeling is measured in a separate step from the initial detection. This second step might occur in the same fluid stream (e.g., in a second microcoil and detection volume optimized for level detections, or by slowing down the flow temporarily to improve level-precision, etc.) or may be in a parallel stream or a parallel stop-flow experiment. The level of labeling determination might be done in a completely separate apparatus, using sequestration techniques in the initial detector. A different experimental magnetic resonance protocol might be employed to differentiate between the different types or degrees of labeling. We have generated data showing the different detection of clusters of small numbers of beads. This data demonstrate extraction of signal intensity differences using the methods and devices of the invention, and the ability to discern multiple levels of "labeling."

The following further embodiments can be used with any embodiment/aspect of the invention.

To achieve stronger, more-sensitive, faster, or otherwise improved detection, the microcoil detector may be immersed in a material that matches the susceptibility of the metal used to wind the coil. Alternatively, or in addition, the wire of the coil may be chosen or treated such that its magnetic susceptibility matches its surroundings. The material forming the tube on which the coil is wound, or in which the coil is wound, and which contains the fluid sample may be chosen to match either the susceptibility of the fluid, or of the wire, or in any other way to best facilitate detection.

In one embodiment, the processing comprises processing a plurality of signals received from the microcoil over time (ie: two or more time points), wherein the processing comprises identifying a plurality of frequency components and a plurality of magnitude components within each signal received from the microcoil, and correlating the plurality of magnitude components and plurality of frequency components within each signal to a presence or absence of a labeled entity in the flowing fluid at a plurality of locations along an axial length of the microcoil. In this embodiment, signals are processed from two or more time points (ie: 2, 3, 4, 5, 6, 7, 8, 9, 10, or more), permitting correlation of signal data from two or more different time points to identify an appropriate correlation between signals, confirming that the signal is not caused by background or other electrical disturbances. For example, a first signal is detected in one location and a second signal is detected at a second time point at an appropriate distance from the first signal, based on fluid velocity and other factors. Those of skill in the art will understand, based on the teachings herein that appropriate spacing between time points will depend on a variety of factors, including but not limited to microcoil size, fluid velocity and viscosity, conduit size, etc.

The methods of the present invention can be used, for example, in MRI and/or NMR detection of one or more labeled molecules ("entity") in a fluid; the methods disclosed herein provide dramatic reduction in susceptibility to false positive and false negative detections. The methods permit the detection of a labeled entity in a flowing fluid, and also permit multiplexing of the detection process, providing the reliability of repeated single NMR experiments in a single experiment. The methods also permit the presence and movement of a labeled entity within a sample volume to be observed and recorded. Entities that can be detected using the devices and methods of the invention, include, but are not limited to, cells (such as bacteria, fungi, other parasites, cancer cells, etc.), viruses, proteins (including antibodies), prions, nucleic acids, carbohydrates, lipids, small molecules, antibiotics, toxins, etc.

In various embodiments, detection via the methods of the invention can comprise detection, identification, and/or quantitation of entities in a sample fluid. Any sample fluid of interest can be used, including but not limited to bodily fluid samples (blood, urine, saliva, semen, vaginal secretions, tears, amniotic fluid, cerebral spinal fluid, etc.), swab samples from skin, wound, or other body sites; semi-solid samples, such as fecal samples (processed by appropriate sample dilution in a liquid), environmental water, industrial wastes, process water, liquid foodstuffs (including but not limited to milk, juice, drinking water, soda, etc.) or water used to wash foodstuffs such as vegetables and fruit. The size of the sample volume may vary depending on the properties of the fluid being analyzed, the desired flow rate through the sensitive volume, and the sizes of the conduit. The sensitive volume of the conduit (ie: the volume being analyzed) can vary depending on the size of the sample volume, the size of the conduit, the flow rate, the size of the microcoil, and other factors as determined by a user. In various embodiments, the sensitive volume ranges between 100 picoliters and 50 microliters. In various other embodiments, the sensitive volume is ranges between 4-7, 2-10, 1-15, 0.5-20, 0.4-50, 0.3-75, 0.2-100, 0.1-150, 0.05-300, 0.04-500, 0.03-1000, 0.02-2000, 0.01-5000 nanoliters. In an example detector, less than a nanoliter of fluid is contained in the sensitive volume of the detector at any given time. However, nanoliter, microliter, and even milliliter-sized samples may be used depending on the overall capacity of the detector. For larger samples, or samples suspected of having low concentrations of targeted entities, the use of a concentrating mechanism such as an affinity column may facilitate a reduction in the sample volume. For example, an environmental sample of 50 milliliters may be suspected of containing low concentrations of a target entity. To speed up the detection process, an affinity column with a moiety capable of selectively binding to the target entity may be used to isolate and hold the target entity while the remainder of the sample is washed away. After the extraneous portion of the sample is removed, and carrier fluid can be passed through the affinity column to carry the previously trapped target entities into the sensitive volume of the detector.

Any suitable method for labeling target entities can be employed. In various embodiments of the methods of the invention can comprise labeling a target entity with a detection enhancing label using specific attachment chemistry to influence the magnetic resonance properties of the sample fluid. Any label that can be used to specifically target an entity of interest can be used, including but not limited to magnetic beads derivatized for binding to an entity of interest. In an example use of a label, a magnetic bead labels a pathogen by using antibodies bound to the magnetic bead that are selective for target antigens on the pathogen. The magnetic bead alters the magnetic resonance of the fluid surrounding the bead, causing the fluid surround the bead to behave differently than the fluid would in the absence of the magnetic bead. Any bead that causes the target entity or the fluid surrounding the target entity to exhibit different magnetic resonant behavior than the remaining fluid in a sample can be used as a label. For example, magnetic and non-magnetic beads can be used. In another example use of a label, a plurality of different beads with known magnetic resonance profiles and the ability to attach to specific target entities are added to a fluid sample. If one of the known magnetic resonance profiles is detected during an experiment, then the corresponding entity is present within the fluid. By using a multiplicity of different beads during a single experiment, a single experiment can be used to detect a multiplicity of entities within the fluid. Beads may also be internalized by the target entity, either singly or in multiplicity, for example by eukaryote cells.

The use of multiple layers of beads results in an increased magnetic moment. By increasing the effective area of the target cell or molecule by attaching a first layer of beads (or single bead) or first layer of molecules, and attaching the magnetic labels to this first layer, the target object is effectively larger and has more surface area. Hence, it can bind more of the magnetic labels that we use for detection. The first layer need not be magnetic. The methods for attachment between target and first bead, and between first bead and magnetic label, can be chosen to enhance the sensitivity and specificity of the labeling.

In another embodiment, two (or more) magnetic materials with different chi are used to differentially label targets, so that in low fields, one will have a higher magnetic moment than the other because it is more highly magnetized. Paramagnetic materials respond linearly to the application of an applied field. In particular, they become magnetized in direct proportion to the strength of the applied field, with the proportionality constant often called "chi", the magnetic susceptibility. This linear response cannot go on forever, at some high value of the field, the magnetism of the material no longer increases. The material is said to saturate, and the magnetic moment that it has in this state (Msat) is the largest it can have. Of interest here are two materials with different chi, so that in low fields, one will have a higher magnetic moment than the other because it is more highly magnetized. However, if this material with a higher chi value has a lower Msat value, then as the applied magnetic field is increased (by choice of a different or subsequent magnet, say) then the second material will eventually have a higher magnetic moment. The strength of the magnetic moment can be assessed in our detection process, and we will be able to tell which is stronger in any given magnetic field. Then at one field strength bead A has a larger moment, while at another strength bead B has a larger moment.

The label may also be one that modifies signal by displacement of the medium surrounding the object(s), such as through attachment of glass or plastic beads. Alternatively a label may be used that enhances or changes the signal, such as by attachment of a material whose properties are measured directly, as opposed to the signal from the medium. The bead could consist of iron, iron oxide ($Fe_2O_3$, $Fe_3O_4$), Fe:Pt, gadolinium metal or gadolinium oxide, iron nitride ($Fe_4N$), or other ferromagnetic, paramagnetic, or super-paramagnetic material encapsulated in some manner, for example, encapsulated in glass or in a plastic. The bead could also be made up almost entirely of the magnetic material, either coated or uncoated. A coating might be applied to guarantee inertness in the fluid of interest, to stabilize the magnetic particle against degradation during use or storage, or to allow the attachment of other materials or coatings in order to optimize some behavior, such as attachment of antibodies for the facilitation of attaching to the target entity.

Magnetic material may be chosen to provide the best possible magnetic moment, or provide the best overall signal performance. As some materials saturate in an applied field, another material with a lower magnetic moment might allow for a better overall signal due to lack of saturation. The magnetic material can be ferro-magnetic, ferri-magnetic, paramagnetic, super-paramagnetic, or diamagnetic. If ferro-magnetic, the beads may be magnetized prior to their use in the device, or they may be demagnetized initially and become permanently magnetized as they pass through the magnet.

Iron oxide beads may also be of a particular size, i.e. nanoparticles, such that the beads are super-paramagnetic, with advantages that the beads are not magnetized when there is no strong applied field, while on the other hand developing a very large magnetic moment when subjected to a magnetic field. The lack of a permanent magnetic moment can keep the beads from aggregating in the absence of an applied magnetic field.

The effect on the surrounding medium of beads with smaller magnetic moments can be different from the effect of beads with larger magnetic moments because the size of the volume of surrounding fluid affected by the bead is roughly proportional to the magnetic moment of the beads. This can be used to facilitate differentiation of targets to which beads preferentially attach. To achieve differences in magnetic moment of bead labels, beads containing different densities of magnetic material, beads of different sizes, beads containing different materials, or any combination of these or other factors may be employed. Differentiation may also be achieved by variations in the multiplicity of the labeling, for example, with larger targets carrying more beads on their surface.

In an example of one embodiment, two species of bacteria are present in a fluid, and each are specifically labeled with beads with the associated antibody targeting the specific species of bacteria. The amount of iron oxide in the beads of the label for, in one example, bacteria 2 (B2) is larger than that of the label for bacteria 1 (B1). Including the effect of the average binding density of the bead labels to the target bacteria, it is possible to differentiate the signals from the two species of bacteria based on the differences in the net magnetic moment, and therefore the amount of fluid medium the targeted bacteria affects as it flows through the detection coil. The detection events are manifested in a reduction in the signal from the medium, with the target with larger net magnetic moment producing a larger decrease in signal.

It may be advantageous to provide additional labeling to the sample, for example to increase the signal associated with a detection event, wherein the initial label bead itself is subsequently labeled by additional beads. These secondary beads may be appropriate for creating additional signal or entity differentiation. For example, secondary beads containing a larger fraction of magnetic material may be constructed to bind to primary beads which recognize a particular entity, while other secondary beads, containing a smaller fraction of magnetic material may be constructed to bind to primary beads which recognize a separate entity. Differentiation of one labeled entity from the other is accomplished by an analysis of the resulting signal from the medium. Secondary beads can be used to alter the signal in some other way, for example adding ferromagnetic secondary beads to the initial beads for a particular bacterial species, and paramagnetic secondary beads to the initial beads for another bacterial species, and in this way differentiate between two or more bacterial species.

The methods may be used for rare entity detection or for entity concentration measurement device. In rare entity mode, the detector will generally have only one target entity in its sensitive volume at any one time. In this mode, the goal of the device is to find the rare target in a relatively large volume of fluid that is flowing through the detector volume. In concentration mode, the detector will have many targets in the sensitive volume and the methods can be used to characterize the concentration in relative or absolute terms.

Signal differentiation may also be achieved through control of the magnetic moment of the bead that is attached to a particular target. This may be achieved through control of the amount of magnetic material in a bead, the size of beads at a given concentration, the type of magnetic material used to produce different magnetic moments, the number of beads attached, and so on. Thus it is possible to provide, for example, multiply labeled species or strains of pathogens and have them be uniquely identified by characteristics of the NMR signal, such as amplitude.

Differentiation between targets may be achieved via measurements of secondary effects of the labels on the detected signal. For example, the detection of the presence of a target may be achieved by making one kind of measurement, for example $T_2^*$, while the differentiation between different targets so detected may be achieved via the measurement of a second NMR property, for example $T_1$. The differentiation may be enhanced through the use of more than one kind of bead that share the same (or nearly the same) values of some detection properties while differing in other properties. These different beads may label distinct targets, or some combination of beads might label each target, with the combination being distinct from one target to the other.

In addition to a magnetic label, further entity differentiation can be achieved through the attachment of other material to the target, such as fluorescent, optical-absorption, or acoustic labels. An example of an acoustic label is a structure with a characteristic ultrasonic signature. Fluorescent labels include fluorophores (fluorescein, rhodamine) and quantum dots. This additional labeling may be provided to, for example, do sample detection and identification either in conjunction with or as a separate step, before or after the detection according to the methods of the invention. For example the detection event can trigger the isolation, or sequestration of the detected bacteria into a separate fluid path, wherein it can be further interrogated, for example optically using fluorescence or absorption. The additional labels may be attached before or after the detection step, or may be integrated into a single object as a "multi-modal" label.

The sample fluid in which labeled target are processed may be changed or modified to enhance signal. Useful changes may be made to the hydrogen density, viscosity, or other chemical or physical properties of the fluid. The changes can be achieved by replacement of one fluid by another, by the addition of solid or fluid components to the matrix fluid, by changing the temperature or pressure of the fluid, etc. These changes may affect the $T_1$, $T_2$, or $T_2^*$ of the fluid in a beneficial way, for example, by yielding higher detection signals and allowing faster processing. The $T_1$ of the fluid may be reduced through the introduction of Magnevist or any other $T_1$ contrast agent. Shorter $T_1$s are beneficial in that the detection measurement can be performed more rapidly, and repeated at higher rate.

The labeling of individual target entities can rely on any suitable labeling technique, including but not limited to antibody-based techniques. Antibodies are protein molecules which recognize particular chemical sites, called epitopes, on other molecules. Antibodies can be attached, either chemically, or biochemically, to the surfaces of primary or secondary magnetic beads. A biochemical example is a bead coated with streptavidin, a protein which binds very tightly to biotin. Then, a biotinylated antibody for a particular entity will bind to a streptavidin-coated bead. A solution of antibody-labeled beads is then mixed with the sample fluid in which the target entity (such as a pathogen) may be present, for example bacteria in blood. Based on the type of antibody coating of the bead, a bead, or many beads, will attach to the target bacteria. The blood containing the labeled bacteria then flows through the detection coil, allowing the presence of the labeled bacteria to be ascertained.

Alternatively, the target entities may be trapped on a solid phase, such as in an affinity column or other chromatography column. Once attached to the affinity column and immobilized, the solution of label beads with attached antibodies may be introduced so that all of the attached targets are labeled with beads. The excess beads that do not label any target may then be washed out of the column. The targets, with their labels attached, may then be eluted from the column and this eluant can then be processed by the NMR detector.

If many beads attach to a single bacterium the effect of the labeled bacterium on the signal from the medium can be easily observed against the background signal the medium in the presence of isolated single beads. Alternatively, when only a single bead is attached to a bacterium, the unbound beads are preferably removed. The removal of the excess beads may be accomplished by any suitable means. In one example, antibody-beads are incubated with the clinical sample; unattached antibody-beads are then washed through a one-way valve, such as a silicon with a pore size on nm scale (ie: too small for any target pathogens). A second valve would then open and a second wash would send only bead-antibody-complexes and blood components into the detector. Alternatively, the removal of the excess beads may be accomplished by a filter column.

The fluid flow may be stopped during the detection, or the flow may be continuous. For example, the method may comprise detecting the presence of a target entity during fluid flow, followed by a second detection, with fluid flow or with fluid flow stopped, to determine the identity of the detected target entity. Either a single microcoil can be used, with control of the flow (including reversing the flow to bring the target back into the coil), or a secondary coil (placed downstream from the primary microcoil, or in a branch into which the target is steered) can be used. The target entities to be detected may pass through the detector and into an sequestration chamber without being substantially modified. Living organisms or cells retain viability. The output fluid in the sequestration chamber is available for further testing or repeat testing in the device, in a similar device optimized for a different measurement, or any other device or process. Sequestered target entities can be sequestered into a very small volume to enable the rapid location of the targets on a microscope slide or the rapid processing of only the small volume in subsequent processes or devices. The collected, concentrated targets may be further analyzed in the detector, either in the coil used to detect them in the first place, or in a separate detection circuit or method.

The magnetic field may be produced by a permanent magnet, such as the permanent magnets described as part of the detector aspect of the present invention. Any of the magnetic gradient generators that may be used in the detector aspect of the invention may also be used to apply a magnetic gradient to a magnetic field according to the methods of this aspect. Any of the microcoils, conduits, modules, detectors, and combinations thereof disclosed herein may also be used according to the methods of the invention. Further multiplexing of the methods can be achieved by use of conduits comprising multiple branches, which can be coupled with the use of multiple microcoils to provide a variety of detection zones, and further coupled with microfluidics to permit, for example, (i) selective flow of a fluid sample of interest to multiple detection zones for separate detection assays (ie: different fluid flows; different field strengths; different magnetic gradients; combinations thereof, etc.); and (ii) selective flow of multiple fluid samples of interest to separate detection zones for sample multiplexing. Other variations is apparent to those of skill in the art based on the teachings herein.

Any method of causing the fluid to flow may be used. For example, any of the fluidic drives disclosed herein may be used to impart a flow on the fluid. The flow rate used can be any rate desirable for a given application. As used herein, "flow rate" refers to the amount of fluid that moves through the sensitive volume of the detector over time. In one embodiment, the flow rate of the fluid may be between 0.01 microliters per minute and 2.0 microliters per minute. In various other embodiments, the flow rate can be between 0.01-500, 0.01-450, 0.01-400, 0.01-350, 0.01-300, 0.01-250, 0.01-200, 0.01-150, 0.01-100, 0.01-50, 0.01-10, 0.01-8, 0.01-6, 0.01-4, 0.01-3, 0.01-2, 0.01-1.75, 0.01-1.50, 0.01-1.25, 0.01-1.0, 0.01-0.9, 0.01-0.8, 0.01-0.7, 0.01-0.6, 0.01-0.5, 0.5-2.5, 0.5-2.25, 0.5-2.0, 0.5-1.9, 0.5-1.8, 0.5-1.7, 0.5-1.6, 0.5-1.5, 0.5-1.4, 0.5-1.3, 0.5-1.2, 0.5-1.0, 150-250, 175-225, 180-220, 185-215, 190-210, 195-205, 198-202 and 199-201 microliters per minute depending on the properties of the fluid and the particular experiment that uses the methods of the present invention. Lower flow rates and even static fluids may also be used. Any flow rate that permits the detection of a magnetic resonance within the fluid may be used. The flow rates outside the sensitive volume of the detector may also vary. For example, fluid that is held in sequestration chamber or held behind a valve may be static. For fluid flowing through an affinity column, or through a portion of the conduit that distributes fluid samples to other conduit branches, the flow rates may be higher. Further, the flow rate through the sensitive volume of the detector may be varied. For example, a valve placed before the sensitive volume may be used to increase or decrease the flow rate during the course of a detection experiment. In an example method, a detection experiment is primarily conducted at 2 microliters per minute. However, if a signal received from the microcoil indicates that an entity might be present in the fluid, a valve may be activated to slow the flow rate through the sensitive volume to 1.0 microliters per minute. In another example method, a detection experiment may commence at flow rate of 0.5 microliters per minute. If, after a predetermined period of time no entities have been detected, a valve may be activated to increase the flow rate through the sensitive volume of the detector to complete the detection experiment more quickly.

When a flowing fluid enters the magnetic field, the magnetic field causes some of the nuclei in the fluid to align with the field. The magnetic gradient causes the nuclei within the fluid to resonate at different frequencies depending on their location relative to the magnetic field and the magnetic field gradient. By altering the frequencies at which the nuclei in the fluid resonate, the magnetic gradient establishes the spatial resolution of the detector, which permits the detection of an entity within an identifiable section of the microcoil. In an example implementation of the methods of the invention, the conduit is positioned such that a long axis of the conduit is parallel with the direction of the gradient. However, the conduit can be disposed elsewhere within the field of the magnetic gradient generator provided there is sufficient gradient component along the conduit to spatially resolve magnetic resonance events along the conduit.

The methods also comprise processing a signal received from the microcoil to detect an entity in the fluid. The combination of the magnetic gradient (if present) and the magnetic field causes the field strength to vary along the length of the conduit, which in turn causes the nuclei within the fluid to resonate at different frequencies depending on the location of the fluid, permitting identification of numerous contiguous signal producing volume elements along the microcoil. Consequently, the microcoil receives signals from the fluid at a plurality of frequencies, each corresponding to the location of the fluid. By correlating the frequency and magnitude components of the signals received by the microcoil to the corresponding locations within the conduit, measurements identifying the magnetic resonant behavior of the fluid throughout the length of a portion of the conduit can be obtained.

These measurements can be converted into a variety of different representations of the movement of an entity though the fluid, including but not limited to data array of frequency, and position, vs time. The construction of a data array from the signal received from the microcoil can be accomplished using a variety of techniques, including but not limited to a Fourier transformation. In an example implementation of the method, a Fast Fourier Transform technique is used. Baseline correction techniques and phase adjustments may also be used to augment the signal processing. The signal processor may display the signal received from the microcoil in processed or unprocessed form on a user interface such as a monitor or screen.

Other data manipulations may also be particularly useful for reducing the susceptibility to false positive and false negative detections. If the data is acquired in a manner that allows subsets of the signal detected by the microcoil to be assigned to different positions within the conduit, a device implementing the method can become self-calibrating. Further, the determination that an entity is present or absent in a portion of the conduit may be based on detecting a change in a magnitude component relative to a plurality of other magnitude components. Comparing relative magnitudes may reduce the probability that a global increase or decrease in a processed signal that is unrelated to the presence or absence of an entity in the fluid would trigger a detection event.

The processing of a signal may also include comparing data from successive signal acquisitions. In embodiments that impose a unidirectional flow on the fluid, an entity in the fluid may pass through the detector from one end of the conduit to the other. By comparing successive data acquisitions, the passage of an entity through the conduit may be tracked. Further, in embodiments that compare successive data acquisitions, data analysis techniques such as correlation analyses may be used to reject false detections due to electrical noise or other random fluctuations, because it is unlikely that electrical noise or other random fluctuations would mimic the appearance of an entity moving through a fluid in multiple data acquisitions.

The processing of a signal may also include accumulating signal peaks or pertinent signal features, including but not limited to signal minima associated with a target, of a data array representation of the signal received from a microcoil. Accumulating signal peaks may allow multiple scans to be correlated and combined to show the movement of an entity through the fluid. A characteristic velocity of a signal peak that is related to a radial position in a conduit of an entity can be used to accumulate signal peaks across successive scans.

Motion correction methods may also be utilized to further enhance the accuracy of the data acquired. In embodiments where the fluid flow is relatively slow or static, spin-echo or gradient-recalled echo images may be formed. In embodiments using pulsed field gradients, the signal-to-noise ratio and accuracy of the images may be further improved. Multi-dimensional imaging may also be implemented with embodiments that use slow or static flows. Embodiments that implement echo-based techniques may allow a plurality of effects of a labeled entity's presence in a fluid to be measured and imaged.

In embodiments with multiple branches and multiple microcoils, various methods may be used to identify the magnetic resonance behaviors within a given microcoil. For example, the microcoils may be angled with respect to the magnetic gradient such that each spatial element of each microcoil resonates at a different range of frequencies. In another example, electrical switching can be used to selectively monitor a microcoil for a period of time. In another example, each microcoil may be coupled to a dedicated signal processor.

In any embodiment of any aspect of the methods of the invention where a resonant circuit is used, the methods may comprise resonating the resonant circuit at low frequency, and detecting resonance signals from the sample. "Low" frequency is the frequency appropriate for detecting the desired resonance in the magnetic field of the magnet chosen for the device.

The methods of the invention may further comprise electrically coupling the microcoil to a tuning circuit, wherein the tuning circuit comprises a tuning coil having an inductance at least two times the inductance of the microcoil and a capacitor coupled to the tuning coil to form a resonant circuit. Any of the tuning circuits disclosed herein may be used as the tuning circuit.

Further, any of the methods of the present invention may be implemented by a computer program for use with a detector, such as those disclosed herein. The computer program may be implemented in software or in hardware, or a combination of both hardware and software.

In a further aspect, the present invention provides physical computer readable storage media, for automatically carrying out the methods of the invention on a detector, such as those disclosed herein. As used herein the term "computer readable medium" includes magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or be distributed among multiple interconnected processing systems that may be local or remote to the processing system.

EXAMPLES

Referring now to the figures, FIG. 1 depicts a portion of an exemplary microcoil MRI detector 100. A microcoil 102 is solenoidally shaped and wrapped around a conduit 104. The portion the conduit 104 that is within the microcoil 102 is the sensitive volume of the detector 100. The axis of conduit 104 is aligned with a magnetic gradient 106. In a detection experiment, a fluid flowing in direction 108 passes through the conduit 104 and the microcoil 102. The microcoil 102 is electrically coupled to both a tuning circuit 110, and a signal processor 112.

Figure 2:
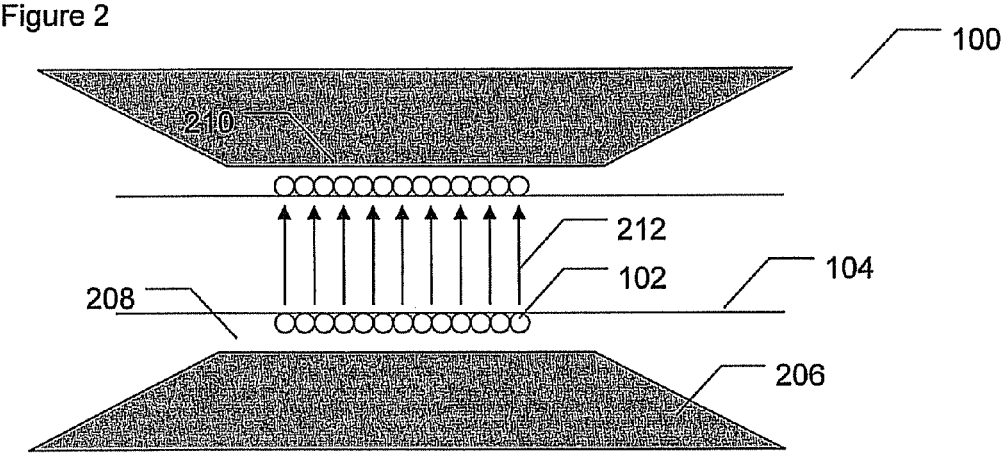
FIG. 2 depicts a cross-sectional view of a detector in accordance with an embodiment of the present invention.

FIG. 2 depicts a cross-sectional view of a portion of an exemplary MRI detector 100. The microcoil 102 is wrapped around the conduit 104 and disposed in a gap in a magnet 206. Magnet pole faces 208 and 210 possess opposite polarity, and a uniform magnetic field 212 is established across the gap in magnet 206.

Figure 3:
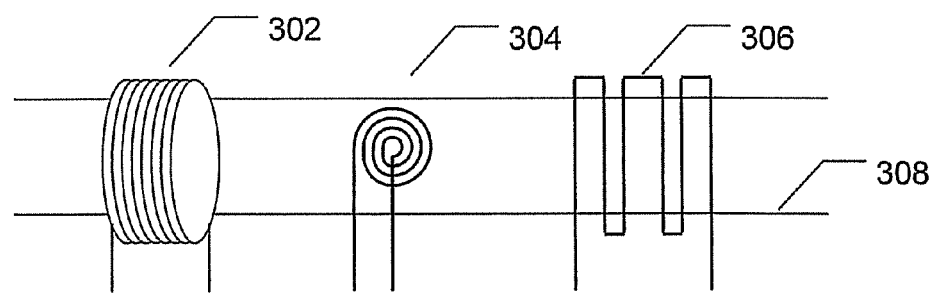
FIG. 3 depicts three example microcoil constructions.

FIG. 3 depicts three different example microcoil constructions 302, 304, and 306. The first microcoil 302 is a solenoidal coil wrapped around a conduit 308. The second microcoil 304 is a flat coil, positioned adjacent to the conduit and oriented to place the axis of the second microcoil 304 perpendicularly to the axis of conduit 308. The third microcoil 306 is a meanderline coil place adjacent to the conduit 308.

Figure 4:
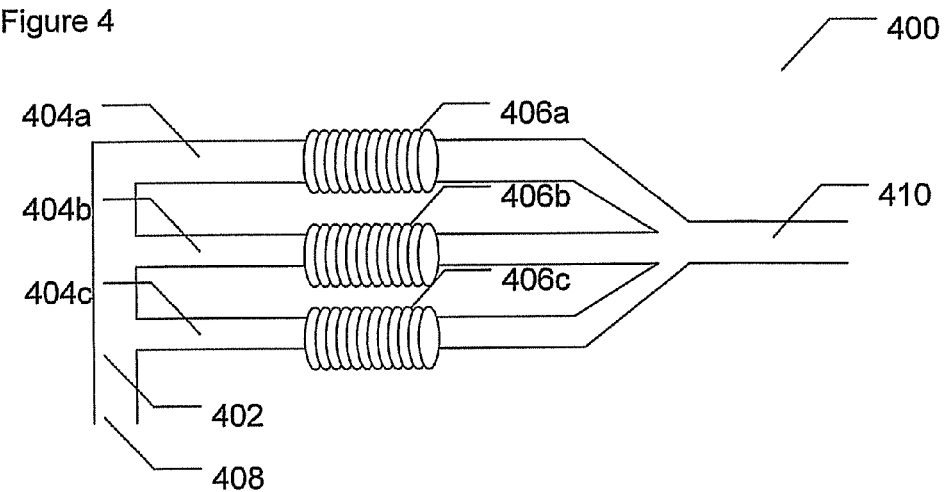
FIG. 4 depicts a portion of a detector comprising a conduit that contains multiple conduit branches.

FIG. 4 depicts a portion of an example detector 400 wherein a conduit 402 contains three conduit branches 404a-404c. Microcoils 406a-406c are solenoidal in shape and are wrapped around conduit branches 404a-404c. A fluid can flow into the conduit at a fluid input 408, and flow out of the conduit at a fluid output 410. In example detector 400, each of conduit branches 404a-404c and microcoils 406a-406c may be independent. For example, each of microcoils 406a-406c may be energized at a different frequency or range of frequencies, which may permit detection of different entities in each of conduit branches 404a-404c. However, microcoils 406a-406c may each be used in identical detection experiments, which may further reduce the susceptibility of the detector to false positive or false negative detections, by allowing for the flow rate through the sensitive volumes of the conduits to be reduced.

Figure 5:
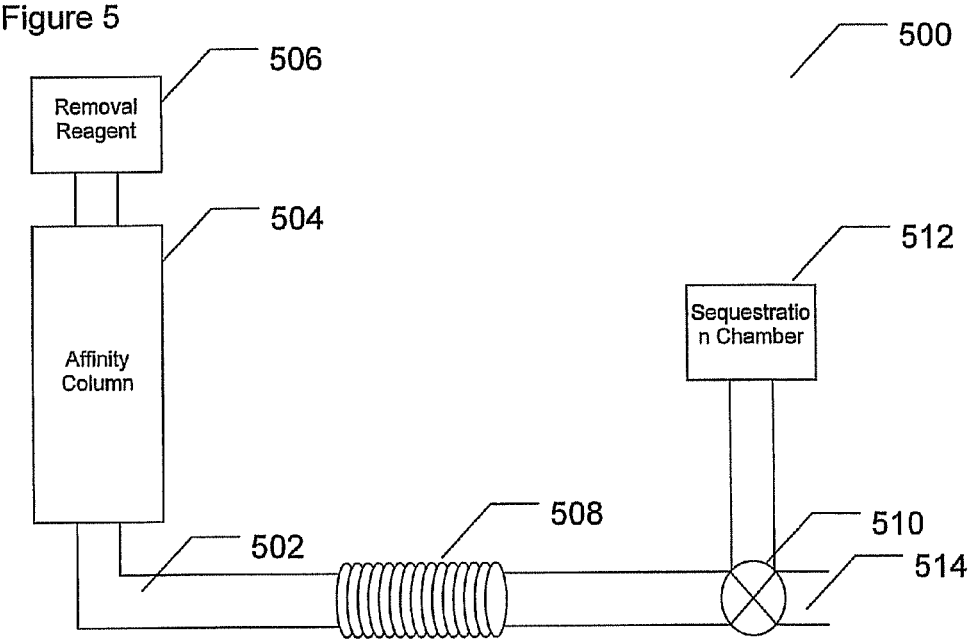
FIG. 5 depicts a portion of a detector comprising additional fluidic components coupled to a conduit.

FIG. 5 depicts a portion of example detector 500 comprising additional fluidic components fluidically coupled to a conduit 502. An affinity column 504 may be used to trap and hold pathogens or other entities until a detection experiment can be conducted. During a detection experiment, a fluid containing a removal reagent 506 may flow past the affinity column 504, and cause pathogens or other entities to enter the fluid. The fluid can then flow through the section of the conduit 502 that is wrapped by a microcoil 508. If an entity is detected by microcoil 508, a valve 510 can be activated to divert the fluid into a sequestration chamber 512 for storage or further analysis. If no entities are detected, the valve 510 may allow the fluid to exit the conduit through fluid output 514.

Figure 6:
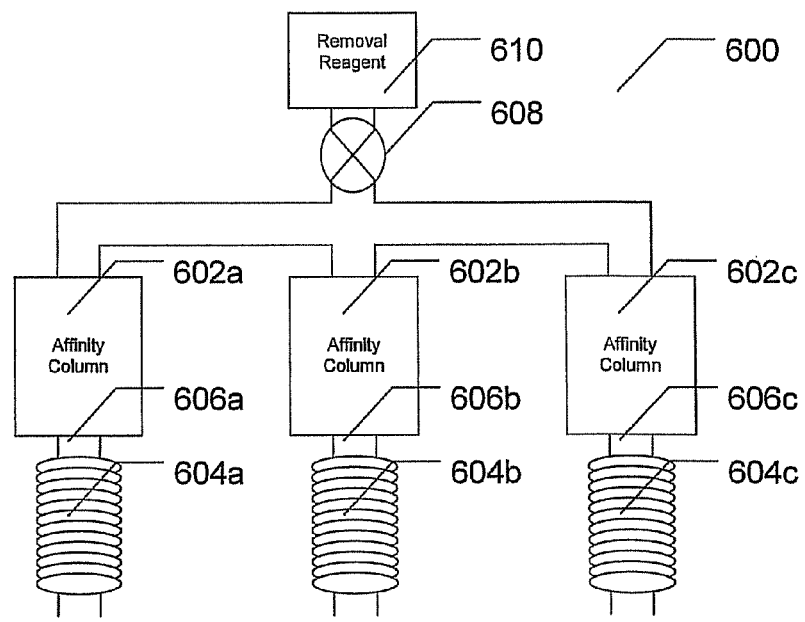
FIG. 6 depicts a portion of a detector comprising three affinity columns arranged to permit multiplexing of a fluid sample.

FIG. 6 depicts a portion of example detector 600 comprising multiple affinity columns 602a-602c. At the output end of each of the affinity columns, solenoidal microcoils 604a-604c are wrapped around conduits 606a-606c. A valve 608 controls the flow of a removal reagent 610 past the affinity columns 602a-602c. The use of multiple affinity columns 602a-602c may permit additional differentiation and increase the throughput of the detector. For example, a detection method may provide ten levels of discernable signal differentiation and use ten specific beads in each of the affinity columns 602a-602c. By processing each affinity column 602a-602c separately, the flow through the microcoils 604a-604c is multiplexed, permitting thirty distinct potential identifications using only ten bead characteristic levels. Further, since three affinity columns 602a-602c are used, a sample can be divided into three portions, permitting the sample to be analyzed three times more quickly than with a single column.

Figure 7A:
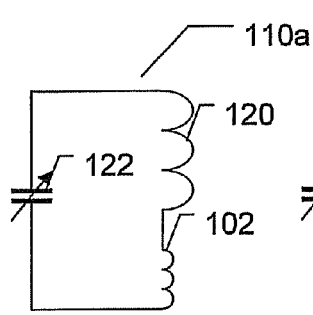
FIGS. 7a-7c depict schematic diagrams of electrical connections between a tuning circuit and a microcoil.
Figure 7B:
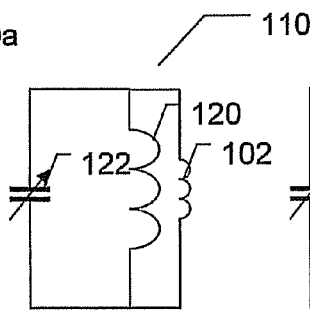
Figure 7C:
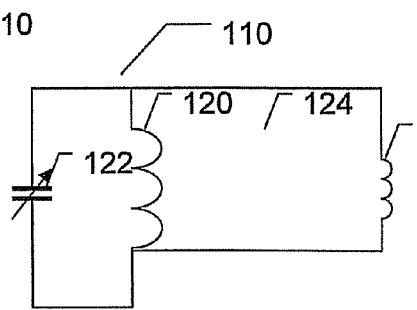

FIGS. 7a-7c depict three example schematic arrangements of the tuning circuit 110 and the microcoil 102. In FIG. 7a, the tuning coil 120 and the microcoil 102 are connected in series, and a resonant circuit is formed with a tuning capacitor 122. In FIG. 7b, the tuning coil 120 and the microcoil 102 are connected in parallel. In FIG. 7c, the tuning coil 120 and the microcoil 102 are again connected in parallel, but the microcoil 102 is remotely located from the tuning circuit 110 via a transmission line 124. In an example detector, the transmission line possesses a length that is an odd multiple (i.e. 1×, 3×, 5×,) of one-fourth of the wavelength of the alternating current induced in the microcoil during resonance.

Figure 8:
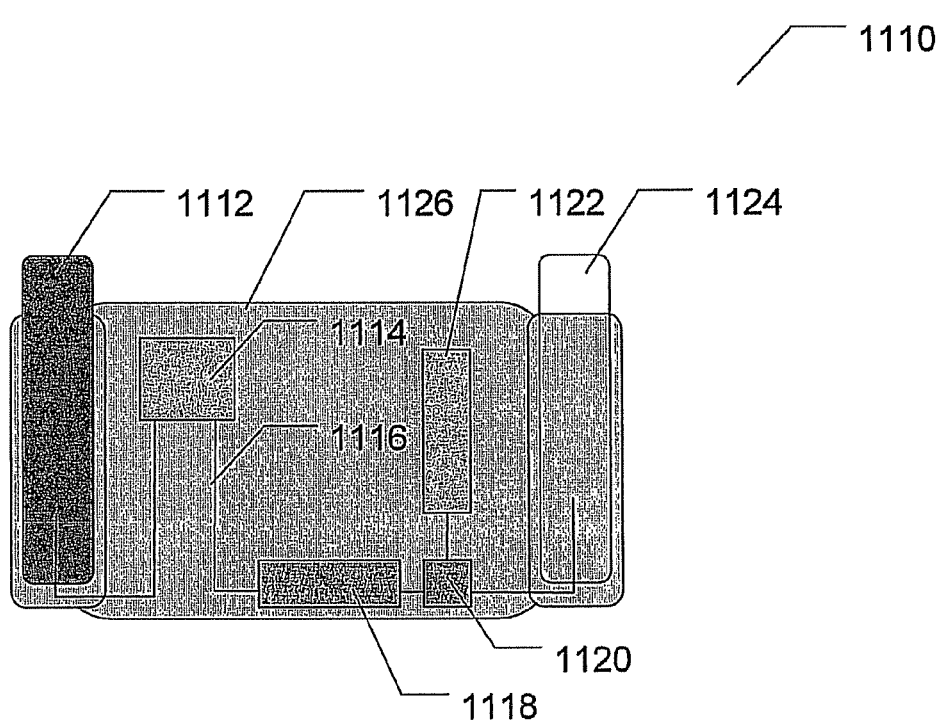
FIG. 8 depicts an example module.

FIG. 8 depicts an example module 1100 wherein a fluid is contained in a sample chamber 1112. The sample chamber 1112 is fluidically coupled to a bead chamber 1114 that contains beads that can be affixed to a target entity in the fluid. A conduit 1116 is fluidically coupled to the bead chamber 1114, passes through a microcoil 1118, and is fluidically coupled to a valve 1120 after passing through the microcoil 1118. The valve 1120 is fluidically coupled to a sequestration chamber 1122 and a exit reservoir 1124. If during a detection experiment the microcoil 1118 detects a magnetic resonance in the fluid that indicates the presence of a target entity, the valve 1120 can be activated to divert the fluid into the sequestration chamber 1122. If no target entity is detected, the valve 1120 can be activated to direct the fluid into the exit reservoir 1124. All of components of module 1100 are mechanically coupled to a substrate 1126, which provides structure support and maintains the relative position of the components on the module 1100.

In an exemplary embodiment, a microcoil with an inner diameter of 170 microns and a length of approximately 1.1 mm is wound around a conduit. The conduit and microcoil are disposed in a magnetic field with a strength of about 1 Tesla, generated by a permanent magnet, and a magnetic gradient of 0.07 G/mm is applied along the long axis of the microcoil. As fluid is passed through the conduit, the data acquisition techniques disclosed herein are applied to detect the presence of a labeled entity in the fluid.

Figure 9:
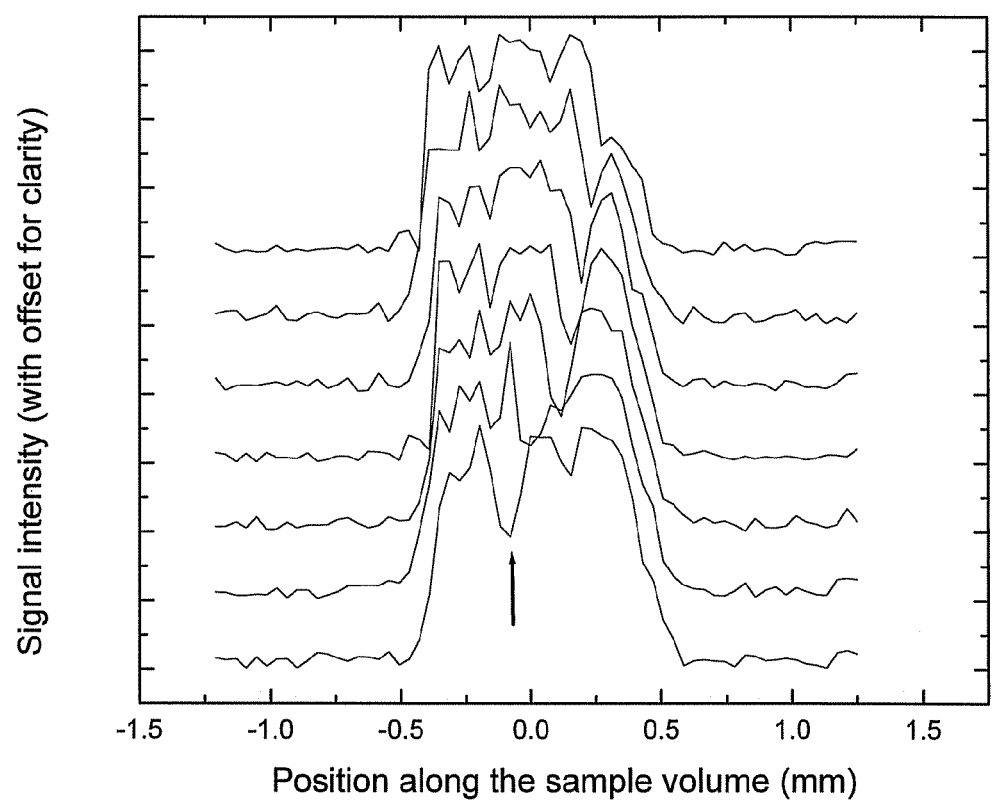
FIG. 9 is a time series of images generated in accordance with a method of the present invention.

The example device was used in a successful implementation of the method. A fluid consisting of Magnevist doped water (T1~430 ms) and dilute magnetic beads (5 micron Bangs beads), was disposed in the conduit, and by following a method of the present invention, a bead was positively identified. FIG. 9 contains a time series of images, offset for clarity, in which the bead appears as a dip in the profile as indicated by the arrow.

Figure 10:
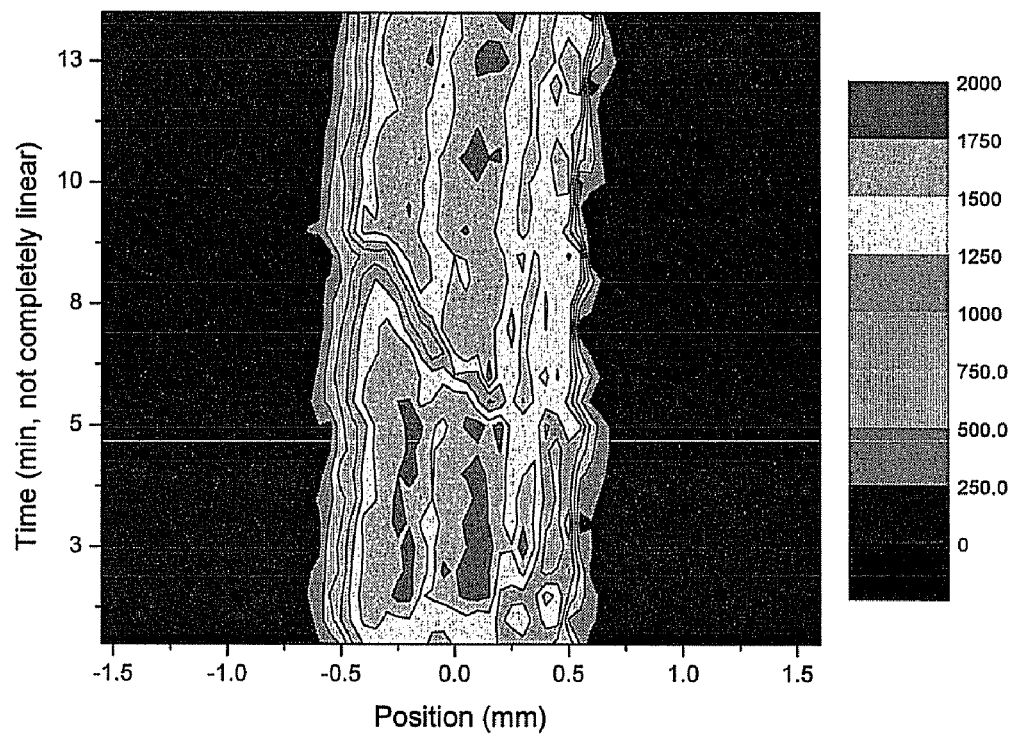
FIG. 10 is a contour plot depicting the full time course of a detection experiment conducted in accordance with a method of the present invention.

FIG. 10 depicts the full time course of a detection experiment as a contour plot. In FIG. 2, the positively identified bead appears as a linear feature moving diagonally up and to the left across the centrally located band. The centrally located band depicts the location of the sample volume.

Figure 11:
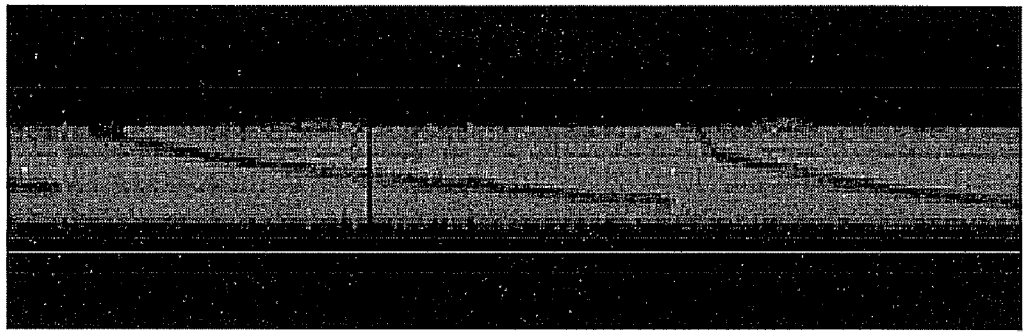
FIG. 11 is a graphical representation of the movement of an entity through a conduit developed in accordance with a method of the present invention.

FIG. 11 depicts a data set from a similar detection experiment using the example device and a method of the present invention. A positively detected bead is visible as dark bands trending to the lower right within the light band.

Example 2

There are many species of bacteria, and within each species there are also many strains. Of the virulent bacteria some strains are more virulent than others. Additionally, some strains of a particular species can be resistant to antibiotics, for example MRSA (Methicillin-resistant *staph. aureus*) and GBS. Antibodies are available or can be produced that provide strain-specific labeling of bacterial pathogens. Information of this nature may be useful for the identification of the appropriate antibiotic for clinical use based on the identification of species or strain of a bacterium.

There are also antibodies that are 'pan-bacterial' and that are specific for a particular antigen that is indicative of some subset of bacteria, for example, all strains in a species, or all of a particular group that shares a common antigenic characteristic, or for example, all Gram-positive (G+), or all Gram-negative (G−) bacteria. In this way a test using the methods of the invention provide for the screening of blood such that the presence of any Gram-positive or Gram-negative bacteria is detected. Further variations include, but are not limited to: [Gram-positive, Gram-negative, Fungi]; or [Gram-positive, Gram-negative, Fungi, mycobacteria]; or some set of these plus a particular protein or multiple proteins, which are indicative of a particular disease state or other important clinical information.

A particular label, with a certain signal characteristic, can be applied to all bacteria or other pathogens that are susceptible to a particular antibiotic, and thus a characteristic signal in a test sample from a patient identifies the patient as one that would benefit from use of a particular antibiotic. This labeling approach, to label a set of pathogens with a particular property or characteristic, may be accomplished by attaching the several antibodies to all beads, or have a single type of antibody attached to a bead, and then mixing the several single-target beads into a mixture bead solution. It is possible to apply more than one antibody to a label bead, for example pan-[G+] and pan-[G−], or some specific set of antibodies that make up a desired set, for example all prevalent G+ bacteria, or all bacteria susceptible to a particular antibiotic, or an antibody for each of the most prevalent fungi. This may be desirable in order to reduce the background bead concentration, as compared to a concentration of beads for each specific targeted organism.

In a further embodiment, the G+ label solution contains beads with multiple antibodies attached, for example 10 different antibodies on each bead, or 10 types of beads with each subset of beads having only one of the 10 antibodies attached. Alternatively, beads are labeled with a pan-bacterial antibody may be mixed with additional beads labeled with other antibodies, to facilitate the labeling of particular targets. This embodiment can be used, for example, where the pan-bacteria label does not adequately attach to some subset of the pan-bacteria set.

Exemplary sample fluids that can be used include, but are not limited to biological specimens such as blood, urine, CSF, or other fluids; swab samples from skin, wound, or other body sites may be tested by washing to entrain the sample from the collector into a fluid; and semi-solid samples, such as fecal samples, can also be processed by appropriate sample dilution in a liquid.

Using the methods of the invention, it is possible to determine if a specific bacterium is present in a sample fluid, by attaching antibodies specific for a specific bacterial strain to a bead with a particular signal characteristic. For example, a bead with a particular amount of iron can be used, which produces a particular signal level. In this way, the presence of many different types of bacteria may be determined in a sample, and the presence of a particular bacterial type, or many types can be done in a single measurement cycle. The number of different types of bacteria that may be detected depends on the number of discrete detection levels that may be determined given the signal discrimination of the detection process, dictated for example by the signal-to-noise ratio and the dynamic range of the measurement. For example 10 individual signal levels may be detected, such that 10 bead types (or ten distinct multiplicities of bead labels) may be identified, and thereby 10 different types of bacteria may be identified. Labeling of different entities may also be differentiated by the number of labels attached to each, rather than a selection achieved via specific binding.

In order to increase the number of levels detected, it is possible to divide the test sample, for example 10 ml, into several subsamples, for example 2 ml each, and have 5 separate labeling stages to provide for identification of 50 distinct individual bacteria, in this particular example. The separate testing of each individual subset might be done by having a separate detection coil for each subset, or have valves that sequence the subsamples through the detection coil. It is also possible to use a multiplicity of differently-sized NMR coils, or different flow rates, or different magnetic fields optimized to detect different magnetic labels. The fluid under test can be made to pass through each detector sequentially, so that a multiplicity of distinct entities can be detected.

One example of a testing scenario on human blood is:
1) Run Screen Module for G+, G−, Fungi
2) Example test result: G+, 4 CFU/ml; Fungi, 8 CFU/ml
3) Run G+ Identification Module
4) Example Result; MRSA, 4 CFU/ml
5) Run Fungi Identification Module
6) Example Test result: *Candida albicans*, 8 CFU/ml In another example, all tests are run from a single module, wherein the subtests run are dependent on the preceding results:
  1) Load sample, 10 ml
  2) Run 2 ml through G+, G−, Fungi subsection
  3) Example Test result: G+, 4 CFU/ml; Fungi, 8 CFU/ml
  4) Run 2 ml through G+ subsection
  5) Example Result; MRSA, 4 CFU/ml
  6) Run 2 ml through Fung subsection
  7) Example Test result: Candida albicans, 8 CFU/ml In this way the number of possible identified species or pathogens depends on the number of subsection tests, and the number of discrete detection levels that may be produced. The module may also be designed to perform more than one detection protocol in parallel. For example, the device might rapidly test the sample for the presence of high concentrations of targets, perhaps sequentially, while at the same time initiating a longer search for very rare targets of the same or of a different nature. This parallel processing may proceed through the use of multiple coils or a single detector coil, operated in a multiplexed way.

An additional feature of the detection process is the measurement of the concentration of the pathogen, for example bacteria, such that the nature, status, and progress of the infection may be determined and monitored using test samples obtained from a given patient at different time points.

In addition to detecting pathogens, molecular targets such as proteins may be detected in the device. Individual molecules can be detected if they have a bead attached, since the detection amplification process for molecules is identical to that of cells or organisms. Protein concentrations can also be measured in a concentration mode of detection. Any other entity to which an antibody can be raised may also be targeted, for example viruses (HIV, HepA,B,C) or Prion diseases (vCJD, TSE). The device may be used to detect mammalian cells, for example cancer cells, in either rare entity or concentration mode. Thus the technology may be used to detect, for example, bladder cancer cells in urine, or circulating cancer cells in blood, or fetal cells in maternal blood or amniotic fluid.

While operating in rare entity detection mode, the device is able to sequester the detected targets into a very small volume (few to 100 mL, or 1 uL, etc.). This collection of targets will thereby be concentrated. The collection volume can be small enough to enable the rapid location of the targets on a microscope slide, or the rapid processing of only the small volume in subsequent processes or devices. The collected, concentrated targets may be further analyzed in the device, either in the coil used to detect them in the first place, or in a separate detection circuit or method. Alternatively, the collection volume may be located on the module in such a way as to facilitate the introduction of that volume into a second magnet and detector system optimized to study the volume as a stationary NMR sample. These further NMR studies may be precise measurements of relaxation times, spectroscopic identification of objects or molecules, including the identification of properties or features of the labels that were not discernable during the rare entity detection phase of the device's operation.

The clinical application of the methods and devices of the invention may be to take the place of blood culture, which is presently the method used to determine if there are pathogens in blood. Blood culture takes a significant amount of time to produce a result, which nevertheless exhibits a high degree of variability, has a significant rate of false negative, and only determines the presence of a pathogen, not the identity of the pathogen. Further identification steps must be employed to determine the actual pathogen type, including steps performed by a person. For example, a technician will take a sample from a positive blood culture bottle, do preparation and staining of the sample, and do a preliminary qualitative analysis of the pathogen (ie: "Gram-rod", or "Gram+cocci"). Further identification and testing for antibiotic susceptibility must be performed in additional processing steps and instruments. It is common for the process to take 1 to 2 days, and it is possible for the process to take more than 5 days in some instances. A device based on the disclosed technology can provide for the detection of pathogens and also the identification of the pathogen. Because there are antibodies specific to strains that are indicative of antibiotic resistance, the disclosed technology is capable of doing detection, identification, and susceptibility determination (through strain identification) of pathogens, e.g. bacteria. Thus the technology can provide a clinician with a result that allows the timely identification of the optimal antibiotic for the pathogen that is present in the sample.

Such a device would be very useful clinically, as the progression of infectious diseases is frequently much faster than the time periods associated with blood culture, or culturing of other samples. For example, bacterial meningitis is identified through the examination of a sample from the CSF. Although these samples may be cultured, bacterial meningitis has such a short mortality period that culture is unable to be used for detection and identification. Staining and microscope examination of the sample must be performed, and this is not an optimal way to detect and identify bacteria. GBS testing of women about to experience child birth is another example where the swab sample is not able to be cultured before the result is required for clinical use.

In these cases, and many others, the disclosed device is able to produce detection and identification in a time that is appropriate to the clinical use.

The disclosed technology is also able to detect proteins that are associated with pathogens, or with the response of the host to pathogen or inflammatory responses that are associated with a disease, or an infection, or some other indication of the status of a disease or health in general. There are for example many host response proteins that may be indicative of the development and progress of sepsis. Although the relevance of these proteins is being debated at this time, the disclosed technology can detect these proteins, through magnetic labeling and detection, and thus identify and quantify the protein in the tested fluid. There may therefore be a correlation determined such that a particular combination of proteins, or their concentrations are indicative of a particular disease state or progress. Or the concentrations of the proteins taken also with the detected pathogen may indicate a particular disease state or progress. Or some set of parameters, such as other clinical information and diagnostic assays or measurements, taken with the concentration of proteins, and/or with the identified pathogen, may indicate a disease state or progress. This may include the time dynamics of said measurements. The device is be capable of detecting proteins at significantly lower concentrations than other techniques. In principle, one molecule in 10 mL is possible. If more than one bead can be attached to the protein molecule, then a homogeneous assay approach for protein detection is possible.

One embodiment of the technology involves the use of affinity chromatography to concentrate the target entity, be it bacteria, cells, viruses, proteins, protozoa, prions, nucleic acids, or other biological material of interest, on a column modified to contain a capture agent which recognizes the target. For example, a protein (bovine serum albumin; BSA) is modified with a hexa-histidine peptide tag. This protein can then be bound to either a nickel-agarose, or a cobalt-agarose column where the histidine residues recognized the nickel or cobalt ions and bind the protein to the column. The column is then probed with magnetic particles to which an anti-BSA antibody is attached. The particles bind to the immobilized BSA. To release the bound particles, the column is eluted with imidazole, which competitively interferes with histidine binding to the metal ions. The result is that the Bead-Ab-BSA complex is released from the column in a very small volume. This released material then enters the NMR microcoil and can be detected by means of the magnetic bead's effect on the transverse ($T_2^*$) relaxation time of the background water in the sample. Similar performance can be achieved if the column contains a bound target protein that recognizes, for example, sugar groups, such as a lectin, of which Concanavalin A is a prototype. The column-bound material can then be released by eluting the column with the sugar to which the lectin bound, in the case of Concanavalin A, this release agent is glucose. There are many lectin/sugar combinations which can be used for this purpose. Other affinity media include antibodies from one species which are directed against antibodies from a different species, for example, antibodies raised in goats can be recognized by rabbit, anti-goat antibodies. Other affinity media include, but are not limited to, streptavidin/biotin, protein A/antibodies, and dextran/glucose.

The column may be a matrix of material that has the antibody for the target of interest attached to the matrix, for example a specific target such as a protein, a fungus or bacterium or a broader class of targets, such as all G+ or G− bacteria. As an example, once the target has been attached to the column, the flow of the sample may be stopped, and the column washed of excess materials, and then a fluid containing magnetic label beads may be flowed through the column. These beads may have the same antibody as the column, or may have some other antibody. For example, if the column has G+ antibody, the labels may have an antibody for MRSA, and thus only attach to MRSA bacteria, if present. Or there may be several different types of beads, for example each specific type with a different characteristic signal and an antibody to a different target G+ bacteria. In this way all G+ bacteria are collected, and then the determination of the type of G+ bacteria is made through the particular label antibody that causes specific attachment of a particular bead type that has a detectable characteristic signal.

The sample fluid may also be caused to flow through several different affinity columns, in parallel, or more preferably in series, in order to attach a particular pathogen type in each separate column. For example three affinity columns might be used in series, one for G+, G−, and fungi. The sample, for example blood, is caused to flow through each in succession, and in a loop several times, until the probability of attachment is acceptable. Thereby if there is G+, G−, or fungus separately or together in the sample, the pathogen is attached to the associated column. After the attachment to the column, the sample flow may be turned off, a wash step may be used to remove unbound material, and then a solution with label may be flowed through the column. The bead solution flowing through the column allows the beads to attach to the pathogen for which the bead has antibody. Once the bead solution has flowed through the column sufficiently to have an acceptable level of labeling probability, for example in a loop, the bead solution flow is stopped. Then the column is washed, and subsequently eluted with a reagent that causes the attached pathogen, with the label, to release from the column and pass through the detection circuit.

The label solution, containing magnetic beads, can be flowed through the columns in series or in parallel. The magnetic beads may have a specific antibody attached in order to target particular bacteria, as described herein. For example, there may be 30 different levels, 10 each of types of G+, G−, and Fungi. In this way the solution containing the beads may be flowed through the affinity filters in series, and the labels attaching to the specific pathogen for which the bead has antibody.

In another embodiment, there may be 10 levels only of discernable signal differentiation (for example based on signal to noise of the detection method), and in this case 10 specific beads may be used in each of the 3 affinity filters. The solution for each column is processed separately, and the flow through the detection circuit is multiplexed, such that the determination of the type of pathogen includes the signal level from the bead, for example level 7, and the column from which the solution originated, for example, the fungi column. This provides 30 distinct identifications, using only 10 bead characteristic levels.

Figure 12:
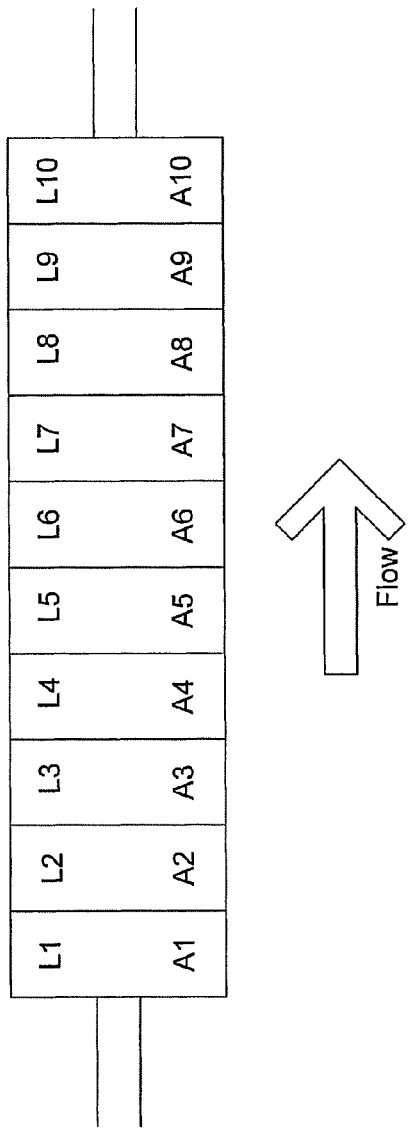
FIG. 12 is a graphical representation of a layered affinity column for use with the invention.

It is also possible to have distinct layers in the affinity column such that the target pathogens are attached to a specific region. For example there may be 10 layers in a column with each layer having a specific antibody associated with it (FIG. 12). The bacteria would then attach to the associated region, and be labeled. The release wash would then produce a flow of liquid through the detection coil that has a certain profile, in time, associated with the position on the column. A detection event from the fluid associated with a particular level would indicate a certain bacteria. Thus the time from wash flow initiation to the detection event would associate the fluid to a particular region on the column.

The layers could also be for a general type of pathogen, and the bead labels provide further specificity. For example, there might be three layers, one each for G+, G−, and fungi, and there may be 10 magnet labeled beads, each with a specific signal characteristics and antibody. One level is associated with 3 antibodies, one particular species or strain of G+, G−, and fungi. With the pathogen attached to the layer, the bead solution is caused to flow through the column, labeling the specific bead to the target pathogen. When released, identification is achieved for a particular pathogen by the signal level, and the time from the release, which is related to the layer from which the bead originated.

Figure 13:
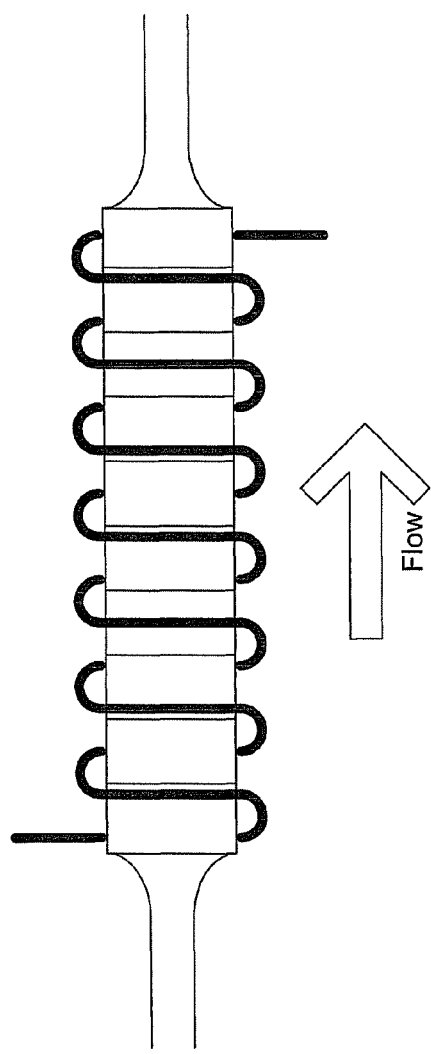
FIG. 13 is a graphical representation of a layered affinity column integrated with a microcoil for use with the invention.

Additionally, the layered column might be held within the detection coil, and thus the identification can be made by the layer associated with the detected signal (FIG. 13). Using MRI based techniques, the location of the signal may be determined, and thereby the associated layer. As previously stated, a multi layer affinity column may be constructed. In this case the label beads may have a specific antibody, or general antibody, as long as the pathogens of each layer are labeled sufficiently for detection. The specificity is attained by the specific antibody associated with a layer, or a position on the column, and a signal strength associated with a particular label that has antibody for a specific pathogen. For example, a affinity column layer may have a pan G+ antibody to localize any G+ bacteria, and then specific label beads with characteristic signal strengths for the various G+ bacteria would label the individual targets. Identification is determined by the location on the column and the signal strength associated with the labels for a particular G+ target bacteria.

If an affinity column step is not used, then it is preferred that the magnetic beads are multivalent so that they cross-link targets, or multiple beads are attached to a single target entity, and the NMR signal arises from the differential effect of the aggregated vs. dispersed magnetic beads on the surrounding water.

Blood Safety

The screening of donated blood in a blood bank requires the detection of small amounts of a number of potential pathogens. Bacterial contamination is acknowledged as the most frequent transfusion-transmitted infection of all blood components. However, parasitic, viral, host-leukocyte, and prion contamination are also important players in the transmission of disease via transfusion. The disclosed methods and devices of the invention can provide ultrahigh-sensitivity detection of each and every one of the following blood-supply threats.

Bacteria. Currently, the human blood supply is subject to several safeguards, however, despite a battery of tests for pathogens, only a single bacterial strain, *Treponema pallidum*, the bacterium that causes syphilis, has historically been selected for routine screening. Due to the absence of bacterial-monitoring, transfusion-associated bacterial sepsis is estimated to occur in 1 case per 6 contaminated units transfused, with fatality occurring in up to 25% of these cases. In the UK, data from the 1996-2001 Serious Hazards of Transfusion (SHOT) study indicated that 60% of all reported cases of transfusion-transmitted infection were attributed to bacterial contamination. In France, data from the Haemovigilance Network reported 15% of transfusion-related deaths between 1996-1997 were due to bacterial contamination. Although automated culture methods are available for detecting the presence of different classes of bacteria, these systems have limitations, including sampling errors, false-positive and false-negative results, and long lead times of more than 48 hours for reporting.

Bacteria are a particular problem in platelet concentrates because of their storage at room temperature, which favors rapid bacterial growth. In addition, bacteria are an under-reported problem in platelet transfusions. The estimated incidence of bacterial contamination is 1 in 2000 random donor or apheresis platelet units.

Parasites. In addition to bacteria, other blood supply threats include parasites. Detection tests are not yet developed for the presence of any recognized parasites in donated blood. With the increase in global travel and migration over the last 20 years, blood-borne parasitic diseases such as malaria, Chagas' disease and Leishmaniasis have become more common in blood transfusions. Parasite screening tests are not routinely used, and notoriously-unreliable donor interviews remain the primary defense against such infections.

Globally, malaria is estimated to infect more than 400 million people every year in tropical regions. This disease, transmitted through blood transfusion, accounted for 91 cases in the US between 1963 and 1999. Currently, blood donors who have visited areas in which malaria is endemic may be deferred from donating blood for six months.

*Trypanosoma cruzi*, the causative agent of Chagas' disease, is endemic in much of South America. Although the disease can be transmitted through blood transfusion and has been documented in the US and Canada, routine screening of blood for *T. cruzi* is not performed. Studies in Los Angeles, Calif. have indicated that in some regions as many as 1 in 7,500 blood donors show evidence of infection.

Leishmaniasis, caused by the *Leishmania* sp., is a serious illness endemic to subtropical regions. Recent studies of *Leishmania*/HIV co-infection have revealed that the true prevalence of *Leishmania* in Spain and Southern Europe may be under-reported and the parasite can pose a serious health risk to immunocompromised patients.

Viruses. Not only bacteria and parasites, but also viruses and prions contaminate the human blood supply. Viral safety is also an important concern for manufacturers of biopharmaceutical products. Although as many as 25 known viral pathogens may be present in blood, only a handful of viruses, including HIV, HCV, and HBV, are required to be screened after collection. The need for scrutiny has not kept up with the infection incidence. For example, over the past two decades, Table 1 shows the new viral threats to the blood supply that have been identified.

TABLE 1

Year of detection of Viruses.

| Year | Virus |
|---|---|
| 1980 | HTLV-1 |
| 1982 | HTLV-2 |
| 1983 | HIV-1 |
| 1986 | HIV-2 |
| 1986 | HDV |
| 1989 | HCV |
| 1990-91 | HEV |
| 1994-96 | HHV-8 |
| 1995-96 | HGV |
| 1997 | TTV |
| 1999 | SEN-V |
| 2002 | BDV |
| 2002 | WNV |
| 2003 | SARS* |

One of these, West Nile Virus (WNV), provides a notable example of the ability of pathogens to migrate across continents and emerge as threats in new regions. Over the last 40 years, WNV has caused sporadic outbreaks of human disease in Europe. The most recent European outbreak in humans occurred in 1996-7 in Bucharest, Romania, and involved more than 500 recorded cases, with a fatality rate of 10%. Moreover, since 2002, a new strain of this virus has spread rapidly through the United States, with 12,375 cases of human WNV infection reported by Feb. 18, 2003, and 466 associated deaths. Furthermore, as of April 2003, it had been confirmed that 23 cases of WNV illness had developed in patients as a result of infection from a blood transfusion or organ transplant.

Although most of the routine screening tests in common use are directed against viral pathogens, the blood supply still remains vulnerable to many known viral diseases. Cytomegalovirus (CMV) is such a common infection that it is not routinely screened due to its high prevalence (from 40-100% in Western adult populations). However, CMV can pose a serious threat to immunocompromised individuals, who receive CMV-seronegative blood units from a limited supply. Although leukoreduction has been proposed as an alternative to the use of CMV-seronegative units, some studies have indicated that leuko-filtration is not completely effective at preventing transmission of CMV. Parvovirus B19 is another virus which is widespread (up to 70-90% estimated seroprevalence in adults), and is not included in the panel of blood bank screening tests. B19 infection can be hazardous for certain populations such as those who are immunocompromised, sickle cell/thalassemia patients, and pregnant women.

Prions. Prion diseases, such as Transmissable Spongiform Encephalopathy (TSE) and variant Creutzfeldt-Jacob disease (vCJD) are caused by the misfolded prion protein (PrPSc). Prion diseases, can spread through the food supply, organ transplants, contaminated medical instruments, the blood supply, or pharmaceuticals made from animal products. Recently, two patients died of variant Creutzfeldt-Jacob disease from blood transmission from an asymptomatic infected individual. A rapid blood screening test for prion diseases is needed. Prion peptide reagents, that bind the pathogenic prion protein isoform, PrPSc, have been coated on magnetic beads to effectively capture and concentrate human PrPSc from brain homogenates. Rapid blood screening tests of PrPSc from serum can use the prion-specific antibody 15B3. This magnetic prion assay can achieve the sensitivity and throughput required for screening human blood samples.

Donor Leukocytes. The presence of viable donor leukocytes in donated blood has long been recognized as a source of risk for recipients. Transfusion-associated graft-versus-host disease (TA-GVHD) caused by proliferation of donor T-cells in the recipient may carry a mortality rate as high as 84%. In addition, cytokines released by leukocytes during unit storage can cause febrile non-hemolytic transfusion reactions. Leukocytes can also harbor latent viruses such as CMV and HTLV. If one detects leukocytes, one can utilize current safeguards against leukocytes. These often take the form of gamma irradiation, which is used to inactivate donor leukocytes. Leukoreduction is another standard tool for reducing risk to recipients, and leukofiltered units contain a much-reduced number of white cells.

Example 3

Construction Methods

Winding coils—As our goal is to construct small portable NMR systems at reasonable cost, we seek a method for manufacturing microcoils that is significantly simpler than the focused ion beam techniques used to construct the coil for our first experiments. The classic coil construction method is "hand-winding" using standard (usually enameled) wires. A simple gear-synchronized device for accurately winding very small coils on pulled pipette tips has been previously described [17]. The main requirements of any such device are methods for holding the sample tube and rotating it and for controlling the position of the very fine wire as it is taken up on the tube. We find that these requirements are readily met through the use of a miniature lathe [Taig Tools, Chandler, Ariz.] in conjunction with optical fiber chucks [Newport] appropriately sized to hold micro-capillary tubes [Vitrocom]. The tube is mounted to the headstock of the lathe using the fiber chuck. One end of the wire is taped to the fiber chuck while the other is taped to a support whose position is controlled by the saddle and cross-feed of the lathe. A 7×-30× dissecting microscope is used to visually monitor the coils as they are wound by gradually turning the headstock and repositioning the cross-feed of the lathe by hand. The capillary tubes are very flexible, and their deflection while winding aids in maintaining the proper tension on the wires [typically 50 gauge enameled copper, California Fine Wire]. When finished, the coil is secured to the tube using standard five-minute epoxy. With minimal practice, coils can be wound in about 15 minutes.

One key to this rapid coil construction lies in our choice to close-wind our coils. Generally, NMR practitioners assume that coils should be wound with some space between the turns [25,27] in order to avoid strong proximity effects that can increase the high-frequency resistance of the coil windings, leading to excess electrical noise. However, we are operating our coils at rather low frequencies, low enough that the diameter of our wire is only about 2.5 times larger than the radio frequency (RF) skin depth. Furthermore, the enamel layer on our wire is about 6 µm thick, yielding a measured 37 µm turn-to-turn spacing. (The diameter of 50 gauge bare copper wire is 25 µm.) Under these conditions, the RF resistance is enhanced over the DC resistance by 4% due to the skin effect and only an additional 4-11% due to the proximity effect [1]. On the other hand, a close-wound coil has the highest possible pitch and hence the highest signal detection sensitivity. The high performance of close-wound micro-coils has been demonstrated experimentally [17]; the SNR was found to be maximal for minimal turn spacing. However, as discussed herein, this practice has been discouraged by NMR practitioners as leading to strong proximity effects that ultimately lead to excess noise [25, 27]. One practical benefit of close winding is that it greatly reduces the need to accurately control the wire during coil construction.

Designing the probe circuit—In our earlier work with microcoils, we introduced the counterintuitive idea of using a large, fixed-value auxiliary inductor in the resonant circuit of the probe. While not strictly necessary for the "large" (550 µm diameter) coil in our earlier work, such an auxiliary inductor is a practical necessity for smaller coils operating at low frequency. There are at least two benefits of the auxiliary inductor. Very small sample coils cannot be resonated at the low operating frequencies typical of permanent magnet based NMR devices without the use of very high capacitances. Either a physically large variable capacitor (contrary to the goal of miniaturization) or a large amount of fixed capacitance in parallel with a variable capacitor (which reduces the tuning range, awkward given the field drifts of permanent magnets) would be required. Furthermore, it is difficult to construct a resonant circuit for a microcoil without introducing paths for circulating currents whose inductances are larger than the branch of the circuit that contains the microcoil. This is especially true for circuits that contain more than one tuning capacitor in parallel. Under such conditions, the circuit as a whole may resonate at the desired frequency, but the current paths in this resonant mode will largely avoid the branch of the circuit containing the sample coil. An auxiliary inductor, placed in series with the microcoil, both forces the resonant current to flow through the sample coil and reduces the need to include numerous capacitors and their multiple, competing current paths.

The auxiliary inductor raises the Q of the probe circuit. For high resistance microcoils, the resulting Q is still modest (~10-20), rendering the electrical resonance easy to detect without presenting difficulties with respect to probe stability or excessive ring-down.

Proper design of the auxiliary inductor insures that it does not degrade the SNR performance of the probe over what theoretically can be achieved without the auxiliary inductor. One key idea is that the auxiliary inductor should not contribute to the resistance of the resonant circuit. It is stray resistance that degrades the performance of NMR circuits, not stray inductance. [27] Once the microcoil has been wound, its RF resistance can be measured or calculated, and this value serves as the starting point for auxiliary inductor design. Ideally, the RF resistance of the auxiliary inductor should be much less than that of the microcoil. If the inductor adds 10% to the circuit's RF resistance, the SNR is reduced by 5%. To minimize its resistance, the auxiliary inductor is wound using large diameter wire. For our probes, we typically choose 14 gauge copper wire (diameter=1.63 mm). Given that the current is carried only at the outer surface of the wire, we can calculate the longest piece of such wire consistent with our goal of low resistance. It can be shown that the maximal inductance that can be constructed from a wire of length $l_{wire}$ is achieved with a coil of radius:

$$r_{coil} = \sqrt{\frac{25 l_{wire} k d_{wire}}{46\pi}} \quad (1)$$

where $d_{wire}$ is the wire diameter, and $kd_{wire}$ is the turn-to-turn spacing (k=1.3, typically). Our microcoils have RF resistances that are typically 0.2-1.0Ω at our operating frequency (44 MHz), and the calculated auxiliary inductors are conveniently sized (radius 0.3-0.6 cm, 2-4 turns).

With the auxiliary inductor properly constructed, we build the remainder of our NMR probe circuit. For example, a small rectangle of acrylic sheet (roughly 4 cm×3 cm×0.7 cm) can serve as a mechanical support. Small pieces of adhesive-backed copper foil are cut and placed on the acrylic block so that the sample coil, auxiliary inductor, and tuning and matching capacitors can all be mounted on the block. The capillary tube on which the sample coil is wound is glued into two lengths of flexible tubing (we have used PEEK and Radel) using standard five-minute epoxy. This structure is in turn glued to the acrylic block so that the fragile capillary tube is isolated from mechanical shocks transmitted along the flexible tubing. The auxiliary inductor and capacitors are soldered to the copper foil, and the acrylic-block-mounted module is then installed in a shielded probe body (we have used cast aluminum boxes, or plastic boxes covered with copper foil). As we show herein, these very simple and crude probe construction techniques yield NMR detectors that achieve optimal performance.

Results

Using the methods described herein, we have wound a series of microcoils of different sizes, as detailed in Table 1.

TABLE 1

Microcoil probe parameters.

| Capillary OD/ID (μm) | Turns | Length (μm) | Calculated inductance (nH) | Sample diameter (μm) | Sample volume (nL) |
|---|---|---|---|---|---|
| 170/100 | 4 | 148 | 3 | 100 | 1.2 |
| 250/150 | 5 | 185 | 7 | 150 | 3.3 |
| 330/200 | 6 | 222 | 13 | 200 | 7.0 |
| 550/400 | 17.5 | 648 | 120 | 400 | 81 |

We designate the capillary size with two numbers, the outer diameter and inner diameter of the tube, in micrometers. The length of the coil is calculated from the number of turns and measured total wire diameter of 37 μm. The inductance is calculated using the standard formula. [25] The three smallest coils were built into probe circuits that contained an auxiliary inductor: 3 turns of 14 gauge bare copper wire with a 14.5 mm diameter (calculated inductance 150 nH). The probe circuit for the largest coil did not employ an auxiliary inductor.

To determine the SNR, we performed a single-pulse experiment and acquired a single two-channel free induction decay (FID) signal. For all of our experiments, we used a 1.04 Tesla permanent magnet with a 5 cm clear gap equipped with linear gradient/shim coils. This is hardly a portable magnet; however it has the same field as our 0.6 kg 1 Tesla magnet, and the much larger gap facilitates rapid detector prototyping. The NMR console was a compact imaging system from MRTechnology (Japan). The sample fluid was Magnevist(Gd)-doped water ($T_1$~430 ms) delivered by syringe though the tubing attached to the capillary. To determine the SNR, the detected signal was corrected for baseline offset and then mathematically adjusted to be on resonance with all of the signal power in one of the channels.

TABLE 2

Measured performance and resistance of microcoils.

| Probe | Observed SNR (±10%) | Detector bandwidth (Hertz) | Line width (Hertz) (±10%) | Resistance (Ω) (±0.01 Ω) | Power (μW) (±15%) |
|---|---|---|---|---|---|
| 170/100 | 8.6 | ±250 | 1.5 | 0.43 | 7.6 |
| 250/150 | 38 | ±250 | 1.5 | 0.44 | 14 |
| 330/200 | 63.5 | ±250 | 2.8 | 0.57 | 20 |
| 550/400 | 485 | ±250 | 5 | 1.61 | 25 |

The noise value was taken to be the standard deviation of the data in the baseline region, the last 50% or so of the data set. The signal was determined by extrapolating the FID back to zero time. Extrapolation was necessary because our narrow bandwidth filters ring for a significant time after the RF pulse. (Our console, designed for imaging, is not optimized for operation at our narrow bandwidths and is not equipped with a adjustable receiver muting circuit.) The measured SNR values are given in Table 2 and have an estimated uncertainty of 10%, which comes from both the extrapolation and from the uncertainty in the standard deviation of the baseline data.

The minimum achieved line width (FWHM of a Lorentzian fit to the Fourier Transform of FID data) is also given in Table 2. The probe was carefully positioned in the most homogeneous location in the magnet, and the linear shims were adjusted to maximize the lifetime of the FID (and optimize its shape). The shims typically provided a 2-5 fold reduction in the line width. The line widths reported in Table 2 are the narrowest we achieved. Typically, careful placement of each probe into the same position in the magnet allowed the line width to be reproduced to within 20%. Note that the FID data used to determine minimum line widths were not the same as those used to determine maximum SNR.

TABLE 3

Calculated resistance and SNR performance of microcoil probes.

| Capillary | $R_{DC}$ (Ω) | Skin depth factor | Proximity factor | $R_{RF}$ (Ω) | Auxiliary inductor (Ω) | Total (Ω) | Calculated SNR |
|---|---|---|---|---|---|---|---|
| 170/100 | 0.43 | 0.040 | 0.039 | 0.45 | 0.047 | 0.50 | 13 |
| 250/150 | 0.44 | 0.040 | 0.044 | 0.47 | 0.047 | 0.52 | 36 |
| 330/200 | 0.57 | 0.040 | 0.050 | 0.61 | 0.047 | 0.66 | 67 |
| 550/400 | 1.61 | 0.040 | 0.114 | 1.82 | none | 1.82 | 474 |

The DC resistance of the microcoils, given in Table 2, was measured with a benchtop DMM (Fluke 8840A/AF) operating in two-wire mode. The resistance of the microcoil together with the leads connecting it to the rest of the probe circuit was measured. The DMM lead resistance of 0.040±0.005Ω was subtracted from the measured values, which have an overall uncertainty of about 0.01Ω. The rightmost column in Table 2 gives the RF power required to produce the 100 μs π/2 pulse in our experiments. This power was determined by measuring the peak-to-peak voltage of the pulse seen by the probe circuit by routing this pulse to a 50Ω-terminated oscilloscope. The uncertainty in the measurement comes from the roughly ±10% uncertainty of reading the oscilloscope screen.

Discussion

Comparison to original microcoil results—We have achieved an SNR of 485±50 with the 50 gauge wire-wound 550/400 microcoil using a detection bandwidth of ±250 Hz. To facilitate comparison to our previous focused ion beam (FIB) coil result, we re-analyzed the previous data using the method described herein. (Henceforth, we refer to this coil as the "FIB-coil.") The re-analyzed SNR value for the FIB-coil was 38±2 in a detection bandwidth of ±5000 Hz. At this bandwidth, our wire-wound coil should give an SNR of 108±12. To account for the different lengths of the sample volumes, we note that extending our wire-wound coil to the 2.1 mm length of the FIB-coil would enclose 3.24 time more volume while increasing the resistance by the same factor. We therefore scale the SNR by $\sqrt{3.24}$ and calculate that a wire wound coil of the same size as the FIB-coil should yield an SNR of 194±20. Hence, the wire-wound coil achieved a 5-fold (5.1±0.8) improvement in SNR performance over the FIB-coil. The DC resistances of a wire-wound coil that is the same length as the FIB-coil is 5.22Ω, compared with the 5.42Ω of the FIB coil. The pitch of the wire-wound coil is two times finer than the FIB-coil. These two differences account for a factor of two improvement in the SNR. The FIB-coil's probe circuit contained other sources of resistive losses, including the 45 cm quarterwave cable and the long (10 cm) leads between components in the two shielded boxes. These resistances are eliminated in the present design, which helps account for the observed 5-fold improvement in SNR.

The line width achieved in the wire-wound 550/400 probe was 115 ppb, a factor of 2 worse than our FIB-coil result. In our previous paper [26], we speculated that the narrow line had been achieved due to the high cylindrical symmetry of the FIB-coil. Due to the following experiments, we now believe that the main reason was the relative lack of metal present in that coil.

Before winding the 550/400 coil described in Table 1, we wound a 20-turn coil with 40-gauge enameled copper wire on a 550/400 tube. This coil was 1.5 mm long and contained a sample volume of about 190 mL. The turn-turn spacing was 80 microns, nearly the same as the FIB-coil, while the volume was about ¾ of the FIB-coil's sample volume. However, the narrowest line achieved in this 40-gauge probe was 1 ppm, nearly 20 times worse than the FIB-coil. Since a narrower line had been achieved over a larger sample volume in the FIB-coil, homogeneity of the background magnetic field can be ruled out as a factor limiting the line width. A series of modifications were made to this 40-gauge probe in order to ascertain the source of the excess line broadening. Guided by the original FIB-coil probe, in which no piece of the probe circuitry or support structure came within 3 mm of the sample volume, new versions of the 40-gauge probe were constructed in which the support structures, electrical circuitry, and fluid handling tubing were all moved well away from the sample volume; no improvement in the line width was observed. The final modification was to replace the 40-gauge with 50-gauge wire. This 50-gauge coil achieved the much smaller line width given in Table 2.

The 550/400 coil wound with 50-gauge wire yielded a line width a factor of 2 worse than our original FIB-coil result, while the 40-gauge coil was a factor of 10 worse than the 50-gauge coil. These line width differences correlate very well with the cross-sectional areas of the wires in each of these coils, 4900 $\mu m^2$, 490 $\mu m^2$, and 325 $\mu m^2$ for the 40-gauge, 50-gauge, and FIB-coils, respectively. (The wire-wound coils were copper. The FIB coil was gold, 3 times more diamagnetic than copper, over a very thin chromium layer, which would compensate for the gold to some extent.) Due to the skin-depth effect, only the outer surface of the 40-gauge wire (an effective area of 250 $dm^2$) carries current, so most of the copper in that wire is "wasted." This excess copper, although it would not affect the SNR performance of the coil [Peck 1995][1], affects the homogeneity of the field in the sample volume. It appears that the presence of copper near the sample volume should be minimized in order to achieve the highest resolution, indicating that wires much larger than the skin depth should be avoided. Of course, susceptibility matching techniques [3,6] may be employed to overcome the distortions of the field due to the wires, but these would complicate our device.

Performance of smaller coils—As shown in Table 2, the resolution achieved in the three smallest coils is extremely good, approaching 30 ppb using only linear shims. Furthermore, the SNR is high enough that the FID is visible in a single shot, even in the smallest coil's ~1 nL volume. It is clear that our probe circuit design and simple, fast, inexpensive construction methods produce useable NMR detectors. However, we may ask if these detectors are performing optimally.

The SNR value we expect from these coils and probe circuits can be calculated using [1]

$$SNR = \frac{k_0(B_1/i)v_s N\gamma\hbar^2 I(I+1)\omega_0^2/3\sqrt{2}k_B T}{\sqrt{4k_B TR\Delta f}} \quad (2)$$

where $k_0$ is a constant that accounts for geometric effects associated with irregularity of the $B_1$ field produced by the finite solenoid as well as non-uniform excitation of the spins in the sample volume. $(B_1/i)$ is the efficiency of the coil in generating $B_1$, and for a solenoid it has the value $\mu_0 n$, where $\mu_0 = 4\pi \times 10^{-7}$ Tm/A and n is the turns per unit length. $v_s$ is the sample volume, $N = 6.7 \times 10^{28}/m^3$ the number density of hydrogen nuclei in our water samples, $\gamma = 2.675 \times 10^8$ radians/sec/T is the gyromagnetic ratio for hydrogen nuclei, I=½ for hydrogen, $\omega_0 = 2.78 \times 10^8$ radians/s for hydrogen nuclei in our field, T=297K, R the high frequency resistance of the LC resonant circuit, and $\Delta f$ the detection bandwidth. $k_0$ is the only parameter that cannot be measured or calculated easily. It should have a value close to but slightly less than 1.0, and should not differ substantially for our probes because they all have similar coil and sample geometries. We set $k_0$=1.0 in our calculations. Our detectors differ mainly in their sample volumes and resistances.

To calculate the expected SNR, we need to know the RF resistances of each element of the LC resonant circuit. The other parts of the probe, including the matching capacitor, the connections to ground, etc., play a much smaller role in contributing to losses in the circuit because the currents flowing in these sections of the probe are much smaller than in the resonant loop itself. We can calculate the resistances for each element of the resonant circuit by measuring their physical dimensions and considering that current will only flow in the region within a skin depth (10 μm in copper at our frequency) of the surface. For the 50-gauge wire, we measure the DC resistance of the microcoil and its leads; this value is given in Table 2 and repeated in the $2^{nd}$ column of Table 3 for convenience. We convert this DC resistance to a calculated RF resistance by using Tables 2 and 4 in Peck, et al., [1]. The RF resistance of the leads is raised by the skin depth effect, the strength of which may be found using Table 2 of Peck, et al. The factional enhancement to the DC resistance is about 4% for our coils, as shown in the third column of our Table 3. For the wires in a coil, the proximity effect also plays a role. The strength of the proximity effect depends on the number of turns and the coil aspect ratio, and can be calculated using FIGS. 2 and 4 in Peck, et al. The $4^{th}$ column in our Table 3 gives the fractional enhancement to the DC resistance due to the proximity effect in each of our coils. The $5^{th}$ column in our table is the total RF resistance, calculated by applying the enhancement factors to the measured DC resistance, with the proximity effect applied only to the fraction of the wire length in the microcoils. The calculated RF resistance of the auxiliary inductor is given in the $6^{th}$ column, and the total RF resistance of the LC circuit is given in the $7^{th}$. We find that the copper foil and the tuning capacitors contribute negligibly to the resistive losses.

One is faced with a number of definitional questions in linking measurements of absolute SNR to the theory [28,29]. Johnson's measurements were single-channel incoherent measurements of sub-megahertz voltage signals. Our NMR spectrometer processes the signal from the NMR coil to yield two channels of voltage data, each derived from a coherent combining of the NMR voltage signal with a local oscillator. In order to make the most direct connection with the older measurements, we process our two-channel signals by frequency- and phase-shifting them so that the entire signal appears in one of the channels. From this point forward, we treat this single channel as our entire signal, measuring the signal level from its amplitude at zero time and calculating the noise as the standard deviation of the values in the baseline, as described earlier.

A second consideration applies to the definition of the bandwidth $\Delta f$. In Nyquist's treatment, the rms voltage noise is white (that is, it has equal powers in every frequency interval $\Delta f$). The number 4 in the denominator of Eq. 2 is appropriate for an ideal filter that passes (without any weighting) only frequencies within the bandwidth $\Delta f$ and excludes all others. A single pole filter, with its Lorentzian transfer function, will admit more noise, and the factor 4 should be multiplied by π/2, assuming that Δf represents the FWHM of the Lorentzian. Our filters are eighth order, so they closely approximate the ideal filter.

The calculated SNR values in Table 3 agree very well with the measured values in Table 2, indicating that we accurately accounted for the losses in the probe circuit.

It is also possible to relate the SNR performance of the system to its characteristics in transmit mode. [27] If the current i that gives rise to $B_1$ flows through the resistance R responsible for the loss, then the power dissipated is $P=1R^2$ and Eq. (2) may be recast in the form:

$$P = \left(\frac{A v_s B_1}{SNR}\right)^2 \quad (3)$$

with $A=2.31 \times 10^{14}$ watt$^{1/2}$m$^{-3}$T$^{-1}$ (for $k_0=1$, $\Delta f=500$ Hz). A 100 μs π/2 pulse corresponds to $B_1=0.59$ G$=5.9\times10^{-5}$ T. Using Eq. (3), the sample volumes $v_s$ from Table 1, and the measured SNR values from Table 2, we calculate expected RF power requirements of 9.1 μW, 14 μW, 23 μW, and 52 μW for our four probes. The agreement with the measured values given in Table 2 is within uncertainties for the three smallest coils. Hence, the SNR measurements are consistent with the transmit performance of the probe, indicating that the SNR values are not corrupted by excess noise in our receiver. For the largest coil, the agreement is not quite as good, even when the uncertainties in the measured SNR and power are taken into account. We do not currently have a detailed explanation for this, except to note that the largest coil is substantially larger than the others and has a correspondingly much higher SNR.

Table 3 shows that our auxiliary inductor does not decrease the SNR performance unacceptably. We see that in the probes tested, the auxiliary inductor accounts for about 10% of the resistive losses, leading to a 5% decrease in the SNR that might be achieved without it. Removing the inductor therefore will not make a very large improvement in the SNR performance of these probes. However, without the auxiliary inductor, the probe circuit is much more difficult to construct and operate.

Building and testing a better probe—The agreement between the observed and calculated SNR in our first set of probes indicates that we have a good quantitative understanding of the factors contributing to the SNR performance. We now ask if we can improve the SNR.

This is equivalent to asking if there are stray resistances that can be removed. The first set of coils had rather long connections between the microcoils themselves and the remainder of the probe circuit, in order to avoid the homogeneity-degrading effects of large conductors too near the sample. Since these connections are made with the narrow gauge wire, they contribute substantially to the resistance (and hence noise) in our detector, without contributing signal. We have measured the lead lengths of our coils and then used the results of Peck, et al. [1] to calculate the separate contributions of the microcoils and the leads to the resistance of the LC circuit. The values are given in the 2$^{nd}$ and 3$^{rd}$ columns of Table 4. The 4$^{th}$ column gives the total calculated RF resistance of the coil and its leads, while the 5$^{th}$ column gives the value of this same quantity that we calculated based on the measured DC resistance (see Table 3). The last column gives the calculated RF resistance of the auxiliary inductor, also from Table 3.

TABLE 4

Contributions to the resistive losses in the microcoil probe circuits.

| Capillary | Microcoil (Ω) | Leads (Ω) | Total (Ω) | "Measured" Total (Ω) | Auxiliary inductor (Ω) |
|---|---|---|---|---|---|
| 170/100 | 0.097 | 0.35 | 0.44 | 0.45 | 0.047 |
| 250/150 | 0.17 | 0.22 | 0.39 | 0.47 | 0.047 |
| 330/200 | 0.26 | 0.29 | 0.55 | 0.61 | 0.047 |
| 550/400 | 1.29 | 0.31 | 1.60 | 1.82 | none |

Table 4 indicates that probes with shorter leads can achieve higher SNR performance. Shortening the leads requires bringing larger conductors closer to the sample volume. Given our experience with the 40 gauge wire and the 550/400 coil, we expect that the resolution will eventually be degraded as larger amounts of copper are placed closer to the sample volume. A compromise between resolution and SNR, informed by the requirements of the measurements to be performed, will govern the optimization of the probe circuit design.

Conclusions

We have shown that very small microcoils can readily be operated as NMR detectors in the low magnetic fields of permanent magnets, a new size and frequency regime for miniaturized NMR detectors. The close agreement in the measured SNR and the values calculated based on a detailed analysis of the sources of resistive losses in our NMR probes indicate that the simple construction methods we employ yield outstanding probes. In particular, the SNR performance confirms that the auxiliary "tuning" inductor does not degrade SNR performance. The detailed analysis of the resistive losses also points the way toward available improvements in SNR performance: reduction of the leads connecting the microcoil to the remainder of the probe circuit. However, reduction of these lead lengths must respect the fact that bringing more metal closer to the sample volume can readily degrade the field homogeneity.

Example 4

Tuning Coils

The example includes a LC resonance circuit that is appropriate for performing magnetic resonance experiments, among other beneficial purposes. The circuit has a microcoil, an adjustable tuning capacitance, and a tuning inductor. A microcoil having an inductance of 25 nH or less is often much smaller than a tuning inductor. The circuit elements are connected by wires, which may be attached to the elements as "leads," or added separately during construction using connection techniques known to practitioners of the art. The innovation features the inclusion of the tuning inductor in addition to the microcoil.

Figure 14:
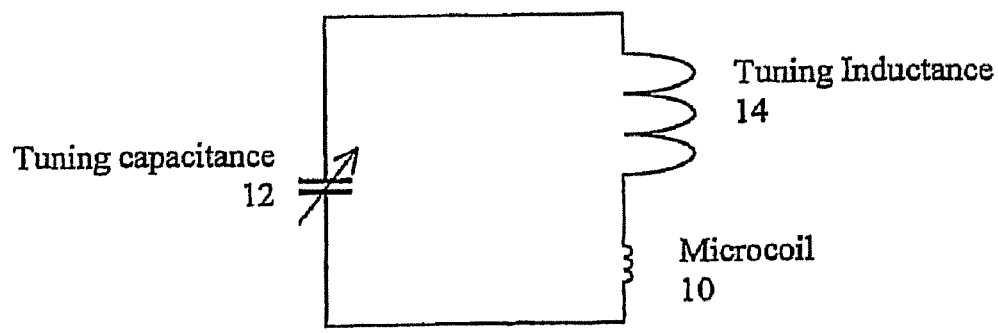
FIG. 14 is a schematic depicting a basic embodiment of an electrical LC resonating circuit according to the present disclosure, in which a tuning inductor is connected in series with a miniaturized or "micro" sample coil.

One embodiment of the circuit of the present invention is depicted in FIG. 14. This circuit is appropriate for magnetic resonance experiments, among others. The circuit of FIG. 1 may be construed as parallel or series resonant, depending upon how other MR/NMR system components are coupled to it. For the discussion immediately following, FIG. 14 may be assumed to be a parallel resonant circuit. The circuit has a microcoil 10, an adjustable tuning capacitor 12, and a second coil functioning as a tuning inductor 14. A microcoil 10, preferably having an inductance of approximately 25 nH or less, is generally much smaller than a tuning inductor. The tuning capacitance 12 and the tuning inductance 14 together constitute the principal elements of the resonant circuit. The circuit elements are connected by wires, which may be attached to the elements as "leads," or added separately during construction using connection techniques known to practitioners of the art. The presence in the circuit of both the tuning inductor 14 and the microcoil 10 is a basic facet of the present disclosure.

The microcoil 10 may be any electronically conducting structure intended to create a magnetic field at the location of a material under study. The microcoil 10 may be designed and built in any manner, using techniques known to practitioners of the art. For example, the microcoil 10 can be built by winding copper, silver, gold, or other wire to form a helical coil. The wire may be round, rectangular, or elliptical in cross section. Microcoil 10 may also be constructed by patterning a metallic layer on a non-conducting support material, so that the metallic layer has the configuration of a helix. In an experiment that uses such a coil, the material being studied is placed inside the helix. Alternatively, the microcoil 10 may be flat (or planar) in shape, and the material being studied is placed very close to a planar face of the coil. Microcoil 10 may also have the form of a flat planar coil that has been bent to define a curve, so that the concavo-convex coil fits around or inside the material under study. The microcoil 10 may also be a structure compounded of the shapes described above. The microcoil 10 may be designed and built in any manner, using proprietary or public domain techniques, as required for any particular experiment. In a first embodiment of the disclosed apparatus, the microcoil 10 preferably has an inductance sufficiently low such that, without the use of the auxiliary tuning inductor, an inconveniently large tuning capacitor would have been required.

Figure 14B:
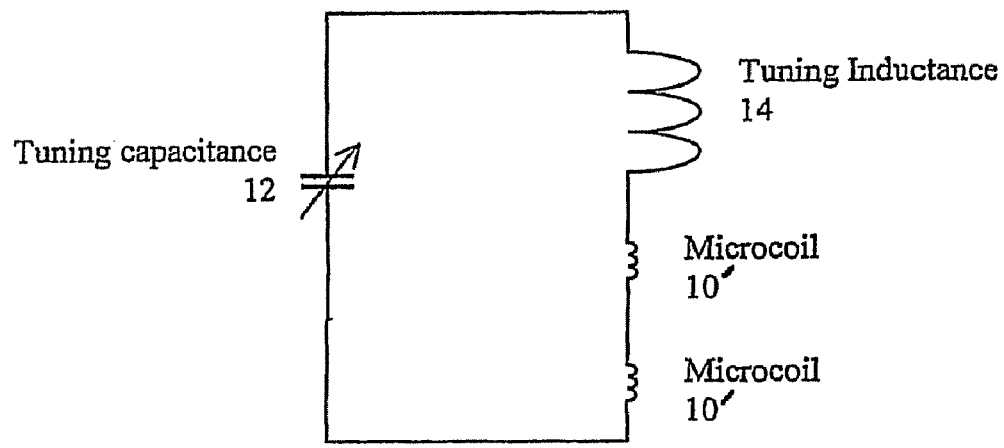
FIG. 14B is a schematic depicting the circuit shown in FIG. 14, except with the single sample coil replaced by a plurality of coils connected in parallel.
Figure 14A:
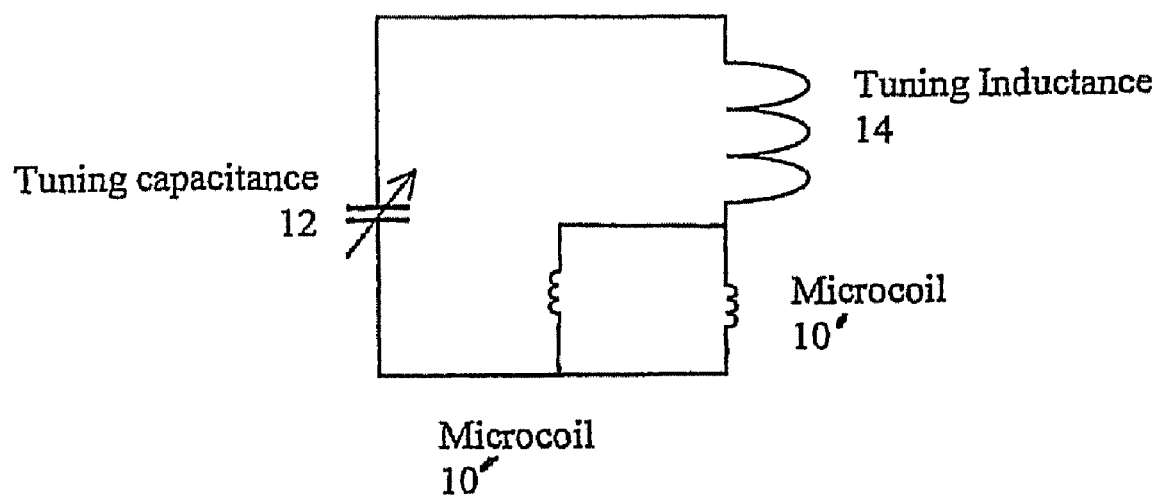
FIG. 14A is a schematic depicting the circuit shown in FIG. 14, except with the single sample coil replaced by a plurality of coils connected in series.

The microcoil 10 need not necessarily be a single coil. As particular applications may suggest, alternative circuit embodiments may substitute a plurality of microcoils 10' connected electrically in series (FIG. 14A) or in parallel (FIG. 14B) for a single coil 10. The assembled plurality of microcoils 10' is then connected in series or parallel with the tuning inductance 14 in the resonating circuit.

Similarly, the adjustable tuning capacitor 12 may be constructed from one or more capacitors, which may each be either fixed or adjustable. Any capacitor technology and any arrangement of multiple capacitors may be used.

The tuning inductor 14 is constructed using any of the techniques known in the art. For example, it may be formed from wire wound in a helix or in a flat spiral, or it may take any other form as long as it remains an inductor. The wire may be copper, silver, gold, or any other electrically conducting material. The wire may be solid, stranded, woven, a specialty wire such at "Litz" wire, or evaporated onto a capillary. The wire may be operated at a reduced temperature, and may be operated in a superconducting state. The tuning inductor 14 may be compounded of separate inductors, which each separate inductor having the same or a different construction or form.

The tuning inductor 14 very preferably has a sufficiently large inductance that it can be resonated with a tuning capacitor that is of a pragmatically convenient size. In many cases, the inductance of the tuning inductor 14 preferably is at least 2, 3, 4, 5, 6, 7, 8, 9, or 10 times larger than the inductance of the microcoil 10. Thus, the tuning coil 14 has an inductance substantially larger than the inductance of the microcoil 10, so that the microcoil is an effective magnetic resonance transmitter or receiver coil, and yet contributes no substantial inductance needed for resonance.

Figure 15:
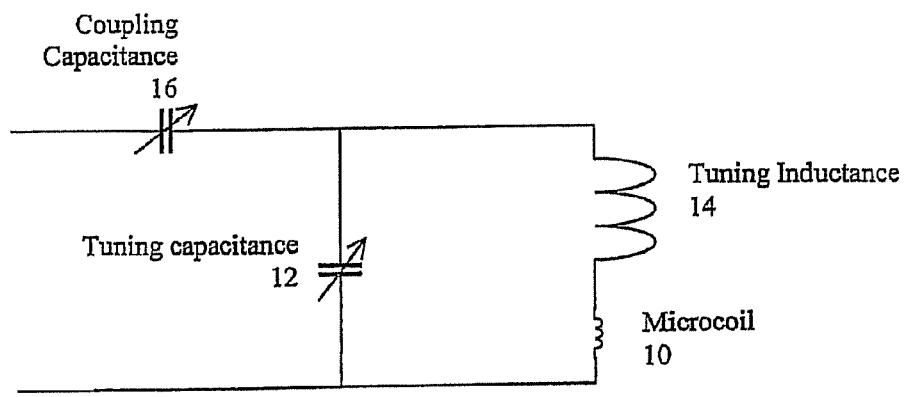
FIG. 15 is a schematic diagram indicating how an electrical circuit according to the present disclosure can be implemented in a magnetic resonance experiment.

When the closed series resonance LC circuit of FIG. 14 is in use, its electrical signals are communicated to the remainder of a NMR or MRI apparatus. This can be done in a large variety of ways. One example, shown in FIG. 15, employs a matching or "coupling" capacitor 16 connecting the junction between the tuning capacitance 12 and the tuning inductor 14. An additional connection typically is provided to the other terminal of the tuning capacitance 12, so that the overall resonance circuit presents two terminals to the remainder of the NMR/MRI electronics. A nearly limitless variety of coupling circuits, utilizing either capacitive or inductive coupling, are known to practitioners skilled in the art, and may be adapted for use in the method. All of such coupling/communication schemes apply to the microcoil tuning circuit shown in FIG. 14.

This apparatus and method is most beneficial in circumstances where the use of a very small sample coil (the "microcoil") is desired, yet while the sample coil must be brought into electrical resonance at a frequency so low that a capacitor of inconveniently large physical size otherwise would be required (i.e. if a conventional resonance circuit was employed). In describing the operation of the invention, it is assumed that the operator already possesses a microcoil, and seeks to resonate that microcoil at an inconveniently low frequency.

Known circuit theory teaches that in an LC resonant circuit, the total inductance L and total capacitance C serve to store electrical energy. The stored energy alternates between being stored in the capacitance and being stored in the inductance. The rate at which the energy moves back and forth is the electrical resonance frequency, which may be calculated using:

$$f = \frac{1}{2\pi} \frac{1}{\sqrt{LC}}$$

Hence, if the total inductance L has a very low value, a very large value of capacitance C is required to achieve a low value of the frequency f. For example, if the only inductance in the circuit is a microcoil of inductance 10 nH and the experiment is carried out in a field of only 1 Tesla (which sets the proton nuclear magnetic resonance frequency to be 42.6 MHz), the required capacitance is 1400 pF.

In the circuit of FIG. 14, the total inductance L is the sum of the inductance of the microcoil 10 and the inductance of the tuning inductor 14. By introducing the tuning inductor 14, we can raise the value of total inductance to the point where the capacitance required to achieve the appropriate electrical resonance frequency is a convenient value. In fact, the tuning inductor 14 that achieves this convenience is very similar to a standard-sized sample coil for operation at the same required frequency. Persons knowledgeable in the art of NMR/MRI circuit construction are readily enabled to construct the required tuning inductor 14.

It is preferred that the radiofrequency resistance of the tuning inductor is much less than the radiofrequency resistance of the microcoil 10. Otherwise, the tuning inductor 14 may add to the electrical noise of the resonant circuit, and the signal detection performance of the circuit is degraded. This occurs, for example, if the tuning inductor 14 is constructed from the same wire as the microcoil 10. Preferably, the tuning inductor 14 has less than about one-tenth of the RF resistance of the microcoil 10. This can be achieved, for example, by fabricating the tuning inductor 14 from very thick wire, by using stranded wire, by using Litz wire, by cooling the tuning inductor, or by using superconducting wire.

Thus, the microcoil 10 is in series with the second coil 14 which may, but need not necessarily, have a substantially larger (e.g., at least a factor of two, or even a factor of ten or more) inductance. The connected coils 10 and 14 form a resonant circuit with the capacitor 12, and the microcoil 10 functions as an effective magnetic resonance transmitter/receiver coil.

Figure 19:
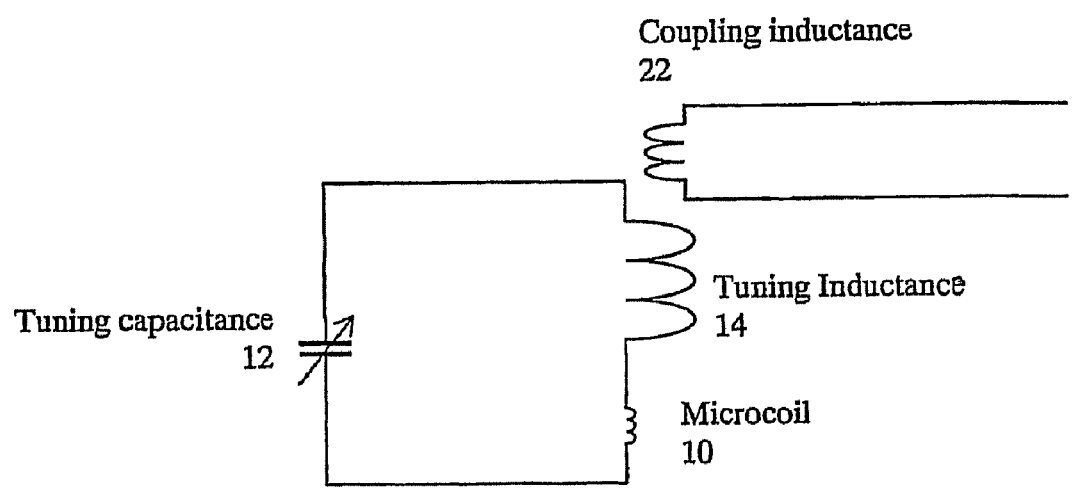
FIG. 19 is a schematic depicting a basic embodiment of an electrical LC series resonating circuit according to the present disclosure, in which a tuning inductor is connected in series with a miniaturized or "micro" sample coil.

Using a separate tuning inductor 14 with the microcoil 10 may as well be practiced in a series resonant circuit. Attention is invited to FIG. 19 in this regard. Accordingly, there is disclosed a method and apparatus for obtaining magnetic resonance signals from a microcoil 10 at low frequency, where the microcoil is electrically connected in series with a tuning coil 14 having an inductance substantially larger than the inductance of the microcoil, and yet where the microcoil functions effectively as a magnetic resonance transmitter or receiver coil while contributing no substantial inductance needed for resonance, and also where the resonant circuit of the coils 10, 14 with a capacitor may be either series resonant circuit or a parallel resonant circuit.

Figure 16:
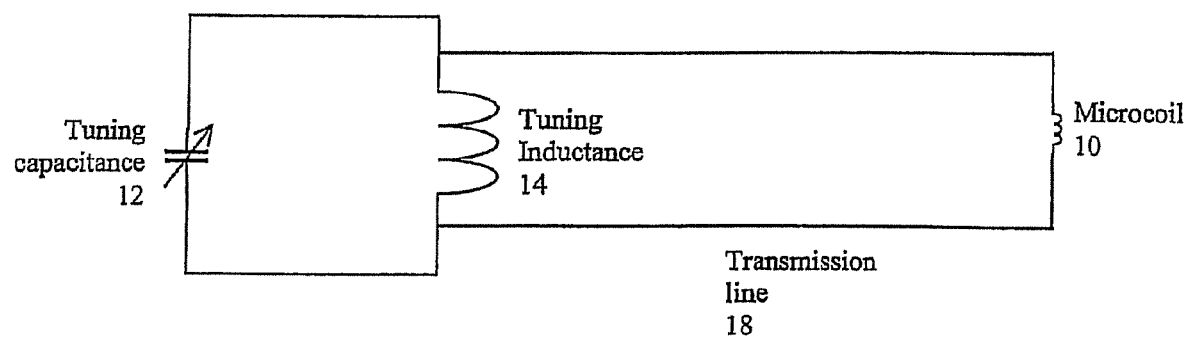
FIG. 16 is a schematic diagram depicting another embodiment of an electrical circuit according to the present disclosure, in which the miniaturized sample coil is connected in parallel with the tuning inductor via wires or cables of a length corresponding substantially to a quarter wavelength of the resonant frequency.

Attention is invited to FIG. 16, which shows an alternative embodiment of the disclosed apparatus, in which the microcoil 10 is placed some distance from the tuning capacitance 12 and the tuning inductance 14. Such an embodiment permits the invention to be practiced under circumstances where the receiving/transmitting "sensor" microcoil 10 must be remote physically from the remainder of the system, such as may be required under certain field or laboratory conditions (e.g., character or shape of the sample being evaluated, need to isolate microcoil in extreme conditions such as being placed in a cryogenic bath, and the like). The remotely located microcoil 10 is connected to the remainder of the resonant circuit by a cable or transmission line 18 that contains two separate conductors. The ends of the microcoil 10 are connected to the distal ends of the two conductors in the transmission line 18. At the proximate end of the transmission line 18, its conductors are connected to the tuning circuit elements, so that the microcoil 10 is disposed in electrical parallel with the tuning capacitance 12, the tuning inductance 14, or some portion of the tuning inductance or capacitance.

The transmission line 18 may be any electrically conducting structure that can carry signals along its length. At the frequencies of most magnetic resonance experiments, the transmission line 18 typically is a coaxial cable, although microwave-style waveguides, twisted pair wires, and other technologies known to practitioners of the art may be used. The length of the transmission line 18 is such that it achieves an impedance transformation between its proximate and distal ends (in order that the impedance of the microcoil 10 is transformed to different impedance at the point where the line 18 connects to the tuning elements 12, 14). This is most simply accomplished by providing a transmission line 18 having a length that is an odd multiple (i.e., 1x, 3x, 5x) of the length of one-fourth the wavelength of the alternating current at resonance. In this embodiment utilizing a transmission line 18, the microcoil 10 can be operated at any practically any distance from the tuning/matching components. However, a remotely operated microcoil exploits a transmission line 18 having a length of at least one-fourth the resonant wavelength. Thus, it is explicitly understood that the operation potentially may be practiced with the microcoil at practically any straight-line distance of physical separation from the tuning/matching components, regardless of the presence of the transmission line 18. But the advantage of remote operation is realized when the microcoil is functioning at a significant separation distance. Thus, in this description and in the claims, "remote" and "remotely" refer to operation of a microcoil that is located a substantial distance from the remaining elements of the resonance circuit, but remains in communication therewith by means of a transmission line. As mentioned, the transmission line 18 preferably has a length corresponding to at least one-fourth the resonant wavelength, so the microcoil 18 may function at least such a physical separation distance from the other circuit components. A skilled practitioner of the art readily understands how to select a transmission line length to achieve an impedance transformation that allows a convenient choice for the tuning capacitance 12 and tuning inductance 14.

To use this alternative embodiment, the electrical signals in the circuit of FIG. 16 are communicated to the remainder of the NMR/MRI electronics. This task is the same as previously discussed for the preferred embodiment, and may be achieved with any of the methods described there, or by other methods known to those skilled in the art. The microcoil 10, tuning capacitance 12, and tuning inductance 14 of the alternative embodiment operate substantially the same as the corresponding elements explained in the preferred embodiment of FIG. 14. The transmission line 18, however, must be constructed or selected so that it does not add appreciably to the resistance of the microcoil circuit.

Figure 17:
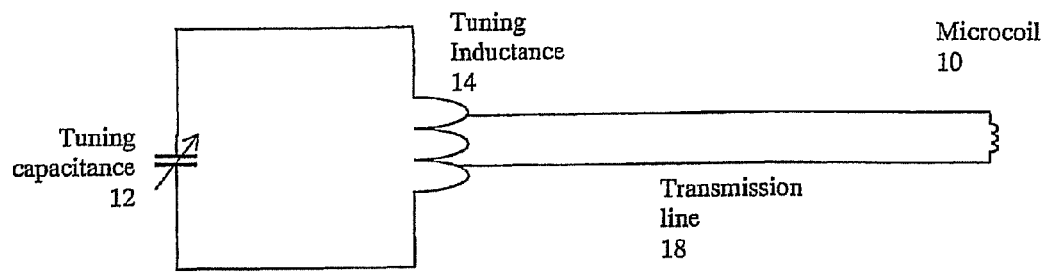
FIG. 17 is a schematic diagram, similar to FIG. 16, of yet another alternative embodiment of a circuit according to the present disclosure, showing the transmission line connected to and across a partial segment of the tuning inductor.

FIG. 17 illustrates a variation of the embodiment shown in FIG. 16. In this alternative embodiment, the microcoil 10 again is located remotely from the tuning/matching elements 12, 14. The transmission line 18 preferably has a length corresponding to an odd multiple of the length of one-fourth the wavelength of the alternating current at resonance. The microcoil 10 has a parallel connection with the tuning inductance 14; however, the transmission line 18 is connected to the tuning inductor, across a partial section thereof. Thus, only a selected segment of the overall length of the tuning coil is disposed in electrical parallel with the microcoil 10.

Figure 18:
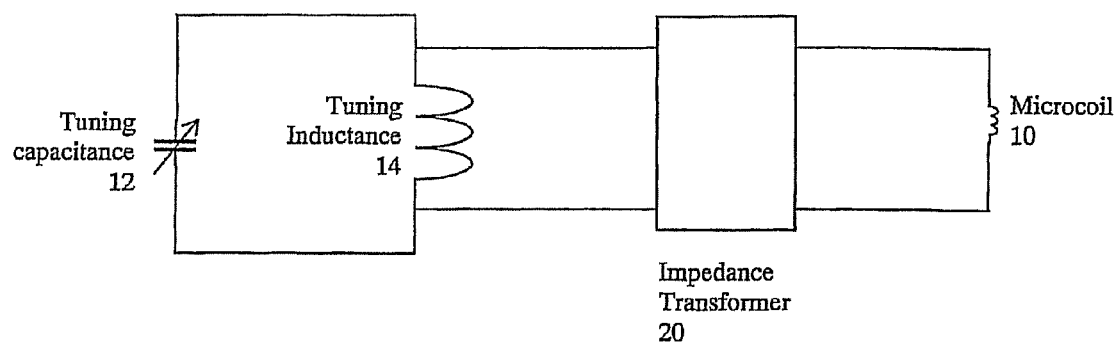
FIG. 18 is a schematic diagram, similar to FIG. 16, of yet another alternative embodiment of a circuit according to the present disclosure, showing the connection of an impedance transformer to the transmission line, between the sample coil and the tuning inductor.

Referring to FIG. 18, yet another embodiment of the "remote microcoil" version of the apparatus is disclosed which disposes an impedance transformer 20 between the microcoil 10 and the tuning inductance 14. This embodiment is substantially similar to the embodiment of FIG. 16, except that the microcoil is connected in parallel with the tuning inductance by means of the transmission line 18 and a separate impedance transformer 20. The incorporation of the impedance transformer 20 allows the microcoil 10 to be presented to the tuning inductance 14 as a large capacitor, so that the remotely located microcoil 10 is presented to the resonant circuit as a large impedance in parallel with the tuning inductance. As a result, the microcoil 10 serves as an effective magnetic resonance transmitter/receiver coil without making a significant contribution to the inductance needed for resonance.

Figure 20:
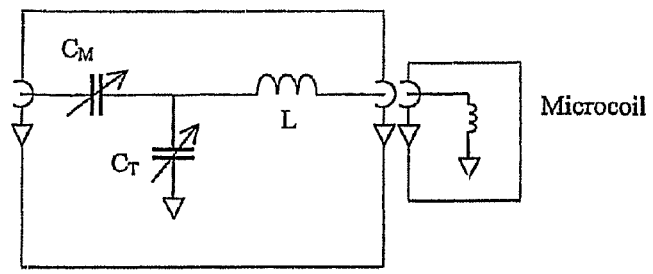
FIG. 20 is a schematic diagram elaborating somewhat on FIG. 14.
Figure 21:
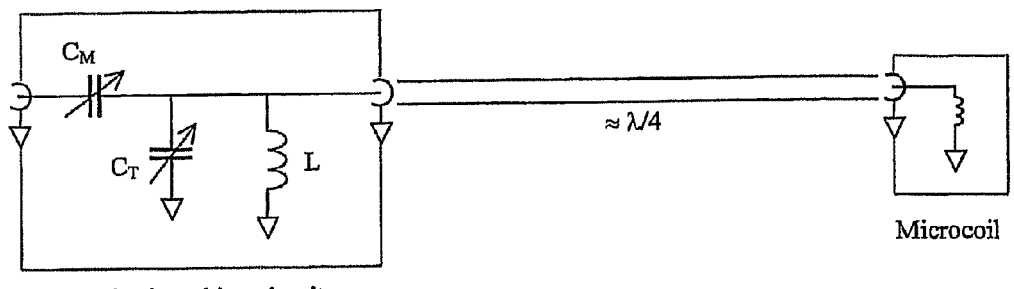
FIG. 21 is a schematic diagram elaborating somewhat on FIG. 16.

In possible applications of the foregoing disclosure, and referring to FIGS. 20 and 21, a circuit contains a variable tuning capacitance $C_T$, in resonance with an inductance, and variable coupling (or matching) capacitance $C_M$ used to properly couple the resonant circuit to the 50Ω transmitter and receiver of a NMR spectrometer (not shown). The capacitances $C_T$, $C_M$ can consist of single or multiple variable capacitors, combined in series or parallel, which may be additionally mounted in parallel or series with fixed capacitors. The inductance is the very small sample microcoil together with a (typically larger) tuning coil L.

Two examples for combining the sample microcoil and "tuning" coil are contemplated. The circuit of FIG. 20, which is an elaboration on the information provided in FIG. 14, adds the two coils in series. The circuit of FIG. 21, expanding on the disclosure of FIG. 16, places the sample coil at the distal end of a cable of length roughly equal to a quarter-wavelength at the resonant frequency. The other, proximate, end of the cable is connected in parallel with the larger coil. The effect is to transform the reactance of the sample coil to a much larger value (via the cable) and then place this reactance in parallel with the larger coil. (The small inductance of the sample coil is transformed into a larger capacitive reactance by this cable.) The value of the large inductance, L, can be chosen so that the circuit achieves electrical resonance at the desired frequency without requiring awkwardly large values for the capacitances.

The circuits of this example can be used in obtaining magnetic resonance signals from a microcoil at low frequency. It includes in most basic procedure the steps of connecting a microcoil in series to a second, tuning, coil typically having a substantially larger inductance, and forming a resonant circuit of the combined coils with a capacitor, such that the microcoil functions as an effective magnetic resonance transmitter/receiver coil, but without the microcoil making a significant contribution to the inductance needed for parallel resonance so that the capacitor's capacitance is determined primarily by the inductance of the tuning coil. It should be appreciated that connecting a microcoil in series with a second, tuning, coil may be a step of connecting electrically in mutual series a plurality of microcoils, so that an assembly of coils may be substituted for a single microcoil. Alternatively, such a plurality of microcoils may be mutually connected in parallel to constitute the assembly of coils that is substituted for a single microcoil, and then connecting the plural assembly in series with the second or "tuning" coil.

A method according to this disclosure permits obtaining magnetic resonance signals, at low frequency, from a microcoil located remotely from the tuning/matching elements. This benefit is realized by connecting, in parallel, a microcoil and a second or tuning coil with a transmission line that is an odd multiple of the length of one-fourth of the wavelength of the alternating current at resonance. The second coil is constructed to provide with a substantially larger inductance and is electrically connected to a capacitor to form part of a parallel resonant circuit. The remotely located microcoil presents as large impedance in parallel to the second coil to act as an effective magnetic resonance transmitter/receiver coil, yet without making a significant contribution to the inductance needed for parallel resonance. As with the basic preferred process, connecting a microcoil in parallel with a second or "tuning" coil may be the step of connecting in mutual series or in parallel a plurality of micro coils, so that an assembly of microcoils may be substituted for a single microcoil.

In the method for obtaining magnetic resonance signals from a microcoil located remotely from the tuning/matching elements and at low frequency, the process steps may include connecting in parallel the microcoil with a cable that is an odd multiple of the length of one-fourth the wavelength of the alternating current at resonance to only a partial section of the large-inductance second coil. Connecting these with a capacitor to provide a resonant circuit, an apparatus thereby is provided whereby the remotely located microcoil will function as impedance in parallel to the second coil to act as an effective magnetic resonance transmitter/receiver, coil without making a significant contribution to the inductance needed for parallel resonance.

Alternative method steps include connecting in parallel the microcoil with a transmission line and an impedance transformer that will present the microcoil as a large capacitor to a second coil having substantially larger inductance, and connecting these to a capacitor to define part of a resonant circuit, whereby the microcoil at a distance from the resonant circuit presents the microcoil as a large impedance in parallel to the said second coil to be an effective magnetic resonance transmitter/receiver coil without making a significant contribution to the inductance needed for resonance.

In sum, "extra" inductance, in the form of a large coil, is deliberately included in the circuit of this example. Such stray inductance is generally and previously regarded as flaw in NMR resonant circuit design, due to an assumption that the stray inductance will decrease the efficiency of signal detection. However, we have determined that application of known circuit design principles avoids degradation in detection efficiency, provided the extra inductance does not add appreciably to the electrical resistance of the circuit. Conventional circuit design approaches for NMR resonant circuits, which do not allow the extra inductance, are not capable of yielding practical, easy-to-tune circuits for small sample coils operating at low resonance frequencies, such as below 100 MHz. Indeed, no resonant circuits for very small sample coils (<25 nH impedance) are known to be operable at resonant frequencies below 100 MHz. According to the present example, the capacitances and tuning inductance can be mounted in a position remote from the "micro" sample coil. Readily manipulated knobs or other adjustment aids can be attached to the capacitances, since they are not subject to space constraints. A transmission cable can be used to connect the sample coil to the main resonant circuit, facilitating remote operation and the miniaturization of a NMR probe.

Various arrangements and embodiments in accordance with the present invention have been described herein. All embodiments of each aspect of the invention can be used with embodiments of other aspects of the invention. It will be appreciated, however, that those skilled in the art will understand that changes and modifications may be made to these arrangements and embodiments, as well as combinations of the various embodiments without departing from the true scope and spirit of the present invention, which is defined by the following claims.

REFERENCES

[1] T. L. Peck, R. L. Magin, and P. C. Lauterbur, "Design and Analysis of Microcoils for NMR Microscopy," *J. Magn. Reson.* B108, 114-124 (1995).

[2] D. L. Olsen, T. L. Peck, A. G. Webb, R. L. Magin, and J. V. Sweedler, "High-resolution microcoil $^1$H-NMR for mass-limited, nanoliter-volume samples," *Science,* 270, 1967 (1995).

[3] A. G. Webb and S. C. Grant, "Signal-to-Noise and Magnetic Susceptibility Trade-offs in Solenoidal Microcoils for NMR," *J. Magn. Reson.,* B113, 83-87 (1996).

[4] J. A. Rogers, R. J. Jackman, G. M. Whitesides, D. L. Olson, and J. V. Sweedler, "Using microcontact printing to fabricate microcoils on capillaries for high resolution proton nuclear magnetic resonance on nanoliter volumes," *Appl. Phys. Lett.,* 70, 2464-2466 (1997).

[5] J. E. Stocker, T. L. Peck, A. G. Webb, M Feng, R. L. Magin, "Nanoliter Volume, High-Resolution NMR Microspectroscopy Using a 60-um Planer Microcoil", *IEEE Trans. Biomed. Eng.* 44, 1122-1127 (1997).

[6] B. Behnia and A. G. Webb, "Limited-Sample NMR Using Solenoidal Microcoils, Perfluorocarbon Plugs, and Capillary Spinning," *Anal. Chem.,* 70, 5326-5331 (1998).

[7] R. Subramanian, M. M. Lam, and A. G. Webb, "RF Microcoil Design for Practical NMR of Mass-Limited Samples," *J. Magn. Reson.* 133, 227-231 (1998).

[8] D. L. Olson, M. E. Lacey, and J. V. Sweedler, "High-resolution microcoil NMR for analysis of mass-limited, nanoliter samples," *Analytical Chem.,* vol. 70, pp. 645-650, 1998.

[9] V. Malba, R. Maxwell, L. B. Evans, A. F. Bernhardt, M Cosman, and K. Yan, "Laser-lathe Lithography—A Novel Method for Manufacturing Nuclear Magnetic Resonance Microcoils," *Biomed. Microdev.*, 5, 21-27 (2003).

[10] D. Djukovic, S. Liu, I. Henry, B. Tobias, and D. Rafferty, "Signal Enhancement in HPLC/Microcoil NMR Using Automated Column Trapping," *Anal Chem.*, 78, 7154-7160 (2006).

[11] N. Wu, T. L. Peck, A. G. Webb, R. L. Magin, and J. V. Sweedler, "$^1$H-NMR Spectroscopy on the Nanoliter Scale for Static and On-Line Measurements," *Anal Chem.* 66, 3849 (1994).

[12] J. D. Trumbull, I. K. Glasgow, D. J. Beebe, and R. L. Magin, IEEE Trans. Biomed. Eng. 47, 3 (2000).

[13] C. Massin, F. Vincent, A. Homsy, K. Ehrmann, G. Boero, P.-A. Besse, A. Daridon, E. Verpoorte, N. F. de Rooij, and R. S. Popovic, "Planar microcoil-based microfluidic NMR probes," *J. Magn. Reson.*, 164, 242-255 (2003).

[14] B. Sorli, J. F. Chateaux, M. Pitaval, H. Chahboune, B. Favre, A. Briguet, and P. Morin, "Micro-spectrometer for NMR: analysis of small quantities in vitro," *Meas. Sci. Technol.*, 15, 877-880 (2004).

[15] D. A. Seeber, J. H. Hoftiezer, W. B. Daniel, M. A. Rutgers, and C. H. Pennington, "Triaxial magnetic field gradient system for microcoil magnetic resonance imaging," *Rev. Sci. Inst.*, 71, 4263-4272 (2000).

[16] S. C. Grant, N. R. Aiken, H. D. Plant, S. Gibbs, T. H. Mareci, A. G. Webb, and S. J. Blackband, "NMR Spectroscopy of Single Neurons," *Magn. Reson. Med.*, 44, 19-22 (2000).

[17] D. A. Seeber, R. L. Cooper, L. Ciobanu, and C. H. Pennington, "Design and testing of high sensitivity microreceiver coil apparatus for nuclear magnetic resonance and imaging," *Rev. Sci. Inst.* 72, 2171-2179 (2001).

[18] S. C. Grant, L. A. Murphy, R. L. Magin, and G. Friedman, "Analysis of Multilayer Radio Frequency Microcoils for Nuclear Magnetic Resonance Spectroscopy," *IEEE Trans. Magn.* 37, 2989-2998 (2001).

[19] L. Ciobanu and C. H. Pennington, "3D micron-scale MRI of single biological cells," *Solid State Nucl. Magn. Reson.* 25, 138-141 (2004).

[20] H. Wensink, D. C. Hermes, A. van den Berg, "High signal to noise ratio in low-field NMR on a chip: Simulations and experimental results," 17$^{th}$ *IEEE MEMS*, 407-410 (2004).

[21] G. Moresi and R. L. Magin, "Miniature permanent magnet for table-top NMR," *Concept. Magn. Res.*, 19B, 35-43 (2003).

[22] A. G. Goloshevsky, J. H. Walton, M. V. Shutov, J. S. de Ropp, S. D. Collins, M. J. McCarthy, "Development of low field nuclear magnetic resonance microcoils," Rev. Sci. Inst., 76, 024101 (2005).

[23] A. G. Goloshevsky, J. H. Walton, M. V. Shutov, J. S. de Ropp, "Integration of biaxial planar gradient coils and an RF microcoil for NMR flow imaging," Meas. Sci. Technol., 16, 505-512 (2005).

[24] Halbach K, "Design of permanent multipole magnets with oriented rare earth cobalt material," *Nuclear Instrum Methods,* 169, 1-10 (1980).

[25] E. Fukushima and S. B. W. Roeder, *Experimental Pulse NMR*, (New York: Addison-Wesley, 1981).

[26] L. O. Sillerud, A. F. McDowell, N. L. Adolphi, R. E. Serda, D. P. Adams, M. J. Vasile, T. M. Alam, "$^1$H NMR Detection of superparamagnetic nanoparticles at 1 T using a microcoil and novel tuning circuit," *J. Magn. Reson.*, 181, 181-190 (2006).

[27] D. I. Hoult and R. E. Richards, "The Signal-to-Noise Ratio of the Nuclear Magnetic Resonance experiment," J. Magn. Reson. 24, 71-85 (1976).

[28] J. B. Johnson, "Thermal Agitation of Electricity in Conductors," *Phys. Rev.,* 32, 97-109 (1928).

[29] H. Nyquist, "Thermal Agitation of Electric Charge in Conductors," *Phys. Rev.,* 32, 110-113 (1928).

We claim:

1. A module comprising
   (a) a microcoil possessing an inner diameter of between 25 microns and 550 microns;
   (b) a tuning inductor operably coupled to the microcoil;
   (c) a conduit disposed proximate to the microcoil, wherein the conduit is in fluid communication with a sample reservoir;
   (d) an affinity column in fluid communication with the conduit and the sample reservoir; and
   (e) a connector for connecting the module to a magnetic resonance detector.

2. The module of claim 1, wherein the affinity column is located upstream of the conduit.

3. The module of claim 1, wherein the microcoil is wound around the conduit.

4. The module of claim 1 wherein the affinity column is located at least partially within the microcoil.

5. The module of claim 1 further comprising a sequestration chamber in fluid communication with the fluidic system, wherein the sequestration chamber is located downstream from the conduit.

6. The module of claim 1 wherein the affinity column comprises two or more layers, and wherein each layer comprises a different capture agent.

7. The module of claim 1, wherein the module comprises a plurality of microcoils each possessing an inner diameter of between 25 microns and 550 microns; wherein a conduit is disposed proximate to each microcoil; wherein the fluidic system is in fluid communication with each conduit, and wherein the fluidic system comprises a plurality of branches.

8. A magnetic resonance detector, comprising
   (a) a housing comprising a conduit guide;
   (b) a permanent magnet possessing a field strength of less than or equal to 4 Tesla within the housing; and
   (b) the module of claim 1, wherein the connector connects the module to the housing via the conduit guide.

9. A module comprising
   (a) a plurality of microcoils each possessing an inner diameter of between 25 microns and 550 microns;
   (b) a plurality of tuning inductors operably coupled to the plurality of microcoils;
   (c) a conduit disposed proximate to each microcoil, wherein the conduit is in fluid communication with a sample reservoir; and
   (d) a connector for connecting the module to a magnetic resonance detector.

10. The module of claim 9, wherein the plurality of microcoils are disposed along a single flow path in the fluidic system.

11. The module of claim 9, wherein the plurality of microcoils are along independent fluid flow paths.

12. The module of claim 9, wherein the plurality of microcoils is electrically connected to form a multi-coil detection circuit.

13. The module of claim 9 further comprising one or more sequestration chambers located downstream from the microcoils.

14. The module of claim 9, further comprising at least one affinity column in fluid communication with at least one conduit.

15. The module of claim 14, wherein the at least one affinity column is located upstream of the at least one conduit.

16. The module of claim 14, wherein each individual microcoil is wound around the conduit disposed proximate to the individual microcoil.

17. The module of claim 16 wherein the at least one affinity column is located at least partially within at least one microcoil.

18. A magnetic resonance detector, comprising
    (a) a housing comprising a conduit guide;
    (b) a permanent magnet possessing a field strength of less than or equal to 4 Tesla within the housing; and
    (b) the module of claim 9, wherein the connector connects the module to the housing via the conduit guide.

19. A detection device, comprising
    (a) a permanent magnet possessing a field strength of less than or equal to 4 Tesla;
    (b) a microcoil disposed proximate to a magnetic field generated by the permanent magnet, wherein the microcoil possesses an inner diameter of between 25 microns and 550 microns;
    (c) a tuning inductor operably coupled to the microcoil;
    (d) a conduit disposed proximate to the microcoil, wherein the conduit is in fluid communication with a sample reservoir; and
    (e) an affinity column in fluid communication with the conduit and the sample reservoir.

20. A detection device, comprising
    (a) a permanent magnet possessing a field strength of less than or equal to 4 Tesla;
    (b) a plurality of microcoils each possessing an inner diameter of between 25 microns and 550 microns, wherein each microcoils is an effective magnetic resonance transmitter or receiver coil;
    (c) a plurality of tuning inductors operably coupled to the plurality of microcoils; and
    (d) a conduit disposed proximate to each microcoil, wherein the conduit is in fluid communication with a sample reservoir.

\* \* \* \* \*